(12) United States Patent  
Dasgupta et al.

(10) Patent No.: US 7,807,874 B2  
(45) Date of Patent: Oct. 5, 2010

(54) STRESS TOLERANT PLANTS AND METHODS THEREOF

(75) Inventors: Santana Dasgupta, Bangalore (IN); Targolli L. Jayaprakash, Bangalore (IN); Carolyn J. Thai, O'Fallon, MO (US); Kottaram Krishnadas Narayanan, Bangalore (IN); Thomas G. Ruff, Wildwood, MO (US); Stanton B. Dotson, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 339 days.

(21) Appl. No.: 11/007,819

(22) Filed: Dec. 8, 2004

(65) Prior Publication Data

US 2005/0235377 A1    Oct. 20, 2005

Related U.S. Application Data

(60) Provisional application No. 60/528,540, filed on Dec. 10, 2003.

(51) Int. Cl.
  *C12N 15/82* (2006.01)
  *A01H 5/00* (2006.01)

(52) U.S. Cl. ............... 800/289; 800/298; 800/320.1; 800/312; 800/320.3; 800/314; 800/320.2; 800/306

(58) Field of Classification Search ............... None
  See application file for complete search history.

(56) References Cited

U.S. PATENT DOCUMENTS 6,777,587 B1 * 8/2004 Bisaro .................. 800/279
2002/0095032 A1  7/2002 Zhu et al. ............... 536/23.1

FOREIGN PATENT DOCUMENTS

WO   WO 01/07570   2/2001
WO   WO 01/45492   6/2001

OTHER PUBLICATIONS

Annen F. et al. Characterization of a Sorghum bicolor gene family encoding putative protein kinases with a high similarity to the yeast SNF1 protein kinase. Plant Mol Biol. Mar. 1998;36(4):529-39.*
Ohba H. et al. Diverse response of rice and maize genes encoding homologs of WPK4, an SNF1-related protein kinase from wheat, to light, nutrients, low temperature and cytokinins. Mol Gen Genet. Mar. 2000;263(2):359-66.*
Hardie D.G. et al. The AMP-activated/SNF1 protein kinase subfamily: metabolic sensors of the eukaryotic cell? Annu. Rev. Biochem. 1998, 67:821-55.*
Ohba H. et al. Genbank Accession BAA83688, coded by AB011967, May 10, 2000.*
Ohba H. et al. Genbank Accession AB011967, *Oryza sativa* OsPK4 gene, complete cds. May 10, 2000.*
Lamberg A. et al. Site-directed mutagenesis of the alpha subunit of human prolyl 4-hydroxylase. Identification of three histidine residues critical for catalytic activity. J Biol Chem. Apr. 28, 1995;270(17):9926-31.*
Falcon-Perez JM et al. Functional domain analysis of the yeast ABC transporter Ycf1p by site-directed mutagenesis. J Biol Chem. Aug. 13, 1999;274(33):23584-90.*
May M.J. et al. Evidence for posttranscriptional activation of gamma glutamylcysteine synthetase during plant stress responses. Proc Natl Acad Sci U S A. Sep. 29, 1998;95(20):12049-54.*
Albrecht et al., "The NAF domain defines a novel protein-protein interaction module conserved in Ca$^{2+}$-regulated kinases," *The EMBO Journal*, 20(5):1051-1063, 2001.
Alderson et al., "Complementation of snf1, a mutation affecting global regulation of carbon metabolism in yeast, by a plant protein kinase cDNA," *Proc. Natl. Acad. Sci. USA*, 88:8602-8605, 1991.
Annen et al., "Characterization of a sorghum bicolor gene family encoding putative protein kinases with a high similarity to the yeast SNF1 protein kinase," *Plant Molecular Biology*, 36:529-539, 1998.
Chikano et al., "Two novel genes encoding SNF1-related protein kinases from *Arabidopsis thaliana*: differential accumulation of AtSR1 and AtSR2 transcripts in response to cytokinins and sugars, and phosphorylation of sucrose synthase by AtSR2," *Mol Gen Genet*, 264:674-681, 2001.
Chinchilla et al., "Ankyrin protein kinases: a novel type of plant kinase gene whose expression is induced by osmotic stress in alfalfa," *Plant Mol. Bio.*, 51:555-566, 2003.
Gong et al., "Biochemical and functional characterization of PKS11, a novel *Arabidopsis* protein kinase," *J. of Biol. Chem.*, 277(31):28340-28350, 2002.
Halford et al., "Molecular analyses of a barley multigene family homologous to the yeast protein kinase gene SNF1," *Plant J.*, 2:791-797, 1992.
Halford et al., "SNF1-related protein kinases: global regulators of carbon metabolism in plants," *Plant Mol. Bio.*, 37:735-748, 1998.
Hannappel et al., "Differential expression of two barley SNF1-related protein kinase genes," *Plant Mol. Biol.*, 27:1235-1240, 1995.
Hardie et al., "The AMP-activated/SNF1 protein kinase subfamily: metabolic sensors of the eukaryotic cell," *Ann. Rev. Biochem*, 67:821-855, 1998.
Ikeda et al., "Specific binding of a 14-3-3 protein to autophosphorylated WPK4, an SNF1-related wheat protein kinase, and to WPK4-phosphorylated nitrate reductase," Additions and Corrections, *The Journal of Biological Chemistry*, 275(52):41528-41530, 2000.
Ikeda et al., "Specific binding of a 14-3-3 protein to autophosphorylated WPK4, and SNF1-related wheat protein kinase, and to WPK4-phosphorylated nitrate reductase," *J. of Biol. Chem.*, 275(41):31695-31700, 2000.

(Continued)

*Primary Examiner*—Cynthia Collins
(74) *Attorney, Agent, or Firm*—Nikki Davis, Esq.; Sonnenschein Nath & Rosenthal LLP

(57) ABSTRACT

The present invention provides a method and DNA molecules that when expressed in a plant produces transgenic plants with improved abiotic stress tolerance. The invention includes plant expression vectors comprising the DNA molecules, and plants containing such DNA molecules.

16 Claims, 10 Drawing Sheets

OTHER PUBLICATIONS

Ikeda et al., "Sucrose and cytokinin modulation of WPK4, a gene encoding a SNF1-related protein kinase from wheat," *Plant Physiology*, 121:813-820, 1999.

Kim et al., "Isolation and characterization of a novel rice Ca2+-regulated protein kinase gene involved in responses to diverse signals including cold, light, cytokinins, sugars and salts," *Plant Mol. Biol.*, 52(6):1191-1202, 2003.

LeGuen et al., "Structure and expression of a gene from *Arabidopsis thaliana* encoding a protein related to SNF1 protein kinase," *Gene*, 120:249-254, 1992.

Muranaka et al., "Characterization of tobacco protein kinase NPK5, a homolog of *Saccharomyces cerevisiae* SNF1 that constitutively activates expression of the glucose-repressible SUC2 gene for a secreted invertase of *S. cerevisiae*," *Mol. Cell. Biol.*, 14:2958-2965, 1994.

Ohba et al., "Diverse response of rice and maize genes encoding homologs of WPK4, and SNF-1-related protein kinase from wheat, to light, nutrients, low temperature and cytokinins," *Mol Gen Genet*, 263:359-366, 2000.

Rolland et al., "Sugar sensing and signaling in plants," *The Plant Cell*, S185-S205, Supplement, 2002.

Sano et al., "Light and nutritional regulation of transcripts encoding a wheat protein kinase homolog is mediated by cytokinins," *Proc. Natl. Acad. Sci.USA*, 91:2582-2586, 1994.

Steward et al., "Expression of AmMET1, a gene encoding a DNA methyltransferase from maize, is associated not only with DNA replication in actively proliferating cells, but also with altered DNA methylation status in cold-stressed quiescent cells," *Nucleic Acids Research*, 28(17):3250-3259, 2000.

Takano et al., "Rice has two distinct classes of protein kinase genes related to SNF1 of *Saccharomyces cerevisiae*, which are differently regulated in early seed development," *Mol Gen Genet.*, 260(4):388-394, 1998.

Hrabak et al., "The *Arabidopsis* CDPK-SnRK superfamily of protein kinases," *Plant Physiology*, 132:666-680, 2003.

\* cited by examiner

STRESS TOLERANT PLANTS AND METHODS THEREOF

CROSS REFERENCE TO RELATED APPLICATIONS

This application claims benefit of priority under 35 U.S.C. §119(e) to U.S. Provisional Application No. 60/528,540 filed on Dec. 10, 2003, which is herein incorporated in its entirety by reference.

INCORPORATION OF SEQUENCE LISTING

Two copies of the sequence listing (Seq. Listing Copy 1 and Seq. Listing Copy 2) and a computer-readable form of the sequence listing, all on CD_ROMs, each containing the file named OsPK7Regular Filing.ST25.txt, which is 153,600 bytes (measured in MS-DOS) and was created on Dec. 07, 2004, are hereby incorporated by reference.

FIELD OF THE INVENTION

Described herein are inventions in the field of plant molecular biology and plant genetic engineering. In particular, DNA constructs encoding a polypeptide and transgenic plants containing the DNA constructs are provided. The transgenic plants are characterized by improved stress tolerance.

BACKGROUND OF THE INVENTION

One of the goals of plant genetic engineering is to produce plants with agronomically, horticulturally or economically important characteristics or traits. Traits of particular interest include high yield, improved quality and yield stability. The yield from a plant is greatly influenced by external environmental factors including water availability and heat, of which tolerance of extremes is in turn influenced by internal developmental factors. Enhancement of plant yield may be achieved by genetically modifying the plant to be tolerant to yield losses due to stressful environmental conditions, such as heat and drought stress.

Seed and fruit production are both limited inherently due to abiotic stress. Soybean (Glycine max), for instance, is a crop species that suffers from loss of seed germination during storage and fails to germinate when soil temperatures are cool (Zhang et al., Plant Soil 188: (1997)). This is also true in corn and other plants of agronomic importance. Improvement of abiotic stress tolerance in plants would be an agronomic advantage to growers allowing enhanced growth and/or germination in cold, drought, flood, heat, UV stress, ozone increases, acid rain, pollution, salt stress, heavy metals, mineralized soils, and other abiotic stresses.

Traditional breeding (crossing specific alleles of one genotype into another) has been used for centuries to increase abiotic stress tolerance and yield. Traditional breeding is limited inherently to the limited number of alleles present in the parental plants. This in turn limits the amount of genetic variability that can be added in this manner. Molecular biology has allowed the inventors of the instant invention to look far and wide for genes that will improve stress tolerance in plants. Protein phosphorylation is one of the major mechanisms controlling cellular functions in response to external signals in eukaryotes and kinases represent a large and diverse protein family. Protein kinases in plants have been shown to participate in a wide variety of developmental processes. Protein kinases also respond to environmental stresses Members of the Snf1-related protein kinases play a major role in phosphorylation cascades involved in carbon assimilation in animals, fungi and plants. (Hardie D. G., Carling D. and Carlson M.; Ann. Rev. Biochem. 67: 821-855, 1998). Members of the AMP-activated/Snf1-related protein kinase subfamily are central components of highly conserved protein kinase cascades that now appear to be present in most, if not all, eukaryotic cells. Because the downstream targets of the action of these enzymes are many and varied, they have been discovered and rediscovered several times in different guises and by different approaches. Alderson and coworkers (Alderson A., et al. Proc. Natl. Acad. Sci. USA, 88: 8602-8605, 1991) cloned and sequenced a cDNA (RKIN1) encoding a Snf1 homolog from the higher plant rye. Transformation of an Snf1 mutant strain of yeast with a low-copy RKIN1 plasmid restored the ability to grow on nonfermentable carbon sources (Alderson A., et al. Proc. Natl. Acad. Sci. USA, 88: 8602-8605, 1991), showing that RKIN1 is functionally as well as structurally related to Snf1. Snf1 homologs were subsequently cloned from *Arabidopsis thaliana* (LeGuen L., Thomas M., Bianchi M., Halford N. G., and Kreis M., Gene 120: 249-254, 1992), barley, (Hannappel U., Vincente-Carbajosa J., Baker J. H. A., Shewery P. R., and Halford N. G., Plant Mol. Biol., 27:1235-1240, 1995; Halford N. G., Vincente-Carbajosa J., Sabelli P. A., Shewery P. R., Hannappel U., and Kreis M., Plant J., 2: 791-797, 1992), tobacco (Muranaka T., Banno H., Machida Y., Mol. Cell. Biol. 14: 2958-2965, 1994) rice and maize (Ohba H. et al. Mo Genet., 263: 359-366, 2000). Two Snf1-related protein kinases from rice, OsPK4 and OsPK7, which are structurally very similar and share more than 75% homology with the wheat homolog WPK4, exhibit very different expression patterns as well as stress response in rice and maize plants (Ohba H. et al. Mo Genet., 263: 359-366, 2000). Based on yeast studies, Snf1 protein kinases including, OsPK4 and OsPK7, are expected to play a central role in energy metabolism to provide protection against environmental stress in the host organism. Very little or no changes were observed in the expression pattern of rice and maize OsPK7 genes in response to a variety of abiotic stresses such as light, nutrients, cold, drought, and salt. (Ohba H. et al. Mo Genet., 263: 359-366, 2000).

The current invention demonstrates and claims the utilization of the OsPK7 gene and its homologs to produce plants with enhanced abiotic stress tolerance, including response to suboptimal growth temperatures and amounts of water required for growth of natural plants.

SUMMARY OF THE INVENTION

In one embodiment, the present invention provides a method of generating a transgenic plant with enhanced stress tolerance comprising the steps of transforming a plant cell with a DNA construct comprising a promoter that functions in the plant cell, operably linked to a DNA molecule that encodes a protein substantially homologous to a protein selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, and SEQ ID NO: 51 and operably linked to a 3'termination region; and regenerating the plant cell into a fertile transgenic plant; and selecting said fertile transgenic plant containing the DNA construct; wherein the fertile transgenic plant exhibits enhanced stress tolerance compared to a plant of the same plant species not transformed to contain said DNA construct.

In one preferred embodiment of the invention a DNA construct is provided that contains a promoter that is a plant virus promoter. In another preferred embodiment of the invention a DNA construct is provided that contains a promoter that is a heterologous plant promoter. In another preferred embodiment of the invention the DNA construct contains a promoter that is a tissue specific or tissue enhanced promoter. In one aspect of the invention, the DNA construct contains a promoter that is a constitutive promoter. In another aspect of the invention the DNA construct contains a promoter that is a promoter that is found in association with the native gene in the genome.

In another preferred embodiment, the DNA molecule is substantially homologous to a DNA molecule selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 28, SEQ ID NO: 30, SEQ ID NO: 32, SEQ ID NO: 34, SEQ ID NO: 36, SEQ ID NO:38, SEQ ID NO: 40, SEQ ID NO: 42, SEQ ID NO: 44, SEQ ID NO: 46, and SEQ ID NO: 50.

In another aspect of the invention a transgenic plant containing the DNA construct is provided wherein the transgenic plant exhibits enhanced stress tolerance. The transgenic plant is particularly tolerant to cold stress.

The transgenic plant is selected from the group consisting of: *Acacia*, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, cauliflower, celery, cherry, cilantro, citrus, clementines, coffee, corn, cotton, cucumber, Douglas fir, eggplant, endive, escarole, eucalyptus, fennel, figs, forest tree, gourd, grape, grapefruit, honey dew, jicama, kiwifruit, lettuce, leeks, lemon, lime, loblolly pine, mango, melon, millet, mushroom, nut, oat, okra, onion, orange, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, southern pine, soybean, spinach, squash, strawberry, sugarbeet, sugarcane, sunflower, sweet potato, sweetgum, tangerine, tea, tobacco, tomato, turf, a vine, watermelon, wheat, yams, and zucchini.

The present invention also provides a transgenic plant with enhanced stress tolerance compared to a plant of the same plant species comprising a DNA construct wherein the DNA construct comprises a promoter that functions in plants operably linked to a DNA molecule that encodes a protein substantially homologous to a protein selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, and SEQ ID NO: 51 and operably linked to a 3'termination region.

The present invention also provides a DNA construct wherein the DNA construct comprises a promoter that functions in plants operably linked to a DNA molecule that encodes a protein substantially homologous to a protein selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, and SEQ ID NO: 51, and operably linked to, a 3'termination region.

Figure 1:
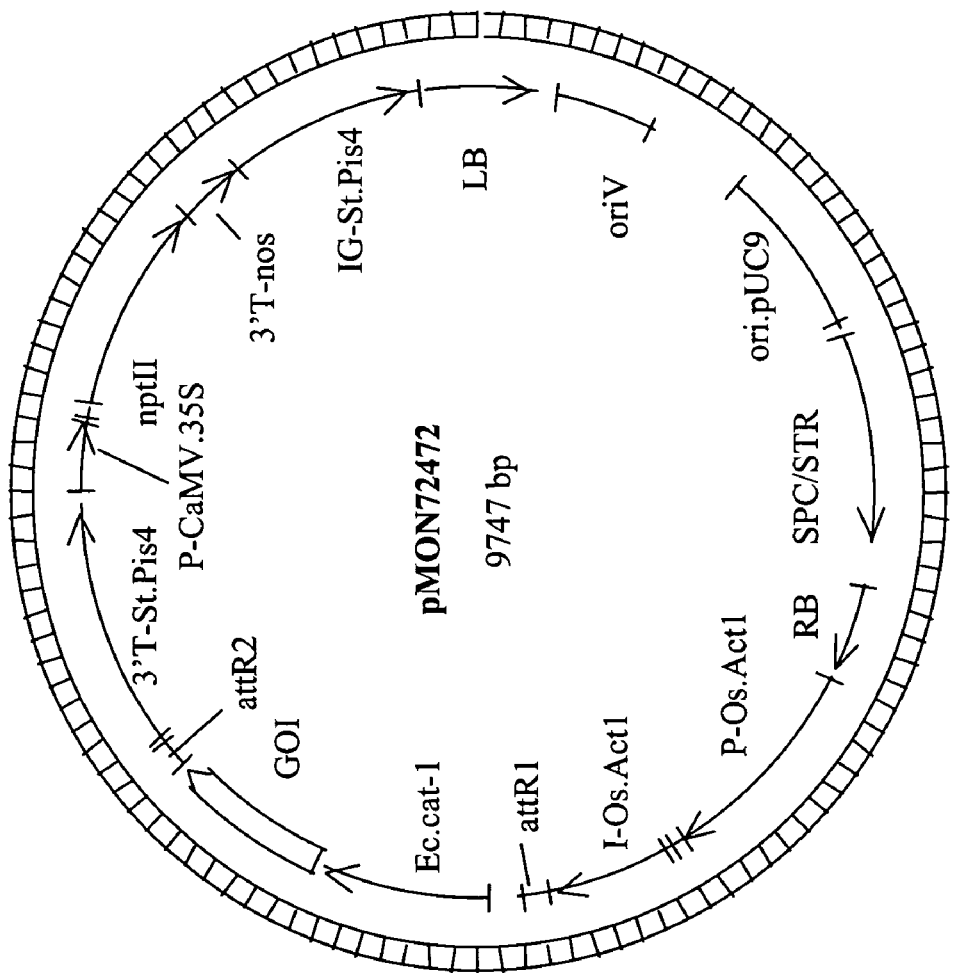
FIG. 1 Plasmid map of plant expression vector pMON 72472

The invention can be more fully understood from the following detailed description and the accompanying Sequence Listing that form a part of this application.

DETAILED DESCRIPTION OF THE INVENTION

The present invention is based, in part, on the identification of polynucleic acid molecules encoding polypeptides of the present invention from plants including maize, rice and soybean and utilizing these molecules to enhance abiotic stress tolerance in plants by ectopic expression of polypeptides of the invention leading to potential enhancement in yield.

Isolated Polynucleic Acid Molecules of the Present Invention

The term "polynucleic acid molecule" as used herein means a deoxyribonucleic acid (DNA) molecule or ribonucleic acid (RNA) molecule. Both DNA and RNA molecules are constructed from nucleotides linked end to end, wherein each of the nucleotides contains a phosphate group, a sugar moiety, and either a purine or a pyrimidine base. Polynucleic acid molecules can be single or double-stranded polymers of nucleotides read from the 5' to the 3' end. Polynucleic acid molecules may also optionally contain synthetic, non-natural or altered nucleotide bases that permit correct read through by a polymerase and do not alter expression of a polypeptide encoded by that polynucleic acid molecule.

The term "an isolated polynucleic acid molecule" as used herein, means a polynucleic acid molecule that is no longer accompanied by some of materials with which it is associated in its natural state, or to a polynucleic acid molecule for which the structure of which is not identical to that of any naturally occurring polynucleic acid molecule. It is also contemplated by the inventors that the isolated polynucleic acid molecules of the present invention also include known types of modifications.

The term "nucleotide sequence" as used herein means the linear arrangement of nucleotides to form a polynucleotide of the sense and complementary strands of a polynucleic acid molecule either as individual single strands or in the duplex As used herein both terms "a coding sequence" and "a structural polynucleotide molecule" mean a polynucleotide molecule that is translated into a polypeptide, usually via mRNA, when placed under the control of appropriate regulatory molecules. The boundaries of the coding sequence are determined by a translation start codon at the 5'-terminus and a translation stop codon at the 3'-terminus. A coding sequence can include, but is not limited to, genomic DNA, cDNA, and recombinant polynucleotide sequences.

The term "recombinant DNAs" as used herein means DNAs that contains a genetically engineered modification through manipulation via mutagenesis, restriction enzymes, or other methods known in the art for manipulation of DNA molecules.

The term "synthetic DNAs" as used herein means DNAs assembled from oligonucleotide building blocks that are chemically synthesized using procedures known to those skilled in the art.

Both terms "polypeptide" and "protein", as used herein, mean a polymer composed of amino acids connected by peptide bonds. An amino acid unit in a polypeptide (or protein) is called a residue. The terms "polypeptide" and "protein" also apply to any amino acid polymers in which one or more amino acid residue is an artificial chemical analogue of a corresponding naturally occurring amino acid, as well as to any naturally occurring amino acid polymers. The essential nature of such analogues of naturally occurring amino acids is that, when incorporated into a polypeptide, that polypeptide is specifically reactive to antibodies elicited to the same polypeptide but consisting entirely of naturally occurring amino acids. It is well known in the art that proteins or polypeptides may undergo modification. Exemplary modifications are described in most basic texts, such as, for example, *Proteins—Structure and Molecular Properties*, 2nd ed., T. E. Creighton, W. H. Freeman and Company, New York (1993. Many detailed reviews are available on this subject, for example, those provided by Wold, F., Post-translational Protein Modifications. Perspectives and Prospects, pp. 1-12 in *Post-translational Covalent Modification of Proteins*, B. C. Johnson, Ed., Academic Press, New York (1983); Seifter et al., *Meth. Enzymol.* 182:626-M (1990) and Rattan et al., *Protein Synthesis: Post-translational Modifications and Aging*, Ann. New York Acad. Sci. 663:48-62 (1992).

The term "amino acid sequence" means the sequence of amino acids in a polypeptide (or protein) that is written starting with the amino-terminal (N-terminal) residue and ending with the carboxyl-terminal (C-terminal) residue.

"Percentage of sequence identity" is determined by comparing two optimally aligned sequences over a comparison window, wherein the portion of the polynucleotide or amino acid sequence in the comparison window may comprise additions or deletions (i.e., gaps) as compared to the reference sequence (that does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "substantially identical", "substantially homologous" and "substantial identity", used in reference to two polypeptide sequences or two polynucleotide sequences, mean that one polypeptide sequence or one polynucleotide sequence has at least 75% sequence identity compared to the other polypeptide sequence or polynucleotide sequence as a reference sequence using the Gap program in the WISCONSIN PACKAGE version 10.0-UNIX from Genetics Computer Group, Inc. based on the method of Needleman and Wunsch (J. Mol. Biol. 48:443-453, 1970) using the set of default parameters for pairwise comparison (for amino acid sequence comparison: Gap Creation Penalty=8, Gap Extension Penalty=2; for nucleotide sequence comparison: Gap Creation Penalty=50; Gap Extension Penalty=3) or using the TBLASTN program in the BLAST 2.2.1 software suite (Altschul et al., Nucleic Acids Res. 25:3389-3402), using BLOSUM62 matrix (Henikoff and Henikoff, Proc. Natl. Acad. Sci. U.S.A. 89:10915-10919, 1992) and the set of default parameters for pair-wise comparison (gap creation cost=11, gap extension cost=1.)

One aspect of the present invention provides an isolated polynucleic acid molecule comprising a nucleotide sequence or complement thereof, wherein the nucleotide sequence encodes a polypeptide from a crop plant having an amino acid sequence that has at least 75% sequence identity, or 80% sequence identity, or at least 85% or 90% sequence identity, or at least 95% sequence identity, or at least 98% sequence identity to a member selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, and SEQ ID NO: 51.

Polypeptides that are "substantially similar" share sequences as noted above except that residue positions that are not identical may differ by conservative amino acid changes. "Conservative amino acid changes" and "Conservative amino acid substitution" are used synonymously to describe the invention. Conservative amino acid substitutions refer to the interchangeability of residues having similar side chains. "Conservative amino acid substitutions" mean substitutions of one or more amino acids in a native amino acid sequence with another amino acid(s) having similar side chains, resulting in a silent change. Conserved substitutes for an amino acid within a native amino acid sequence can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine, valine-isoleucine, phenylalanine-tyrosine, lysine-arginine, alanine-valine, aspartic acid-glutamic acid, and asparagine-glutamine.

One skilled in the art will recognize that the values of the above substantial identity of nucleotide sequences can be appropriately adjusted to determine the corresponding sequence identity of two nucleotide sequences encoding the polypeptides of the present invention by taking into account codon degeneracy, conservative amino acid substitutions and reading frame positioning. Substantial identity of nucleotide sequences for these purposes normally means sequence identity of at least 75%.

The term "codon degeneracy" means divergence in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for ectopic expression in a host cell, it is desirable to design the gene such that its frequency of codon usage approaches the frequency of codon usage of the host cell as observed in a codon usage table.

The polynucleic acid molecules encoding a polypeptide of the present invention may be combined with other non-native, or "heterologous" sequences in a variety of ways. By "heterologous" sequences it is meant any sequence that is not naturally found joined to the nucleotide sequence encoding polypeptide of the present invention, including, for example, combinations of nucleotide sequences from the same plant that are not naturally found joined together, or the two sequences originate from two different species.

The term "operably linked", as used in reference to a regulatory molecule and a structural polynucleotide molecule, means that the regulatory molecule causes regulated expression of the operably linked structural polynucleotide molecule. "Expression" means the transcription and stable accumulation of sense or antisense RNA derived from the polynucleic acid molecule of the present invention. Expression may also refer to translation of mRNA into a polypeptide. "Sense RNA" means RNA transcript that includes the mRNA and so can be translated into polypeptide or protein by the cell. "Antisense RNA" means a RNA transcript that is complementary to all or part of a target primary transcript or complementary to mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-translated sequence, introns, or the coding sequence. "RNA transcript" means the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA.

The DNA construct of the present invention can, in one embodiment, contain a promoter which causes the over-expression of the polypeptide of the present invention, where "over-expression" means the expression of a polypeptide either not normally present in the host cell, or present in said host cell at a higher level than that normally expressed from the endogenous gene encoding said polypeptide. Promoters that can cause the over-expression of the polypeptide of the present invention are generally known in the art.

The DNA construct of the present invention can, in another embodiment, contain a promoter which causes the ectopic expression of the polypeptide of the invention, where "ectopic expression" means the expression of a polypeptide in a cell type other than a cell type in which the polypeptide is normally expressed; at a time other than a time at which the polypeptide is normally expressed; or at a expression level other than the level at which the polypeptide normally is expressed. Promoters that can cause ectopic expression of the polypeptide of the present invention are generally known in the art. The expression level or pattern of the promoter of the DNA construct of the present invention may be modified to enhance its expression. Methods known to those of skill in the art can be used to insert enhancing elements (for example, subdomains of the CaMV 35S promoter, Benfey et. al, 1990 EMBO J. 9: 1677-1684) into the 5' sequence of genes. In one embodiment, enhancing elements may be added to create a promoter that encompasses the temporal and spatial expression of the native promoter of the gene of the present invention but have altered levels of expression as compared to the native levels of expression. Similarly, tissue specific expression of the promoter can be accomplished through modifications of the 5' region of the promoter with elements determined to specifically activate or repress gene expression (for example, pollen specific elements, Eyal et al., 1995 Plant Cell 7: 373-384).

The term "a gene" means the segment of DNA that is involved in producing a polypeptide. Such segment of DNA includes regulatory molecules preceding (5' non-coding DNA molecules) and following (3' non-coding DNA molecules) the coding region, as well as intervening sequences (introns) between individual coding segments (exons). A "native gene" means a gene as found in nature with its own regulatory DNA sequences. "Chimeric gene" means any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" means a native gene in its natural location in the genome of an organism. A "foreign gene" means a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure resulting in a transgenic organism.

"Regulatory sequences" means polynucleotide molecules located upstream (5' non-coding sequences), within, or downstream (3' non-translated sequences) of a structural polynucleotide sequence, and that influence the transcription, RNA processing or stability, or translation of the associated structural polynucleotide sequence. Regulatory sequences may include promoters, translation leader sequences, introns, and polyadenylation recognition sequences.

The term promoter sequence or promoter means a polynucleotide molecule that is capable of causing expression of one or more genes when present in "cis" location of the structural polynucleotide capable of expressing polypeptide. Such promoter regions are typically found upstream of the trinucleotide, ATG, at the start site of a polypeptide coding region. Promoter molecules can also include DNA sequences from which transcription of transfer RNA (tRNA) or ribosomal RNA (rRNA) sequences are initiated. Transcription involves the synthesis of a RNA chain representing one strand of a DNA duplex which provides the template for its synthesis. Transcription takes place by the usual process of complementary base pairing, catalyzed and scrutinized by the enzyme RNA polymerase. The reaction can be divided into three stages described as initiation, elongation and termination. Initiation begins with the binding of RNA polymerase to the double stranded (DS or ds) DNA. The polynucleotide sequence of DNA required for the initiation reaction defines the promoter. The site at which the first nucleotide is incorporated is called the start-site or start-point of transcription. Elongation describes the phase during which the enzyme moves along the DNA and extends the growing RNA chain. Elongation involves the disruption of the DNA double stranded structure in which a transiently unwound region exists as a hybrid RNA-DNA duplex and a displaced single strand of DNA. Termination involves recognition of the point at which no further bases should be added to the chain. To terminate transcription, the formation of phosphodiester bonds must cease and the transcription complex must come apart. When the last base is added to the RNA chain, the RNA-DNA hybrid is disrupted, the DNA reforms into a duplex state, and the RNA polymerase enzyme and RNA molecule are both released from the DNA. The sequence of DNA required for the termination reaction is called the transcription termination region.

The promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions.

Promoters that are known or are found to cause transcription of DNA in plant cells can be used in the present invention. Such promoters may be obtained from a variety of sources such as plants and plant viruses. A number of promoters, including constitutive promoters, inducible promoters and tissue-specific promoters, that are active in plant cells have been described in the literature. It is preferred that the particular promoter selected should be capable of causing sufficient expression to result in the production of an effective amount of a polypeptide to cause the desired phenotype. In addition to promoters that are known to cause transcription of DNA in plant cells, other promoters may be identified for use in the current invention by screening a plant cDNA library for genes that are selectively or preferably expressed in the target tissues and then determine the promoter regions.

The term "constitutive promoter" means a regulatory sequence that causes expression of a structural nucleotide sequence in most cells or tissues at most times. Constitutive promoters are active under most environmental conditions and states of development or cell differentiation. A variety of constitutive promoters are well known in the art. Examples of constitutive promoters that are active in plant cells include but are not limited to the nopaline synthase (NOS) promoters; the cauliflower mosaic virus (P-CaMV) 19S and 35S (U.S. Pat. No. 5,858,642); the figwort mosaic virus promoter (P-FMV, U.S. Pat. No. 6,051,753); and actin promoters, such as the rice actin promoter (P-Os.Act1, U.S. Pat. No. 5,641,876).

The term "inducible promoter" means a regulatory sequence that causes conditional expression of a structural nucleotide sequence under the influence of changing environmental conditions (U.S. Pat. Nos. 5,922,564 and 5,965,791), or developmental conditions. The term "tissue-specific promoter" means a regulatory sequence that causes transcriptions or enhanced transcriptions of DNA in specific cells or tissues at specific times during plant development, such as in vegetative tissues or reproductive tissues. Examples of tissue-specific promoters under developmental control include promoters that initiate transcription only (or primarily only) in certain tissues, such as vegetative tissues, e.g., roots, leaves or stems, or reproductive tissues, such as fruit, ovules, seeds, pollen, pistils, flowers, or any embryonic tissue. Reproductive tissue specific promoters may be, e.g., ovule-specific, embryo-specific, endosperm-specific, integument-specific, seed coat-specific, pollen-specific, petal-specific, sepal-specific, or some combination thereof. One skilled in the art will recognize that a tissue-specific promoter may drive expression of operably linked DNA molecules in tissues other than the target tissue. Thus, as used herein a tissue-specific promoter is one that drives expression preferentially in the target tissue, but may also lead to some expression in other tissues as well.

A variety of promoters specifically active in vegetative tissues, such as leaves, stems, roots and tubers, can be used to express the polynucleic acid molecules of the present invention. Examples of tuber-specific promoters include, but are not limited to the class I and II patatin promoters (Bevan et al., EMBO J. 8:1899-1906, 1986; Koster-Topfer et al., Mol Gen Genet. 219:390-396, 1989; Mignery et al., Gene. 62:27-44, 1988; Jefferson et al., Plant Mol. Biol. 14: 995-1006, 1990). Examples of leaf-specific promoters include but are not limited to the ribulose biphosphate carboxylase (RBCS or RuBISCO) promoters (see, e.g., Matsuoka et al., Plant J. 6:311-319, 1994,); the light harvesting chlorophyll a/b binding protein gene promoter (see, e.g., Shiina et al., Plant Physiol. 115:477-483, 1997). Examples of root-specific promoters include, but are not limited to, the promoter for the acid chitinase gene (Samac et al., Plant Mol. Biol. 25:587-596, 1994); the root specific subdomains of the CaMV35S promoter that have been identified (Lam et al., Proc. Natl. Acad. Sci. (U.S.A.) 86:7890-7894, 1989).

Promoters derived from genes encoding embryonic storage proteins, which includes the gene encoding the 2S storage protein from *Brassica napus* (Dasgupta et al., Gene 133:301-302, 1993); the gene encoding oleosin 20kD from *Brassica napus* (GenBank No. M63985); the genes encoding oleosin A (GenBank No. U09118) and oleosin B (GenBank No. U09119) from soybean; the gene encoding oleosin 18kD from maize (GenBank No. J05212, Lee, Plant Mol. Biol. 26:1981-1987, 1994); and the gene encoding low molecular weight sulphur rich protein from soybean (Choi et al., Mol. Gen. Genet. 246:266-268, 1995), can also be used. Promoters derived from zein encoding genes (including the 15 kD, 16 kD, 19 kD, 22 kD, 27 kD, and gamma genes, Pedersen et al., Cell 29:1015-1026, 1982) can be also used. The zeins are a group of storage proteins found in maize endosperm.

It is recognized that additional promoters that may be utilized are described, for example, in U.S. Pat. Nos. 5,378,619, 5,391,725, 5,428,147, 5,447,858, 5,608,144, 5,608,144, 5,614,399, 5,633,441, 5,633,435, and 4,633,436, all of which are herein incorporated in their entirety. In addition, a tissue specific enhancer may be used (Fromm et al., The Plant Cell 1:977-984, 1989). It is further recognized that the exact boundaries of regulatory sequences may not be completely defined and DNA fragments of different lengths may have identical promoter activity.

The "translation leader sequence" means a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences include maize and petunia heat shock protein leaders, plant virus coat protein leaders, and plant rubisco gene leaders among others (Turner and Foster, Molecular Biotechnology 3:225, 1995).

The "3' non-translated sequences" or "3' termination region" means DNA sequences located downstream of a structural nucleotide sequence and include sequences encoding polyadenylation and other regulatory signals capable of affecting mRNA processing or gene expression. The polyadenylation signal functions in plants to cause the addition of polyadenylate nucleotides to the 3' end of the mRNA precursor. The polyadenylation sequence can be derived from the natural gene, from a variety of plant genes, or from T-DNA. An example of the polyadenylation sequence is the nopaline synthase 3' sequence (nos 3'; Fraley et al., Proc. Natl. Acad. Sci. USA 80: 4803-4807, 1983). Ingelbrecht et al. exemplify the use of different 3' non-translated sequences (Plant Cell 1:671-680, 1989).

The laboratory procedures in recombinant DNA technology used herein are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., Molecular Cloning—A Laboratory Manual, 2nd. ed., Cold Spring Harbor Laboratory, Cold Spring Harbor, N.Y. (1989), herein referred to as Sambrook et al., (1989).

A "substantial portion" of a polynucleotide sequence comprises enough of the sequence to afford specific identification and/or isolation of a polynucleic acid molecule comprising the sequence. Polynucleotide sequences can be evaluated either manually by one skilled in the art, or by using computer-based sequence comparison and identification tools that employ algorithms such as BLAST (Basic Local Alignment Search Tool; Altschul et al. J Mol. Biol. 215:403-410, 1993). In general, a sequence of thirty or more contiguous nucleotides is necessary in order to putatively identify a nucleotide sequence as homologous to a gene. Moreover, with respect to polynucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular polynucleic acid molecule comprising the primers. The skilled artisan having the benefit of the polynucleic acid molecules as reported herein, may now use all or a substantial portion of the disclosed sequences for purposes known to those skilled in this art. Accordingly, the instant invention comprises the complete polynucleotide sequences as reported in the accompanying Sequence Listing, as well as substantial portions of those sequences as defined above.

Isolation of polynucleic acid molecules encoding homologous polypeptides using polynucleotide sequence-dependent protocols is well known in the art. Examples of polynucleotide sequence-dependent protocols include, but are not limited to, methods of polynucleic acid molecule hybridization, and methods of DNA and RNA amplification as exemplified by various uses of polynucleic acid molecule amplification technologies (e.g., polymerase chain reaction, ligase chain reaction).

For example, structural polynucleic acid molecules encoding additional polypeptides of the present invention, either as cDNAs or genomic DNAs, could be isolated directly by using all or a substantial portion of the polynucleic acid molecules of the present invention as DNA hybridization probes to screen cDNA or genomic libraries from any desired plant employing methodology well known to those skilled in the art. Methods for forming such libraries are well known in the art. Specific oligonucleotide probes based upon the polynucleic acid molecules of the present invention can be designed and synthesized by methods known in the art. Moreover, the entire sequences of the polynucleic acid molecules can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the sequences. The resulting amplification products can be labeled directly during amplification reactions or labeled after amplification reactions, and used as probes to isolate full-length cDNA or genomic DNAs under conditions of appropriate stringency.

Alternatively, the polynucleic acid molecules of interest can be isolated from a mixture of polynucleic acid molecules using amplification techniques. For instance, the disclosed polynucleic acid molecules may be used to define a pair of primers that can be used with the polymerase chain reaction (Mullis, et al., Cold Spring Harbor Symp. Quant. Biol. 51:263-273, 1986; EP 50,424; EP 84,796, EP 258,017, EP 237,362, EP 201,184; U.S. Pat. No. 4,683,202; Erlich, U.S. Pat. No. 4,582,788, and U.S. Pat. No. 4,683,194) to amplify and obtain any desired polynucleic acid molecule directly from mRNA, from cDNA, from genomic libraries or cDNA libraries. PCR and other in vitro amplification methods may also be useful, for example, to clone nucleotide sequences that encode for polypeptides to be expressed, to make polynucleic acid molecules to use as probes for detecting the presence of the desired mRNA in samples, for nucleic acid sequencing, or for other purposes.

In addition, two short segments of the polynucleic acid molecules of the present invention may be used in polymerase chain reaction protocols to amplify longer polynucleic acid molecules encoding homologs of a polypeptide of the invention from DNA or RNA. For example, the skilled artisan can follow the RACE protocol (Frohman et al., Proc. Natl. Acad. Sci. USA 85:8998, 1988) to generate cDNAs by using PCR to amplify copies of the region between a single point in the transcript and the 3' or 5' end. Primers oriented in the 3' and 5' directions can be designed from the polynucleic acid molecules of the present invention. Using commercially available 3' RACE or 5' RACE systems (Gibco BRL, Life Technologies, Gaithersburg, Md. U.S.A.), specific 3' or 5' cDNA fragments can be isolated. Products generated by the 3' and 5' RACE procedures can be combined to generate full-length cDNAs (Frohman and Martin, Techniques 1:165, 1989).

Polynucleic acid molecules of interest may also be synthesized, either completely or in part, especially where it is desirable to provide modifications in the polynucleotide sequences, by well-known techniques as described in the technical literature, see, e.g., Carruthers et al., Cold Spring Harbor Symp. Quant. Biol. 47:411-418 (1982), and Adams et al., J. Am. Chem. Soc. 105:661 (1983).Thus, all or a portion of the polynucleic acid molecules of the present invention may be synthesized using a codon usage table of a selected plant host. Other modifications of the coding gene sequences may result in mutants having slightly altered activity.

After transgenic plants are obtained by one of the methods described above, it will be necessary to screen individual transgenic plants for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the polypeptide encoded by the gene being expressed. Alternatively, one could establish assays that specifically measure enzyme activity. A preferred method will be one that allows large numbers of samples to be processed rapidly, since it will be expected that a large number of transformants will be negative for the desired phenotype.

All or a substantial portion of the polynucleic acid molecules of the present invention may also be used as probes for genetically and physically mapping the genes that they are a part of, and as markers for traits linked to those genes. Such information may be useful in plant breeding in order to develop lines with desired phenotypes. For example, the polynucleic acid molecules of the present invention may be used as restriction fragment length polymorphism (RFLP) markers. Southern blots (Sambrook et al., 1989) of restriction-digested plant genomic DNA may be probed with the polynucleic acid fragments of the present invention. The resulting banding patterns may then be subjected to genetic analyses using computer programs such as MapMaker (Lander et al., Genomics 1: 174-181, 1987), in order to construct a genetic map. In addition, the polynucleic acid fragments of the present invention may be used to probe Southern blots containing restriction endonuclease-treated genomic DNAs of a set of individuals representing parent and progeny of a defined genetic cross. Segregation of the DNA polymorphisms is noted and used to calculate the position of the polynucleotide sequence of the present invention in the genetic map previously obtained using this population (Botstein et al., Am. J. Hum. Genet. 32:314-331, 1980).

The production and use of plant gene-derived probes for use in genetic mapping is described in Bernatzky and Tanksley (Plant Mol. Biol. Reporter 4:37-41, 1986). Numerous publications describe genetic mapping of specific cDNA clones using the methodology outlined above or variations thereof. For example, F2 intercross populations, backcross populations, randomly mated populations, near isogenic lines, exotic germplasms, and other sets of individuals may be used for mapping. Such methodologies are well known to those skilled in the art.

Polynucleic acid probes derived from the polynucleic acid molecules of the present invention may also be used for physical mapping (i.e., placement of sequences on physical maps; see Hoheisel et al., In: *Non-mammalian Genomic Analysis: A Practical Guide*, Academic press 1996, pp. 319-346).

In another embodiment, polynucleic acid probes derived from the polynucleic acid molecules of the present invention may be used in direct fluorescence in situ hybridization (FISH) mapping (Trask, Trends Genet. 7:149-154, 1991). Although current methods of FISH mapping favor use of large clones (several to several hundred kilobases; see Laan et al., Genome Res. 5:13-20, 1995), improvements in sensitivity may allow performance of FISH mapping using shorter probes.

A variety of polynucleic acid amplification-based methods of genetic and physical mapping may be carried out using the nucleotide molecules of the present invention. Examples include allele-specific amplification (Kazazian et al., J. Lab. Clin. Med. 11:95-96, 1989), polymorphism of PCR-amplified fragments (CAPS; Sheffield et al., Genomics 16:325-332, 1993), allele-specific ligation (Landegren et al., Science 241:1077-1080, 1988), nucleotide extension reactions (Sokolov et al., Nucleic Acid Res. 18:3671, 1990), Radiation Hybrid Mapping (Walter et al., Nat. Genet. 7:22-28, 1997) and Happy Mapping (Dear and Cook, Nucleic Acid Res. 17:6795-6807, 1989). For these methods, the sequence of a polynucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the nucleotide sequence. However, this identification is generally not necessary for mapping methods.

Isolated polynucleic acid molecules of the present invention may find use in the identification of loss of function mutant phenotypes of a plant, due to a mutation in one or more endogenous genes encoding polypeptides of the present invention. This can be accomplished either by using targeted gene disruption protocols or by identifying specific mutants for these genes contained in a population of plants carrying mutations in all possible genes (Ballinger and Benzer, Proc. Natl. Acad Sci USA 86:9402-9406, 1989; Koes et al., Proc. Natl. Acad. Sci. USA 92:8149-8153, 1995; Bensen et al., Plant Cell 7:75-84, 1995). The latter approach may be accomplished in two ways. First, short segments of the polynucleic acid molecules of the present invention may be used in polymerase chain reaction protocols in conjunction with a mutation tag sequence primer on DNAs prepared from a population of plants in which mutator transposons or some other mutation-causing DNA element has been introduced. The amplification of a specific DNA fragment with these primers indicates the insertion of the mutation tag element in or near the plant gene encoding polypeptides. Alternatively, the polynucleic acid molecules of the present invention may be used as a hybridization probe against PCR amplification products generated from the mutation population using the mutation tag sequence primer in conjunction with an arbitrary genomic site primer, such as that for a restriction enzyme site-anchored synthetic adapter.

The polypeptides of the present invention may also include fusion polypeptides. A polypeptide that comprises one or more additional polypeptide regions not derived from that polypeptide is a "fusion" polypeptide. Such molecules may be derivatized to contain carbohydrate or other moieties (such as keyhole, limpet, hemocyanin, etc.). Fusion polypeptides of the present invention are preferably produced via recombinant means.

The polypeptide molecules of the present invention may also include polypeptides encoded by all or a substantial portion of polypeptide-encoding sequences set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, and SEQ ID NO: 51 or complements thereof or, fragments or fusions thereof in which conservative, non-essential, or not relevant, amino acid residues have been added, replaced, or deleted. An example of such a homolog is the homolog polypeptide (or protein) from different species. Such a homolog can be obtained by any of a variety of methods. For example, as indicated above, one or more of the disclosed sequences, all or a substantial portion of a polypeptide-encoding sequences selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, and SEQ ID NO: 50 and complements thereof will be used to define a pair of primers that may be used to isolate the homolog encoding polynucleic acid molecules from any desired species. Such molecules can be expressed to yield homologs by recombinant means.

Polynucleic acid molecules that encode all or part of the polypeptides of the present invention can be expressed, via recombinant means, to yield polypeptides that can in turn be used to elicit antibodies that are capable of binding the expressed polypeptides. It may be desirable to derivatize the obtained antibodies, for example with a ligand group (such as biotin) or a detectable marker group (such as a fluorescent group, a radioisotope or an enzyme). Such antibodies may be used in immunoassays for that polypeptide. In a preferred embodiment, such antibodies can be used to screen cDNA expression libraries to isolate full-length cDNA clones of the present invention (Lemer, Adv. Immunol. 36:1, 1984; Sambrook et al., 1989).

Plant Recombinant DNA Constructs and Transformed Plants

The isolated polynucleic acid molecules of the present invention can find particular use in creating transgenic crop plants in which polypeptides of the present invention are overexpressed. Overexpression of these polypeptides in a plant can enhance plant stress tolerance and thereby lead to improvement in the yield of the plant. It will be particularly desirable to enhance plant drought and osmotic stress tolerance in crop plants that undergo such stresses over the course of a normal growing season. Crop plants are defined as plants which are cultivated to produce one or more commercial products. Examples of such crops or crop plants include soybean, canola, rape, cotton (cottonseeds), sunflower, and grains such as corn, wheat, rice, rye, and the like.

The term "transgenic crop plant" means a plant that contains an exogenous polynucleic acid, which can be derived from the same plant species or from a different species. By "exogenous" it is meant that a polynucleic acid molecule originates from outside the plant into which the polynucleic acid molecule is introduced. An exogenous polynucleic acid molecule can have a naturally occurring or non-naturally occurring nucleotide sequence. One skilled in the art understands that an exogenous polynucleic acid molecule can be a heterologous polynucleic acid molecule derived from a different plant species than the plant into which the polynucleic acid molecule is introduced or can be a polynucleic acid molecule derived from the same plant species as the plant into which it is introduced.

Crop plant cell, as used herein, includes without limitation, seeds, suspension cultures, embryos, meristematic regions, callus tissue, leaves, roots, shoots, gametophytes, sporophytes, pollen and microspores.

The term "genome" as it applies to plant cells encompasses not only chromosomal DNA found within the nucleus, but organelle DNA found within subcellular components of the cell. DNAs of the present invention introduced into plant cells can therefore be either chromosomally integrated or organelle-localized. The term "genome" as it applies to bacteria encompasses both the chromosome and plasmids within a bacterial host cell. Encoding DNAs of the present invention introduced into bacterial or microbial host cells can therefore be either chromosomally integrated or plasmid-localized.

Exogenous polynucleic acid molecules may be transferred into a crop plant cell by the use of a recombinant DNA construct (or vector) designed for such a purpose. The present invention also provides a plant recombinant DNA construct (or vector) for producing transgenic crop plants, wherein the plant recombinant DNA construct comprises a structural nucleotide sequence encoding an polypeptide of the present invention. Methods that are well known to those skilled in the art may be used to prepare the crop plant recombinant DNA construct (or vector) of the present invention. These methods include in vitro recombinant DNA techniques, synthetic techniques, and in vivo genetic recombination. Such techniques are described in Sambrook et al., (1989). The GATEWAY™ cloning technology (Invitrogen Life Technologies, Carlsbad, Calif.) is also used for construction of a few vectors of the invention. GATEWAY™ technology uses phage lambda base site-specific recombination for vector construction, instead of restriction endonucleases and ligases. Using the GATEWAY™ cloning technology, a desired DNA sequence, such as a coding sequence, may be amplified by PCR with the phage lambda attB1 sequence added to the 5' primer and the attB2 sequence added to the 3' primer. Alternatively, nested primers comprising a set of attB1 and attB2 specific primers and a second set of primers specific for the selected DNA sequence can be used. Sequences, such as coding sequences, flanked by attB1 and attB2 sequences can be readily inserted into plant expression vectors using GATEWAY™ methods. Assembly of DNA constructs are done by standard molecular biology techniques as described in Sambrooks et al.

A plant recombinant DNA construct of the present invention contains a structural nucleotide sequence encoding a polypeptide of the present invention and operably linked to regulatory sequences. Exemplary regulatory sequences include but are not limited to promoters, translation leader sequences, introns and 3' non-translated sequences. The promoters can be constitutive, inducible, native, or tissue-specific promoters.

A plant recombinant DNA construct of the present invention will typically comprise a selectable marker that confers a selectable phenotype on plant cells. Selectable markers may also be used to select for plants or plant cells that contain the exogenous polynucleic acid molecules encoding polypeptides of the present invention. The marker may encode biocide resistance, antibiotic resistance (e.g, kanamycin, G418, bleomycin, hygromycin, etc.), or herbicide resistance (e.g., glyphosate, glufosinate, etc.). Examples of selectable markers include, but are not limited to, a neo gene (Potrykus et al., Mol. Gen. Genet. 199:183-188 (1985) that codes for kanamycin resistance and can be selected for using kanamycin, G418, etc.; a bar gene that codes for bialaphos resistance; a mutant EPSP synthase gene (Hinchee et al., Bio/Technology 6:915-922 (1988)) that encodes glyphosate resistance; a nitrilase gene that confers resistance to bromoxynil (Stalker et al., J. Biol. Chem. 263:6310-6314 (1988) a mutant acetolactate synthase gene (ALS) that confers imidazolinone or sulphonylurea resistance, and a methotrexate resistant DHFR gene (Thillet et al., J. Biol. Chem. 263:12500-12508 (1988)).

A plant recombinant DNA construct of the present invention may also include a screenable marker. Screenable markers may be used to monitor expression. Exemplary screenable markers include a β-glucuronidase or uidA gene (GUS: 1) that encodes an enzyme for which various chromogenic substrates are known (Jefferson, Plant Mol. Biol, Rep. 5:387-405 (1987)); an R-locus gene that encodes a product that regulates the production of anthocyanin pigments (red color) in plant tissues (Dellaporta et al., Stadler Symposium 11:263-282 (1988)); a p-lactamase gene (Sutcliffe et al., Proc. Natl. Acad. Sci. (U.S.A.) 75:3737-3741 (1978)), a gene that encodes an enzyme for which various chromogenic substrates are known (e.g., PADAC, a chromogenic cephalosporin); a luciferase gene (Ow et al., Science 234:856-859 (1986)); a xylE gene (Zukowsky et al., Proc. Natl. Acad. Sci. (U.S.A.) 80:1101-1105 (1983)) that encodes a catechol dioxygenase that can convert chromogenic catechols; an a-amylase gene (Ikatu et al., Bio/Technol. 8:241-242 (1990)); a tyrosinase gene (Katz et al., J. Gen. Microbiol. 129:2703-2714 (1983)) that encodes an enzyme capable of oxidizing tyrosine to DOPA and dopaquinone that in turn condenses to melanin; and an a-galactosidase that will turn over a chromogenic a-galactose substrate.

Included within the terms "selectable or screenable marker genes" are also genes that encode a secretable marker whose secretion can be detected as a means of identifying or selecting for transformed cells. Examples include markers that encode a secretable antigen that can be identified by antibody interaction, or even secretable enzymes that can be detected catalytically. Secretable proteins fall into a number of classes, including small, diffusible proteins detectable, e.g., by ELISA, small active enzymes detectable in extracellular solution (e.g., a-amylase, p-lactamase, phosphinothricin transferase), or proteins that are inserted or trapped in the cell wall (such as proteins that include a leader sequence such as that found in the expression unit of extension or tobacco PR-S). Other possible selectable and/or screenable marker genes will be apparent to those of skill in the art.

In addition to a selectable marker, it may be desirable to use a reporter gene. In some instances a reporter gene may be used with or without a selectable marker. Reporter genes are genes that are typically not present in the recipient organism or tissue and typically encode for proteins resulting in some phenotypic change or enzymatic property. Examples of such genes are provided in K. Wising et al. Ann. Rev. Genetics, 22, 421 (1988). Preferred reporter genes include the beta-glucuronidase (GUS) of the uidA locus of *E. coli*, the chloramphenicol acetyl transferase gene from Tn9 of *E. coli*, the green fluorescent protein from the bioluminescent jellyfish *Aequorea Victoria*, and the luciferase genes from firefly *Photinus pyralis*. An assay for detecting reporter gene expression may then be performed at a suitable time after said gene has been introduced into recipient cells. A preferred such assay entails the use of the gene encoding beta-glucuronidase (GUS) of the uidA locus of *E. coli* as described by Jefferson et al., (Biochem. Soc. Trans. 15, 17-19 (1987) to identify transformed cells, referred to herein as GUS:1.

In preparing the recombinant DNA constructs (vectors) of the present invention, the various components of the construct or fragments thereof will normally be inserted into a convenient cloning vector, e.g., a plasmid that is capable of replication in a bacterial host, e.g., *E. coli*. Numerous cloning vectors exist that have been described in the literature, many of which are commercially available. After each cloning, the cloning vector with the desired insert may be isolated and subjected to further manipulation, such as restriction digestion, insertion of new fragments or nucleotides, ligation, deletion, mutation, resection, etc. so as to tailor the components of the desired sequence. Once the construct has been completed, it may then be transferred to an appropriate vector for further manipulation in accordance with the manner of transformation of the host cell.

The present invention also provides a transgenic plant comprising in its genome an isolated polynucleic acid that comprises: (a) a 5' non-coding sequence that functions in the cell to cause the production of a mRNA molecule; that is operably linked to (b) a structural polynucleotide sequence encoding a polypeptide of this invention that is operably linked to (c) a 3' non-translated sequence that functions in said cell to cause termination of transcription. Preferably, the amino acid sequence of the polypeptide has at least 75% sequence identity, about 85% sequence identity, or about 95% or about 98% sequence identity to a member selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, and SEQ ID NO: 51. The polypeptide can also have one of the sequences set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, and SEQ ID NO: 51 with conservative amino acid substitutions.

Transgenic crop plants of the present invention have incorporated into their genome, or transformed into their chloroplast or plastid genomes, an exogenous polynucleic acid molecule that comprises at least a structural nucleotide sequence that encodes a polypeptide having an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, and SEQ ID NO: 51. Transgenic crop plants are also meant to comprise progeny (descendant, offspring, etc.) of any generation of such a transgenic plant. A seed of any generation of all such transgenic crop plants wherein said seed comprises a DNA sequence encoding the polypeptide of the present invention is also an important aspect of the invention.

In one embodiment, the transgenic crop plants of the present invention will have enhanced tolerance to environmental stress due to the expression of an exogenous polynucleic acid molecule encoding a polypeptide of the present invention. The transgenic crop plants of the present invention will have tolerance to abiotic stresses, for example, variations from optimal condition to sub-optimal conditions for water, humidity, temperature, light or other radiations, organic and inorganic nutrients, and salinity. "Cold" is defined as sub-optimal thermal conditions needed for normal growth of natural plants. As used herein, "cold germination" is germination occurring at temperatures below (two or more degrees Celsius below) those normal for a particular species or particular strain of plant. As used herein, "cold tolerance" is defined as the ability of a plant to continue growth for a significant period of time after being placed at a temperature below that normally encountered by a plant of that species at that growth stage. As used herein "enhanced" is defined as to increase or improve in value, quality, desirability, or attractiveness of one or more desired traits in a transgenic plant as compared to a nontransgenic plant of comparable variety. The transgenic plants of the present invention will have higher tolerance to cold, higher germination in cold temperature and a higher yield of agricultural products under stressed conditions. Similarly "water stress" is defined as a sub-optimal amount of water needed for normal growth of natural plants. As used herein "water-stress" is a plant condition characterized by water potential in a plant tissue of less than about −0.5 megapascals (MPa). Water potential in maize is conveniently measured by clamping a leaf segment in a pressurizable container so that a cut cross section of leaf is open to atmospheric pressure. Gauge pressure (above atmospheric pressure) on the contained leaf section is increased until water begins to exude from the atmospheric-pressure-exposed cross section. The gauge pressure at incipient water exudation is reported as negative water potential in the plant tissue. The transgenic plants of the present invention will have a higher tolerance to water stress as compared to natural plants of same species and will have a higher yield of agricultural products under water stressed conditions.

The DNA construct of the present invention may be introduced into the genome of a desired plant host by a variety of conventional transformation techniques that are well known to those skilled in the art. Methods of transformation of plant cells or tissues include, but are not limited to the *Agrobacterium* mediated transformation method and the *Biolistics* or particle-gun mediated transformation method. Suitable plant transformation vectors for the purpose of *Agrobacterium* mediated transformation include those derived from a Ti plasmid of *Agrobacterium tumefaciens*, as well as those disclosed, e.g., by Herrera-Estrella et al., Nature 303:209 (1983); Bevan, Nucleic Acids Res. 12: 8711-8721 (1984); Klee et al., Bio-Technology 3(7): 637-642 (1985); and EP 120,516. In addition to plant transformation vectors derived from the Ti or root-inducing (Ri) plasmids of *Agrobacterium*, alternative methods can be used to insert the DNA constructs of this invention into plant cells. Such methods may involve, but are not limited to, for example, the use of liposomes, electroporation, chemicals that increase free DNA uptake, free DNA delivery via microprojectile bombardment, and transformation using viruses or pollen.

A plasmid expression vector suitable for the introduction of a polynucleic acid encoding a polypeptide of present invention in monocots using electroporation or particle-gun mediated transformation is composed of the following: a promoter that is constitutive or tissue-specific; an intron that provides a splice site to facilitate expression of the gene, such as the maize Hsp70 intron (U.S. Pat. No. 5,593,874, herein incorporated by reference in its entirety); and a 3' polyadenylation sequence such as the nopaline synthase 3' sequence (nos 3'; Fraley et al., Proc. Natl. Acad. Sci. USA 80: 4803-4807, 1983). This expression cassette may be assembled on high copy replicons suitable for the production of large quantities of DNA.

An example of a useful Ti plasmid cassette vector for plant transformation is pMON17227. This vector is described in U.S. Pat. No. 5,633,435, herein incorporated by reference in its entirety, and contains a gene encoding an EPSPS enzyme with glyphosate resistance (herein referred to as aroA:CP4), that is an excellent selection marker gene for many plants. The gene is fused to the *Arabidopsis* EPSPS chloroplast transit peptide (At. EPSPS:CTP2) and expressed from the Figwort mosaic virus (P-FMV) promoter as described therein.

When adequate numbers of cells containing the exogenous polynucleic acid molecule encoding polypeptides from the present invention are obtained, the cells can be cultured, then regenerated into whole plants. Such regeneration techniques rely on manipulation of certain phytohormones in a tissue culture growth medium, typically relying on a biocide and/or herbicide marker that has been introduced together with the desired nucleotide sequences. Regeneration techniques are described generally in Klee et al., Ann. Rev. Plant Phys. 38:467-486 (1987).

The development or regeneration of transgenic crop plants containing the exogenous polynucleic acid molecule that encodes a polypeptide of interest is well known in the art. Preferably, the regenerated plants are self-pollinated to provide homozygous transgenic crop plants, as discussed above. Otherwise, pollen obtained from the regenerated plants is crossed to seed-grown plants of agronomically important lines. Conversely, pollen from plants of these important lines is used to pollinate regenerated plants.

Plants that can be made to have enhanced stress tolerance by practice of the present invention include, but are not limited to, Acacia, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, cauliflower, celery, cherry, cilantro, citrus, clementines, coffee, corn, cotton, cucumber, Douglas fir, eggplant, endive, escarole, eucalyptus, fennel, figs, forest trees, gourd, grape, grapefruit, honey dew, jicama, kiwifruit, lettuce, leeks, lemon, lime, Loblolly pine, mango, melon, mushroom, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, turf, a vine, watermelon, wheat, yams, and zucchini.

The following examples are provided to better elucidate the practice of the present invention and should not be interpreted in any way to limit the scope of the present invention. Those skilled in the art will recognize that various modifications, additions, substitutions, truncations, etc., can be made to the methods and genes described herein while not departing from the spirit and scope of the present invention.

EXAMPLES

Example 1

Stock Rice Plants and Growth Conditions

Rice seeds (Oryza sativa, "Kasalath" cultivar) were obtained from the National Institute of Agrobiological Resources MAFF1-2Kannondai2-Chome, Tsukuba Ibrai-3058602 Japan. For increasing the stock size of initial seeds, seeds were planted to raise seedling and seedlings were subsequently transplanted in 6 inch (6") pots for obtaining mature plants bearing panicles and mature seeds.

Seed Propagation

For obtaining mature seeds, rice plants, plant organs or immature embryos at the desired developmental stage, approximately 100 seeds of each variety were soaked in distilled water for 30 to 60 minutes at room temperature. During the soaking period floating chaff and impurities from the seeds were removed, water was decanted and the seeds were placed in properly labeled pre-irrigated 6" pots filled with red soil. After placing 1-2 seed(s)/pot on top of the soil, the seeds were covered with fine sand and then gently patted. Each seeded pot was covered with newspaper and was irrigated regularly with rose-can tin in order to maintain humidity in the soil. After 4-6 days, paper covers from the pots were removed, exposing germinated seeds to the light. The germinated seeds were allowed to grow 1"-2" in height which usually occurred 7-8 days after planting seeds. Pots were then transferred to a water tray for proper water and nutrient treatments. Initial fertilizer was prepared by mixing 10 grams (gm) urea, 30 gm of 17:17:17 N:P:K fertilizer, 2.5 gm of Multiplex -a micro nutrient (Karnataka Agro chemicals, Bangalore, India), 0.25 gm of $FeSO_4$ in one liter of water and adjusting the pH to 6.2. Approximately 1 liter of this solution was used to fertilize pots placed on 1 square meter of water trays. Water level was maintained in trays with potted seedlings. Seedlings were allowed to grow for 20 days under natural sunlight (400-800µ mole/m$^2$/sec)/10-12 hr day. Day temperature was observed at 28° C.-30° C., night temperature at 19° C.-20° C. with a relative humidity of 60-70% in the greenhouses.

Transplanting of Rice Seedlings

For transplanting rice seedlings to generate mature plants, a red and black soil mixture was used as potting mix in 6" pots. Red and black soils were mixed in 3:1 ratio to bring soil pH between pH 6 and pH 7. Ten grams of farm yard manure, (Varsha Agro. Industries, Bangalore, India, from now on referred to as FYM ) was added per 0.003 cubic meter of soil (which is roughly equivalent to a full 6" pot soil). This mixture of soil was used to fill 6" pots for transplanting. Potted soil was saturated with water and then allowed to drain before packing the soil to the desired density. Then soil in the pot was drenched with the fungicide "Carbendzim" at the concentration of 1 gm/L (Carbendzim, 50% WP, BASF India Ltd. Mumbai) and the insecticide Monocrotophos (Monocrotophos 36% SL , Bayer India Ltd, Mumbai India) 1 ml/L for disinfection. During or prior to the disinfection procedure, all clumps of soil in pot were eliminated to maximize the treatment.

For transplanting, entire growing rice seedlings along with the old soil were carefully removed from the pots. Excess soil from the seedlings was removed by gentle tapping. Two seedlings were planted (3-6 cm deep) in pots with new soil mix. For the first 10 days approximately 1" water level followed by 2" water level was maintained until 10 days before harvesting. Before harvesting ripe panicles with seed, water was siphoned out of the trays. Siphoning was done by draining all the water from the tray on the 30$^{th}$ day of heading and 10 days before harvesting. Fertilizer application for growing rice was done as per the following table:

used as the template to synthesize rice cDNA molecules by using a RT-PCR kit manufactured by Life Technologies as per the instrctions of manufacturer of the kit. This cDNA was used as template DNA in a PCR reaction to amplify cDNA molecules which were purified on a low melting agarose gel by electrophoresis as described by Sambrook et al. Purified cDNA molecules of Seq ID NO: 1 were cloned in pCRTOPO 2.1 vector as per the manufacturer's instructions (Invitrogen, Carlsbad, Calif. 92008). After confirming the sequence, cloned molecules were excised and re-cloned in the publicly available rice binary expression vector pCAMBIA 1300 (CAMBIA, Canberra, Australia) to generate rice transforming vector molecules. Restriction analysis was performed to identify the transforming vector with SEQ ID NO: 1 in proper orientation which would encode polypeptide molecules as shown in SEQ ID NO 2.

Example 3

Identification of Homologs, Paralogs or Orthologs:

This example explains how to isolate homologs, orthologs, or paralogs of SEQ ID NO: 1 by generating cDNA libraries, sequencing cDNA clones to generate a database for identification of desired clones from desired plant species.

TABLE 1

Composition of Different plant growth medium used for growing rice plants and seedlings.

| Fertilizers | Micro Nutrient (Multiplex) | N | P | K | 17:17:17 | Urea | S. Phosphate | M. Potash | Application Time |
|---|---|---|---|---|---|---|---|---|---|
| Total Doses gm/m$^2$ | | 15 | 5 | 7.5 | | | | | |
| Basal Doses gm/m$^2$ | 2.5 | 2.5 | 5 | 2.5 | 14.71 | | 11.90 | 0 | DOP + 1 = A |
| gm/m$^2$ | 2.5 | 2.5 | | | 14.71 | | | | A + 15 = B |
| Doses at Active Tillering gm/m$^2$ | 2.5 | 2.5 | | 2.5 | | 5.4 | | 4.17 | B + 15 = C |
| gm/m$^2$ | 2.5 | 2.5 | | 2.5 | | 5.4 | | 4.17 | C + 15 = D |
| Doses at Panicle Initiation Stage gm/m$^2$ | 2.5 | 2.5 | | | | 5.4 | | 4.17 | D + 15 = E |
| Doses at Heading gm/m$^2$ | 2.5 | 2.5 | | | | 5.4 | | | E + 15 |

Table legend:
Micro Nutrient (Multiplex - (Karnataka Agro chemicals, Bangalore, India),.
N, P, K (Nitrogen, P$_2$O$_5$, K$_2$O in the form of complex fertilizer 17:17:17 Madras Fertilizers Ltd, Chennai).
Superphosphate. Phosphate(P$_2$O$_5$ 16%, EID Parry India Ltd, Chennai India),
Muriate of Potash (K$_2$O 60% Zuari Agro industries, Goa, India)
Date of sowing (DOS).
Date of transplanting (DOP).

Seeds from transgenic or non-transgenic rice plants were kept segregated from the time of harvest until next use as per standard practices well know in the art.

Example 2

This example demonstrates how rice OsPK7 was cloned to express in rice plants. OsPK7 cDNA specific primers were designed based on the gene sequences as shown in SEQ ID NO: 1. DNASTAR software ( DNASTAR, Inc. Madison, Wis., USA) was used for primer design. The sequences of the 5' and 3' primer were SEQ ID NO: 48 and SEQ ID NO: 49 respectively. Total RNA was purified from pooled rice (var. Nipponbare) coleoptile tissue by using Trizol reagent from Life Technologies (Gibco BRL, Life Technologies, Gaithersburg, Md. U.S.A. from now on referred to as Gibco), essentially as recommended by the manufacturer. Total RNA was For construction of cDNA libraries from plants, plant tissues are harvested and immediately frozen in liquid nitrogen and stored at −80° C. until total RNA extraction. Total RNA is purified from tissues using Trizol reagent from Life Technologies (Gibco BRL, Life Technologies, Gaithersburg, Md. U.S.A.), essentially as recommended by the manufacturer. Poly A+ RNA (mRNA) is purified using magnetic oligo dT beads essentially as recommended by the manufacturer (Dynabeads, Dynal Corporation, Lake Success, New York U.S.A.).

Construction of plant cDNA libraries is well known in the art and a number of cloning strategies exist. A number of cDNA library construction kits are commercially available. The Superscript™ Plasmid System for cDNA synthesis and Plasmid Cloning (Gibco BRL, Life Technologies, Gaithersburg, Md. U.S.A.) is used, following the conditions suggested by the manufacturer.

The cDNA libraries are plated on LB agar containing the appropriate antibiotics for selection and incubated at 37° for sufficient time to allow the growth of individual colonies. Single selective-media colonies are individually placed in each well of 96-well microtiter plates containing LB liquid including the selective antibiotics. The plates are incubated overnight at approximately 37° C. with gentle shaking to promote growth of the cultures.

The plasmid DNA is isolated from each clone using Qiaprep plasmid isolation kits, using the conditions recommended by the manufacturer (Qiagen Inc., Santa Clara, Calif. U.S.A.).

The template plasmid DNA clones are used for subsequent sequencing. For sequencing the cDNA libraries, a commercially available sequencing kit, such as the ABI PRISM dRhodamine Terminator Cycle Sequencing Ready Reaction Kit with AmpliTaq® DNA Polymerase, FS, is used under the conditions recommended by the manufacturer (PE Applied Biosystems, Foster City, Calif.). The cDNAs of the present invention are generated by sequencing initiated from the 5' end or 3' end of each cDNA clone. Entire inserts or only part of the inserts (ESTs or expressed sequenced tags) are sequenced.

A number of DNA sequencing techniques are known in the art, including fluorescence-based sequencing methodologies. These methods have the detection, automation and instrumentation capability necessary for the analysis of large volumes of sequence data. Currently, the 377 and 3700 DNA Sequencer (Perkin-Elmer Corp., Applied Biosystems Div., Foster City, Calif.) allow the most rapid electrophoresis and data collection. With these types of automated systems, fluorescent dye-labeled sequence reaction products are detected and data are entered directly into the computer, producing a chromatogram that is subsequently viewed, stored, and analyzed using the corresponding software programs. These methods are known to those of skill in the art and have been described and reviewed (Birren et al., Genome Analysis: Analyzing DNA, 1, Cold Spring Harbor, N.Y.).

The generated ESTs (including any full-length cDNA inserts or complete coding sequences) are combined with ESTs and full-length cDNA sequences in public databases such as GenBank. Duplicate sequences are removed, and duplicate sequence identification numbers are replaced. The combined dataset is then clustered and assembled using Pangea Systems (DoubleTwist, 2001 Broadway, Oakland, Calif. 94612) tool identified as CAT v.3.2. First, the EST sequences are screened and filtered, e.g. high frequency words are masked to prevent spurious clustering; sequence common to known contaminants such as cloning bacteria are masked; high frequency repeated sequences and simple sequences are masked; unmasked sequences of less than 100 base pairs are eliminated. The thus-screened and filtered ESTs are combined and subjected to a word-based clustering algorithm that calculates sequence pair distances based on word frequencies and uses a single linkage method to group like sequences into clusters of more than one sequence, as appropriate. Clustered sequences are assembled individually using an iterative method based on PHRAP/CRAWIMAP providing one or more self-consistent consensus sequences and inconsistent singleton sequences. The assembled clustered sequence files are checked for completeness and parsed to create data representing each consensus contiguous sequence (contig), the initial EST sequences, and the relative position of each EST in a respective contig. The sequence of the 5' most clone is identified from each contig. The initial sequences that are not included in a contig are separated out.

Above described databases with nucleotide and peptide sequences are queried with sequences of present invention to get the following homologs, orthologs or paralogs as shown in Table 2. The BLAST 2.2.1 software (Altschul, et.al., Nucleic Acids Res. 25: 3389-3402 (1997), with BLOSUM62 matrix and "no Filter" options, is used in the queries. When necessary, frame-shifts in the DNA sequences of the homologs are detected by aligning the DNA sequence of the homolog in question to the protein sequence of present invention, using the "frame+_n2p" program with default parameters in the GenCore software package (Compugen Inc., 25 Leek Crescent, Richmond Hill, Ontario, L4B 4B3, Canada, 1998). Such frame-shifts are conceptually corrected to yield open reading frames. The "translate" program with default parameters in the same package is used to translate open reading frames to corresponding peptide sequences based on standard genetic codes.

TABLE 2

Description of homologs, orthologs or paralogs of SEQ ID NO: 1

| SEQ ID NO | Genus species |
| --- | --- |
| 1 to 6 | Oryza sativa |
| 7 to 14 | Zea mays |
| 15 to 20 | Glycine max |
| 21 and 22 | Gossypium hirsutum |
| 23 to 27 | Triticum aestivum |
| 28 and 29 | Hordeum vulgare |
| 30 to 33 | Allium porrum |
| 34 and 35 | Brassica napus |
| 36 and 37 | Pisum sativum |
| 38 and 39 | Medicago truncatula |
| 40 to 47 | Arabidopsis thaliana |

Example 4

Isolation of Polynucleotide Molecules of the Present Invention and Their Modification For isolating polynucleotide molecules of the present invention, total RNA is isolated from the appropriate crop and other desired plant species by pooling tissues of different developmental stages of all vegetative and reproductive organs. RNA is prepared from pooled plant tissue by the Trizol method (Gibco BRL, Life Technologies, Gaithersburg, Md. U.S.A.) essentially as recommended by the manufacturer. Sequences are amplified out from total RNA by using the Superscript II kit (Gibco BRL, Life Technologies, Gaithersburg, Md. U.S.A.) according to the manufacturer's directions. Design of appropriate PCR primers for isolating sequences of present invention is based on the sequence information provided in the sequence listing of this disclosure. Design of primers and reaction conditions are determined as described in the art. (PCR Strategies, Edited by Michael A. Innis; David H. Gelfand; & Johm J. Sninsky; Academic Press 1995 and PCR Protocols, A Guide to Method and Applications, Edited by Michael A. Innis; David H. Gelfand; Johm J. Sninsky; & Thomas J. White Academic Press 1990). All reagents for isolating sequences of the invention can be procured from Gibco BRL, Life Technologies, Gaithersburg, Md. U.S.A.

Example 5

This example explains transformation of rice plants to generate plants of the present invention.

Transgenic rice plants were produced by an *Agrobacterium* mediated transformation method. A disarmed *Agrobacterium* strain C58 (EHA105) harboring the plant transformation construct was produced by the standard electroporation method (Bio-Rad) of transforming bacteria. Transformed bacterial cells were grown overnight in LB medium (Gibco) containing 5 gm/L hygromycin at 25° C., centrifuged and suspended in Co-cultivation medium (Table 3 shown as CC1 medium)

supplemented with acetosyringone (100 uM) at an $OD_{600}$ of 1. This suspension was used for transforming rice tissue.

Tissue Preparation for Rice Transformation:

Panicles of Kasalath rice were collected 10-15 days after anthesis. First, panicles were thoroughly washed with deionized water containing a few drops of Tween 20, surface-sterilized with 70% ethanol for 3 minutes, and washed again at room temperature with deionized water before treating with 2% Sodium hypochlorite for 10 minutes. Sterilized panicles were washed with water repeatedly to remove all sodium hypochorite. The husk was manually removed to isolate immature seed, washed again with deionized sterile water before a second sterilization with 70% ethanol followed by three washes with sterile deionized water. Finally, immature seeds were surface-sterilized with 2% Sodium hypochlorite for 30-40 minutes, washed with deionized water remove traces of sterilant. Immature seeds remained in sterilized water during entire subsequent operation. Immature embryos or immature seeds were placed on MSAg medium (Table 3) until the co-cultivation.

tained in vitro throughout. Once plants attained a height of 4-6 inches, they were transferred to the greenhouse for hardening. These plants are referred to as R0 plants.

Acclimatization:

Primary Acclimatization

R0 plants were acclimatized by placing plant in greenhouse under covered tunnel for 3-4 days. At the end of this period plants were removed from agar medium, and all adhering agar was carefully removed from roots by washing with water to avoid future fungus and other plant infection. Root were dipped in Bavistin (Carbendzim, 50% WP, BASF India Ltd. Mumbai) solution (1.0 gm/L) for ½-1 minute before transplanting in net pots containing "Soilrite Mix" (Chougule Industries, Bangalore, India), or "Cocopeat" (Varsha Agro Industries, Bangalore India) . A suitable number (50 or 98) of plants in net pots were placed on portray (a plastic tray, of dimension 52.5 cm length×25.25 cm width, containing 50 plug holes and each plug hole, with a dimension of 5 cm diameter & 5 cm depth, was fitted with a net pot (5 cm

TABLE 3

Describes composition of different media used for examples of the invention.

| Component/L | MSAg | CC-1 | CC-2 | Delay | Selection | Regeneration | Plant development |
|---|---|---|---|---|---|---|---|
| MS Salts (Hi media, India) | 4.2 g | 4.2 g | 4.2 g | 4.2 g | 4.2 g | 4.2 g | 2.1 g |
| CaCl2.2H2O | 440 mg | 440 mg | 440 mg | 440 mg | 440 mg | 440 mg | 0 |
| Thiamine HCl | 1.0 mg | 0.5 mg | 0.5 mg | 0 | 1.0 mg | 0 | 0 |
| Glutamine | 500 mg | 0 | 0 | 0 | 500 mg | 0 | 0 |
| Myo-Inositol | 0 | 0 | 0 | 0 | 0 | 100 mg | 0 |
| Magnesium chloride | 750 | 0 | 0 | 0 | 750 | 0 | 0 |
| Casein Hydrolysate | 100 mg | 0 | 0 | 0 | 100 mg | 0 | 0 |
| Sucrose | 20 g | 20 g | 20 g | 20 g | 20 g | 30 | 15 g |
| Glucose | 0 | 10 g | 10 g | 0 | 0 | 0 | 0 |
| 2,4-D | 2 mg | 2 mg | 2 mg | 1.5 mg | 2 mg | 0 | 0 |
| Kinetin | 0 | 0 | 0 | 0.2 mg | 0 | 2.0 mg | 0 |
| NAA | 0 | 0 | 0 | 0 | 0 | 2.0 mg | 0 |
| BAP | 0 | 0 | 0 | 0 | 0 | 4.0 mg | 0 |
| Phytagel | 2.0 g | 0 | 2.0 g | 2 g | 2.0 g | 0 | 0 |
| L-Proline | 0 | 115 mg | 115 mg | 500 | 0 | 0 | 0 |
| Acetosyringone | 0 | 0 | 0 | 0 | 0 | 0 | 0 |
| Cefataxime | 0 | 0 | 0 | 250 mg | 250 | 250 | 250 mg |
| Hygromycin | 0 | 0 | 0 | 0 | 50 mg | 25 mg | 25 mg |

Infection of Rice Plants

Freshly isolated embryos were incubated with bacterial culture (10 μl per 10 embryos) for 10 minutes. Individual embryos were handpicked and cultured on CC2 medium after removing bacterial suspension. Embryos were incubated for three days in the dark, washed with sterilized water supplemented with Cefotaxime (Sigma Chemical Co Catalog No. 22128) and then blotted dry before culturing on delay medium (Table 3). After one week, roots were excised and scutellar calli were subcultured on selection medium (Table 3)

Selection and Regeneration of Rice Plants

Putative calli were selected by culturing treated calli on selection medium (7-10 day interval) for two to three months or until calli attained 10 mm size. These were then transferred to regeneration medium for a week under darkness. For shoot regeneration, calli were transferred to light. Once plants attained a size of 5-10 mm, they were transferred to bottles containing ½×, Murashige and Skoog basal salts medium (Now on referred as MS medium or MS. MS can be procured from Sigma Chemical Co. Saint Louis, Mo., Catalog No. M8900). Selection pressure with hygromycin was maindiameter×4.7 cm depth) and drenched with fungicide solution Bavistin/Dithane M 45 (1.0 gm/L) (Carbendzim, 50% WP, BASF India Ltd. Mumbai, India/Mancozeb 75% WP Indofil Chemicals Ltd. Mumbai, India).

Newly transplanted RO plants on tray were kept for 7-10 days in a humid chamber with 80%-90% relative humidity, 24° C. -25° C. temperature and 800-100 Lux light intensity. During this period, every 3-4 days the plants were treated with Hoagland nutrient solution ( Sigma Chemical Co. Catalog No. H2395). After initial period of 7-10 days the relative humidity was dropped to 70%-80% and the light intensity was increased to 1100-1500 Lux. Then the plants were treated with 10:52:10 (N:P:K) fertilizer solution at 100 ppm N level and a mild spray of Bavistin (0.5 gm/L).

Secondary Acclimatization

After primary acclimatization plants were acclimatized for 7 days at a light intensity of 1200-1800 Lux, 65%-75% relative humidity and a temperature between 25° C. -26° C. After secondary acclimatization plants were transferred to 6" pots and were grown as described earlier.

Details on number of lines, total plants received and survival status during acclimatization are shown in Table 4.

TABLE 4

Survival Status of transgenic rice plant lines after the acclimatization.

| Batch No. | Date of receipt | GOI | No. of lines | No. of plants | Survival status | | Date of transplanting to pot |
|---|---|---|---|---|---|---|---|
| | | | | | Primary Acclimatization | Secondary Acclimatization | |
| B. N. 2001-9 | May 28, 2001 | Ospk7 | 11 | 33 | 31 | 31 | Jun. 7, 2001 |
| B. N. 2001-9 | Jun. 1, 2001 | Ospk7 | 8 | 22 | 22 | 22 | Jun. 7, 2001 |
| B. N. 2001-10 | Jun. 6, 2002 | Ospk7 | 1 | 3 | 3 | 3 | Jun. 18, 2001 |

Example 6

This example describes a method of determining in-planta sequence of OsPK7 gene in a rice plant transformed with the OsPK7 gene or its homolog. The basic methodology presented in this example can be used for determining in-planta sequence in any plant of the invention.

DNA Isolation

Rice plant DNA was prepared using the Phenol extraction method, modified from Sambrook et al., (1989). 0.5 to 1.0 g leaf tissue was grinded with liquid nitrogen into a fine powder, and then was mixed with extraction buffer immediately (at 1:5 w/v ratio, and buffer composition: 500 mM NaCl, 100 mM Tris -Hcl (PH 8.0), 0.5% SDS, 50 mM EDTA, 80 mM Beta-Mercaptoethanol) and incubated at 65° C. for 10 minutes. Equal volume of phenol: chloroform (1:1) was added and gently mixed for 3 to 5 minutes, centrifuged at 10,000 rpm for 10 minutes and the aqueous phase was transferred into a fresh tube. The aqueous phase was extracted one more time using only chloroform, and then added with two volumes of chilled ethanol and gently mixed. DNA precipitates were spooled into a fresh 1.5 ml tube and dissolved in 800 ul Tris-EDTA (TE) buffer at room temperature. 5 ul of RNAase (10 mg/ml) was added and incubated at 37° C. for 30 minutes. The DNA sample was then extracted with Phenol: chloroform (1:1) twice and chloroform once, and precipitated using one tenth volume of 3M sodium acetate (pH 5.4) and two volumes of ethanol. DNA was spooled into a fresh 1.5 ml microfuge tube and washed with 70% ethanol. DNA pellet was then dissolved in 60 to 100 ul TE buffer pH 8.0.

Amplification of Gene from Isolated DNA:

Nested sets of PCR primers were designed based on the expression cassette of the plant transformation construct. Designing of primer pairs is well known in the art and is also briefly described in example two of the present disclosure. Approximately 10 ng of isolated genomic DNA from each transgenic rice plant was used in a standard PCR reaction for amplification of in-planta gene. Reaction mixture with genomic DNA, appropriated primer pairs, and enzyme in reaction buffer was subjected to initial denaturation of DNA by heating the mixture at 94° C., 2 minutes in a PCR machine, followed by 40 cycles of reaction. Each cycle consisted of denaturation at 94° C. for 30 seconds, annealing at 61° C. for 30 seconds followed by primer extension at 72° C. for 90 seconds. Amplified DNA was isolated at the end of PCR reaction by using QIAquick Gel extraction kit (Qiagen, Cat No. 28704, Qiagen Inc., Santa Clara, Calif. U.S.A.). The DNA was eluted in TE buffer pH 8.0 and stored at −20° C. till further use.

Sequencing of Isolated In-Planta gene:

Amplified DNA was used as a template in standard sequencing reaction. Standard method of sequencing is described in Example 3 of the present disclosure. The DNA was sequenced by using sequencing primers designed on the basis of expression cassette of the gene in rice plants. In-planta gene sequences from two of the events in rice plants were confirmed to be same and are presented as SEQ ID No: 50 and its translation is presented as SEQ ID NO 51.

In some cases sequencing the in-planta gene from different events of transgenic plants demonstrates minor variation in gene sequences. Minor sequence variation is capable of providing variation in the level of the desired phenotype in plants. Some sequence variations were observed when comparing the gene sequence from the transformation construct isolated from agrobacterium and the gene sequence isolated from transgenic rice events transformed with the construct.

Example 7

This example describes the morphological assay and observations performed on rice plants of the present invention.

Transgenic and non-transgenic isolines were segregated based on the southern analysis of genomic DNA isolated from plants. Southern analysis of plant genomic DNA was performed by standard procedures as described in Molecular Cloning, A Laboratory Manual, Sambrook et al., (1989) and using a hpt DNA fragment as a non-radioactive probe (using material and protocol supplied in AlkPhos Direct labeling and detection kit, Amersham pharmacia).

Morphological Assay on R1 Seeds

R1 seeds were germinated on MS medium with 50 mg/L hygormycin to separate transgenic seeds from non-transgenic, and for further physiological/phenotypical analysis. A subset of these seeds with the transgene was allowed to mature for production of R2 seeds. 15-20 seeds from 10 independent lines with different copy numbers of genes were de-husked, surface sterilized and inoculated on MS medium in culture bottles. Bottles were incubated in the dark for 2 days and later on transferred to light. At the end of the incubation period (13 Days) the plants were removed from the bottles and washed under a gentle flow of water and used for transplanting. The first ten tallest seedlings were transplanted to pots for further morphological analysis of R1 plants.

Morphological data on R1 plants were recorded. Results are shown in Table 5.

TABLE 5

Morphological observation of R1 plants

| Plant ID | DOH | NUMBER OF TILLERS TOTAL NO. | NUMBER OF TILLERS PROD. | PLANT HEIGHT | PANICLE LENGTH | SEED WT. PER 1000 | YIELD PER PLANT TOTAL Yield | YIELD PER PLANT Seed Yield |
|---|---|---|---|---|---|---|---|---|
| WT (Kasalath) | 74 ± 0.00 | 13.00 ± 1.49 | 11.70 ± 0.95 | 149.29 ± 6.05 | 26.82 ± 0.54 | 16.13 ± 0.65 | 18.91 ± 4.36 | 18.08 ± 4.48 |
| 653-4-1 | 76.80 ± 4.08 | 23.40 ± 3.95 | 21.80 ± 3.85 | 141.65 ± 6.87 | 23.40 ± 1.28 | 16.76 ± 0.54 | 12.67 ± 8.77 | 10.66 ± 9.22 |
| 652-1-1 | 77.62 ± 5.41 | 13.62 ± 5.41 | 12.54 ± 4s.61 | 145.55 ± 11.55 | 23.16 ± 2.44 | 16.35 ± 0.52 | 14.94 ± 4.09 | 13.86 ± 3.89 |
| 652-5-1 | 78.50 ± 5.61 | 11.17 ± 1.17 | 10.33 ± 1.51 | 153.61 ± 7.25 | 22.02 ± 0.88 | 17.12 ± 0.94 | 9.71 ± 4.49 | 8.52 ± 4.75 |
| 652-6-1 | 82.30 ± 5.10 | 12.50 ± 2.17 | 11.40 ± 1.84 | 141.35 ± 5.97 | 25.08 ± 1.30 | 17.78 ± 2.25 | 8.21 ± 6.08 | 6.95 ± 5.99 |
| 610-1-1 | 87.00 ± 0.00 | 12.38 ± 3.85 | 11.13 ± 3.56 | 146.83 ± 8.04 | 24.98 ± 0.69 | 16.58 ± 1.52 | 5.68 ± 3.67 | 4.35 ± 3.99 |
| 610-2-3 | 76.44 ± 6.88 | 15.11 ± 2.89 | 13.44 ± 3.68 | 143.41 ± 6.06 | 25.14 ± 0.64 | 17.31 ± 0.43 | 8.07 ± 4.76 | 6.25 ± 5.22 |
| 612-1-1 | 76.63 ± 1.06 | 9.88 ± 1.46 | 9.00 ± 1.77 | 142.91 ± 6.24 | 25.40 ± 0.90 | 16.26 ± 0.42 | 11.15 ± 3.19 | 10.47 ± 3.31 |
| 647-1-1 | 80.88 ± 3.23 | 15.88 ± 2.30 | 14.75 ± 2.31 | 136.51 ± 5.60 | 24.39 ± 1.14 | 16.76 ± 0.41 | 6.42 ± 3.87 | 5.39 ± 3.85 |

Table legend:
DOH (Day of heading) - this explains how many days the plant has taken for flowering after transplanting.
Data given here is an average of 8–12 plants from each event with standard deviation.
WT - Wild type is control set.

Example 8

This example explains the selection of homozygous rice line for performing physiological experiments on transgenic plants of the present invention.

Homozygosity test for R2 seeds

Rice is a self-pollinated crop. Hence the R1 seed pool from a R0 transgenic plant with a single copy of the transgene will harbor the transgene in 1:2:1 ratio i.e one homozygous, 2 heterozygous and one null segregant. R1 homozygous plants will produce R2 seeds where all the seeds are transgenic and homozygous. Therefore homozygous lines were identified in the R2 generation by germinating 30 R2 seeds from individual clones from different events on ½ strength MS medium supplemented with hygormycin as described earlier. A line with more than 80% germination is considered homozygous as germination is also affected by seed quality. Seeds from these homozygous lines were used in different physiological assays.

TABLE 6

Homozygosity test

| Sl No. | Plant ID | GOI | Variety | No. of seeds Inoculated | No. of seeds Germinated |
|---|---|---|---|---|---|
| 1 | T₁ 610-1-1-1 | OSPK-7 | 41 | 30 | 30 |
| 2 | T₁ 610-1-1-2 | OSPK-7 | 41 | 30 | 22 |
| 3 | T₁ 610-1-1-3 | OSPK-7 | 41 | 30 | 28 |
| 4 | T₁ 610-2-3-1 | OSPK-7 | 41 | 30 | 28 |
| 5 | T₁ 610-2-3-3 | OSPK-7 | 41 | 30 | 19 |
| 6 | T₁ 610-2-3-4 | OSPK-7 | 41 | 30 | 22 |
| 7 | T₁ 612-1-1-1 | OSPK-7 | 41 | 30 | 20 |
| 8 | T₁ 612-1-1-2 | OSPK-7 | 41 | 30 | 27 |
| 9 | T₁ 612-1-1-3 | OSPK-7 | 41 | 30 | 19 |
| 10 | T₁ 647-1-1-1 | OSPK-7 | 41 | 30 | 26 |
| 11 | T₁ 647-1-1-2 | OSPK-7 | 41 | 30 | 19 |
| 12 | T₁ 647-1-1-3 | OSPK-7 | 41 | 30 | 23 |
| 13 | T₁ 652-1-1-1 | OSPK-7 | 41 | 30 | 28 |
| 14 | T₁ 652-1-1-5 | OSPK-7 | 41 | 30 | 0 |
| 15 | T₁ 652-1-1-6 | OSPK-7 | 41 | 30 | 0 |
| 16 | T₁ 652-3-1-1 | OSPK-7 | 41 | 30 | 26 |
| 17 | T₁ 652-3-1-2 | OSPK-7 | 41 | 30 | 0 |
| 18 | T₁ 652-3-1-3 | OSPK-7 | 41 | 30 | 0 |
| 19 | T₁ 652-3-1-5 | OSPK-7 | 41 | 30 | 5 |
| 20 | T₁ 652-5-1-1 | OSPK-7 | 41 | 30 | 30 |
| 21 | T₁ 652-5-1-2 | OSPK-7 | 41 | 30 | 29 |
| 22 | T₁ 652-5-1-3 | OSPK-7 | 41 | 30 | 17 |
| 23 | T₁ 652-5-1-6 | OSPK-7 | 41 | 30 | 30 |
| 24 | T₁ 652-6-1-1 | OSPK-7 | 41 | 30 | 24 |
| 25 | T₁ 652-6-1-2 | OSPK-7 | 41 | 30 | 23 |
| 26 | T₁ 652-6-1-3 | OSPK-7 | 41 | 30 | 19 |
| 27 | T₁ 653-4-1-1 | OSPK-7 | 41 | 30 | 23 |
| 28 | T₁ 653-4-1-2 | OSPK-7 | 41 | 30 | 23 |
| 29 | T₁ 653-4-1-3 | OSPK-7 | 41 | 30 | 25 |
| 30 | T₁ 653-4-1-5 | OSPK-7 | 41 | 30 | 30 |
| 31 | T₁ 653-4-1-6 | OSPK-7 | 41 | 35 | 34 |
| 32 | T₁ 653-4-1-7 | OSPK-7 | 41 | 30 | 30 |
| 33 | 41 control | OSPK-7 | 41 | 27 | 25 |
| 34 | 41 control | OSPK-7 | | 35 | 0 |

Example 9

This example explains the water stress test for analyzing transgenic rice plants of the tion.

R2 Generation Water Stress Test—Rapid Stress:

Germinated seedlings were planted in portrays. For plating seedlings each net pot was filled with 75 g of red sandy loam soil (dry) and the entire tray was drenched to saturation level with water containing fungicide Bavistin (1 gm/l). Excess water was drained before weighing the entire tray as well as individual net pots. Individual net pots with water-saturated soil weighing about 95 to 100 grams were considered at 100% field water capacity. Germinated seedlings were further grown in the greenhouse with conditions as described in example 1. Every day during the growth period lost water was measured (by weighing pots) and replenished to maintain 100% of field water capacity in the desired pots. Loss of water in pots with plants was due to evaporation and transpiration. Ten net pots were maintained without plants to calculate the amount of water lost due to evaporation. Plants were fertilized once every three days with a solution containing 3 gm urea, 6 gm N:P:K (17:17:17), 0.5 gm $FeSO_4$ and 2.5 gm micronutrient mix/32 L. Fifteen-day-old seedlings were subjected to water stress by withholding irrigation for 4 days. Subsequently net pots were saturated with water and excess water was drained to attain 100% field water capacity for alleviating stress. The plats were maintained at 100% field capacity throughout the recovery period by weighing the pot every day and replenishing the amount of water lost through evaporation/transpiration. The plants were allowed to recover for twelve days. At the end of recovery i.e., the 12$^{th}$ day, growth was measured by weighing only the shoot (above soil, i.e without root). Growth was recorded as fresh weight in milligrams as shown in Table 7. The transgenic lines of the present invention were observed to have significantly higher biomass at the end of recovery as compared to the wild type rice line.

TABLE 7

Result of the R2 generation water stress test.

| lines | Fresh. Wt. (mg) |
|---|---|
| R2-610-1-1-3 | 311.0 ± 68.4 |
| R2-610-2-3-1 | 445.5 ± 95.5 |
| R2-612-1-1-2 | 390.3 ± 71.3 |
| R2-652-5-1-1 | 343.8 ± 53.8 |
| R2-652-3-1-1 | 332.5 ± 51.8 |
| R2-653-4-1-5 | 297.2 ± 41.8 |
| WT - kasalath (wild type non-tansgenic control | 170.4 ± 70.1 |

Example 10

This example demonstrates the rate of survival of transgenic rice plants as compared to non-transgenic rice plants after the water stress.

Three-leaf or 12 days old rice seedlings grown as per the earlier description and were subjected to water stress by withholding irrigation for two days and allowing the plant to recover for 8 days. At the end of recovery, surviving seedling were counted and expressed as percent seedling survival. For determining percent survival of transgenic rice plants, five different sets of experiments designated as 2a, 2b, 2c, 2d, and 2e, were conducted as described above. Ten plants/set were used for this experiment. The results of this experiment are shown in Table 8 indicating all transgenic lines except R2-610-2-3-1 exhibited a significantly high rate of survival at the end of water stress compared to that of wild type.

TABLE 8

Showing the survival of transgenic rice seedlings as compared to non-transgenic rice seedlings after water stress treatment.

| Line code | Lines | Survival at the end of recovery (%) | | | | |
|---|---|---|---|---|---|---|
| | | Exp. 2a | Exp. 2b | Exp. 2c | Exp. 2d | Exp. 2e |
| 1 | R2-610-1-1-3 | 30 | 27 | 40 | ND | ND |
| 2 | R2-610-2-3-1 | 0 | 20 | 0 | ND | ND |
| 3 | R2-612-1-1-2* | 100 | 100 | 100 | 50 | 30 |
| 4 | R2-647-1-1-1 | 50 | 54 | 20 | 80 | 60 |
| 5 | R2-652-1-1-1 | ND | ND | 60 | ND | ND |
| 6 | R2-652-5-1-1 | ND | ND | 60 | 80 | 80 |
| 7 | R2-652-3-1-1 | 66 | 54 | 60 | 60 | 20 |
| 8 | R2-653-4-1-5 | 83 | 63 | 80 | 70 | 10 |
| 9 | WT - kasalath (wild type non-tansgenic control) | 16 | 41 | 0 | 0 | 0 |

Example 11

This example demonstrates the effect of water stress on plant biomass in transgenic rice plants of the invention in comparison with wild type rice plants.

Three-leaf or 12 day-old rice seedlings, grown as per the description of Example 7, were subjected to water stress by withholding irrigation for two days and allowing plants to recover for 10 days. At the end of recovery, growth was measured in terms of fresh weight. Results of this experiment are shown in Table 9. The transgenic lines of the present invention maintained higher average biomass at the end of recovery compared to that of the wild type.

TABLE 9

Biomass of rice seedlings as compared to non-transgenic rice seedlings after water stress treatment. Biomass of plant is indicated as fresh weight in milligrams. WT Kasalath is natural, wild type rice plant.

| Line code | Lines | Fresh weight (mg) |
|---|---|---|
| 3 | R2-612-1-1-3 | 243.89 ± 227.45 |
| 4 | R2-647-1-1-2 | 438.44 ± 273.98 |
| 6 | R2-652-5-1-1 | 582.00 ± 374.53 |
| 7 | R2-652-3-1-1 | 417.44 ± 327.82 |
| 8 | R2-653-4-1-5 | 318.22 ± 271.63 |
| WT | WT - Kasalath | 152.89 ± 112.52 |

Example 12

This example demonstrates the effect of water stress on plant biomass in older transgenic rice plants of the invention in comparison with wild type rice plants.

Five-leaf or 20 day-old rice seedlings, grown as per the description of Example 7 were subjected to water stress by withholding irrigation for two days and allowing plants to recover 6 days. At the end of recovery, growth was measured in terms of fresh weight. Results of this experiment are shown in Table 10. The transgenic lines of the present invention maintained higher average biomass at the end of recovery compared to that of the wild type.

TABLE 10

Biomass of older rice seedling as compared to non-transgenic rice seedlings after water stress treatment. Biomass of the plant is indicated as fresh weight in milligrams. WT - kasalath is non-transgenic.

| Line code | Lines | Fresh weight (mg) |
|---|---|---|
| 3 | R2-612-1-1-3 | 153.7 ± 40.8 |
| 4 | R2-647-1-1-2 | 363.4 ± 109.79 |
| 6 | R2-652-5-1-1 | 484.5 ± 180.59 |
| 7 | R2-652-3-1-1 | 266.5 ± 96.03 |
| 8 | R2-653-4-1-5 | 215.4 ± 78.33 |
| WT | WT - Kasalath | 252.9 ± 93.28 |

Example 13

This example describes the effect of long term stress on R2 plants of the present invention.

Germinated seedlings were transferred to plastic pots (10 cm diameter×4 cm depth) containing 100g of red sandy loam soil with two different levels of water content. The two levels are 25 percent field capacity (FC25 ), 9.3 ml/100 g soil and 100 percent field capacity (FC100), 37.5 ml/100 g soil. The seedlings were allowed to adapted in two different water regimes for 15 days. The seedlings were adapted in the greenhouse. During the growth period the water level was maintained at designated field capacity by weighing the pots every day and replenishing the amount of water lost through evaporation/transpiration. Ten pots were maintained without plants to calculate the amount of water lost due to evaporation. During this period plants were fertilized once every three days with solution as described in Example 7. On the 15th day the difference in growth rate between transgenic and wild type was assessed in terms of leaf extension growth by measuring the length of the 4th leaf. All transgenic lines were observed to have significant leaf growth differences as compared to non-transgenic lines under experimental stress conditions as described in this example. Results are show below in table 11.

TABLE 11

Effect of Long term Stress on R2 rice plants of present invention as compared to non transgenic WT - kasalath rice plants.

| Line code | Lines | Stressed (FC 25) | Non-stressed (FC-100) |
|---|---|---|---|
| 1 | R2-610-1-1-3 | 11.45 ± 3.5 | 36.48 ± 3.82 |
| 3 | R2-612-1-1-2 | 9.34 ± 2.51 | 33.55 ± 3.15 |
| 4 | R2-652-5-1-1 | 10.25 ± 1.96 | 33.76 ± 2.03 |
| 7 | R2-652-3-1-1 | 8.07 ± 2.89 | 32.18 ± 3.84 |
| 9 | WT - kasalath | 5.74 ± 1.86 | 33.52 ± 3.59 |

Example 14

This example demonstrates the effect of cold stress on rice plants of the present invention.

Twelve-day-old or three leaf stage seedlings were grown according to Example 7 and were exposed to cold temperature at 12° C. for 24 hours in the presence of 1000 micro mol/mt2/Sec.light. Subsequently, the plants were allowed to recover in the greenhouse for 20 days. The growth observations such as the length of the 4th leaf on the 7th day and plant height (pl. ht), fresh weight and dry weight were recorded on the 20th day of recovery. The cold stressed OSPK-7 transgenic lines exhibited significantly higher initial recovery growth measured in terms of the length of the 4th leaf at the end of recovery. Further, the transgenic lines exhibited significantly higher plant height and marginally higher total biomass at the end of recovery compared to that of the wild type. Results are shown in Tables 12 and 13.

TABLE 12

Results of recovery growth in terms of the length of the 4th leaf of the plant after exposure to cold temperature.

| Lines code | Lines | Stress | Non-stress |
|---|---|---|---|
| 1 | R2-610-1-1-3 | 18.2 ± 3.5 | 16.9 ± 4.8 |
| 2 | R2-610-2-3-1 | 17.9 ± 2.1 | 21.6 ± 3.2 |
| 3 | R2-612-1-1-2 | 22.1 ± 3.2 | 21.2 ± 3.2 |
| 4 | R2-652-5-1-1 | 19.1 ± 2.0 | 19.4 ± 6.2 |
| 7 | R2-652-3-1-1 | 30.9 ± 3.1 | 18.8 ± 6.2 |
| 8 | R2-653-4-1-5 | 15.3 ± 2.5 | 21.0 ± 3.5 |
| 9 | WT - kasalath | 3.7 ± 2.2 | 23.3 ± 3.3 |

TABLE 13

Results of recovery in terms of plant height, fresh weight, and dry weight after exposure to cold temperature.

| Lines | Plant ht.(cm) | Fresh weight (mg) | Dry weight (mg) |
|---|---|---|---|
| R2-610-1-1-3 | 32.5 ± 5.5 | 354.9 ± 77.0 | 86.9 ± 19.5 |
| R2-610-2-3-1 | 35.3 ± 3.1 | 389.8 ± 26.8 | 87.8 ± 8.2 |
| R2-612-1-1-3 | 37.2 ± 4.2 | 387.1 ± 46.0 | 104.8 ± 42.7 |
| R2-652-5-1-1 | 35.3 ± 2.6 | 325.8 ± 56.6 | 86.8 ± 10.5 |
| R2-652-3-1-1 | 39.0 ± 5.0 | 488.5 ± 51.1 | 113.2 ± 13.6 |
| R2-653-4-1-5 | 37.7 ± 5.1 | 432.9 ± 94.5 | 91.5 ± 18.0 |
| WT - kasalath | 29.9 ± 2.9 | 364.6 ± 61.6 | 86.0 ± 13.6 |

Example 15

Figure 2:
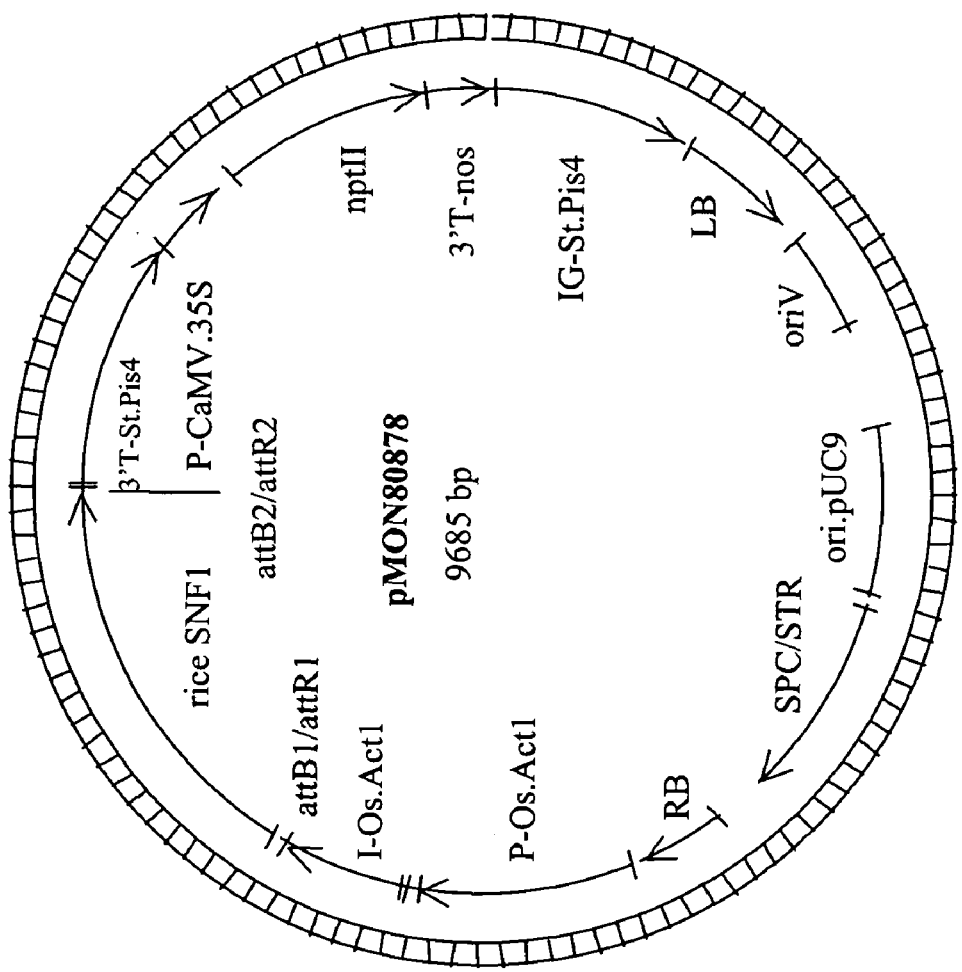
FIG. 2 Plasmid map of plant expression vector pMON 80878
Figure 9:
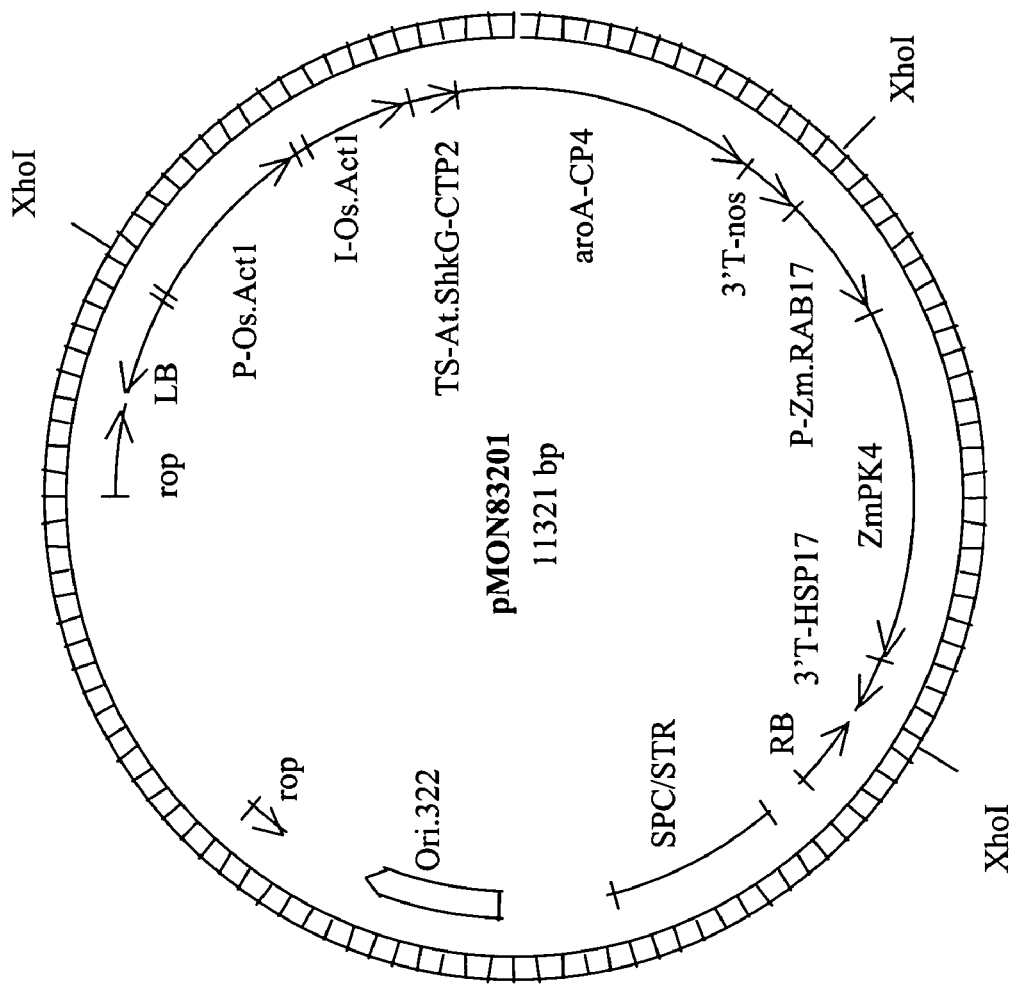
FIG. 9 Plasmid map of plant expression vector pMON 83201
Figure 10:
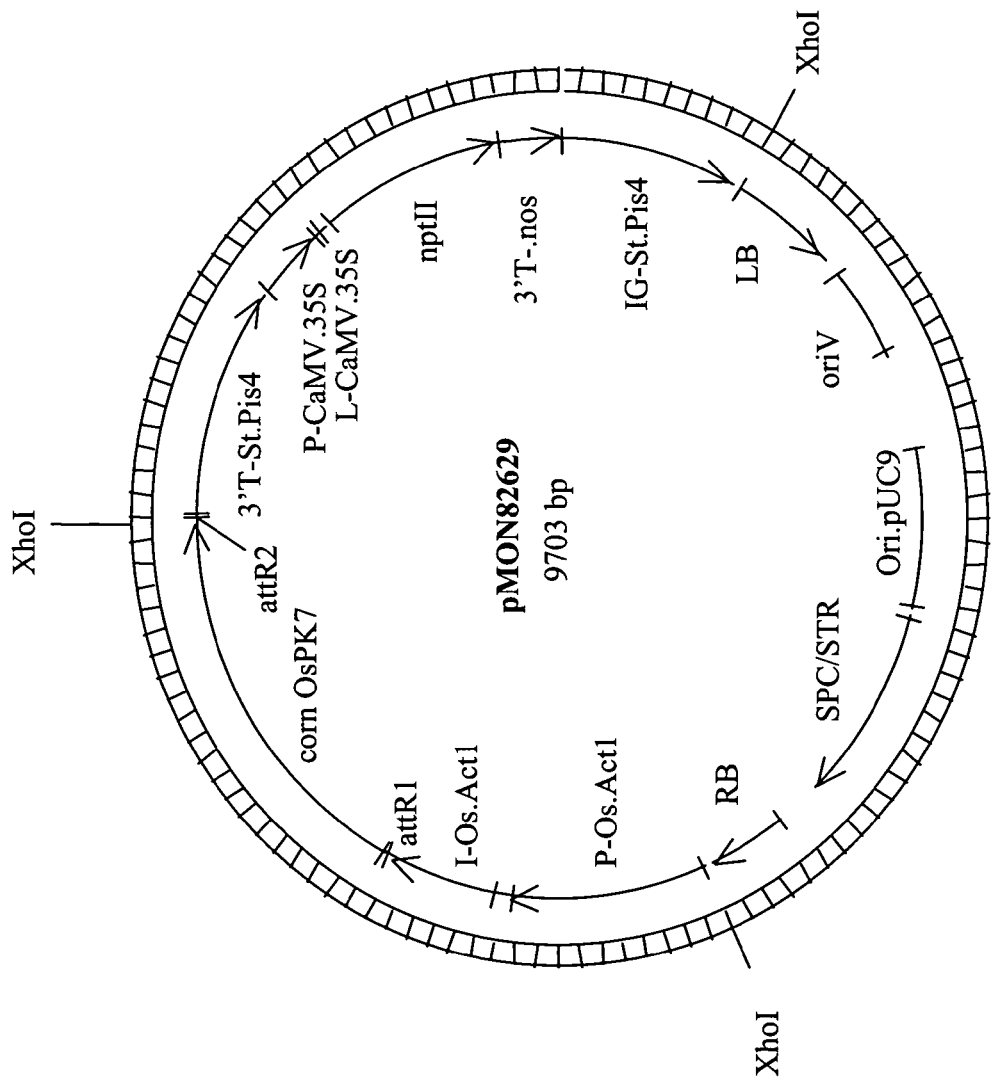
FIG. 10 Plasmid map of plant expression vector pMON 82629

Genetic elements of plant expression vectors pMON 80878 (FIG. 2). PMON 71709 (FIG. 4), pMON 71712 (FIG. 5). pMON 83200 (FIG. 6), pMON 71710 (FIG. 7). pMON 71713 (FIG. 8), pMON 83201 (FIG. 9), and pMON 82629 (FIG. 10).

The DNA constructs are double border plant transformation constructs that also contain DNA segments that provide replication function and antibiotic selection in bacterial cells, for example, an *E. coli* origin of replication such as ori322, a broad host range origin of replication such as oriV or oriRi, and a coding region for a selectable marker such as Spc/Str that encodes for Tn7 aminoglycoside adenyltransferase (aadA) conferring resistance to spectinomycin or streptomycin, or a gentamicin (Gm, Gent) selectable marker gene. For plant transformation, the host bacterial strain is *Agrobacterium tumefaciens* ABI or LBA4404.

The polylinker regions in these DNA constructs provide for multiple restriction endonuclease cut sites that digest the DNA to provide a cloning site. Examples of such cloning sites may include BglII, NcoI, EcoRI, SalI, Not1, XhoI and other sites known to those skilled in the art of molecular biology. pMON 72472 plant expression vector (FIG. 1) is modified for cloning and expression of SEQ ID NO: 1 from rice plants by changing multiple cloning sites to accept a DNA fragment with Not1 and Sal1 restriction enonuclease fragment. SEQ ID NO: 1 is in cloned pMON 72472 (FIG. 1) or pMON53616 (FIG. 3) at a restriction site resulting in a plant expression vector pMON 80878 (FIG. 2) pMON 71709 (FIG. 4). The construct is used for transforming wild type corn plants to generated transgenic corn plants. Orthologs of SEQ ID NO: 1 are cloned in vector pMON 53616 or pMON 72472 by replacing an existing expression cassette of the construct with a desired expression cassette containing a desired promoter, the polynucletide of the present invention and desired 3' terminator resulting in constructs pMON 71712, pMON 83200, pMON 71710, pMON 71713, pMON 83201 or pMON 71709 as shown in FIGS. 5 to 10 and Table 14.

TABLE 14

Construction of plant transforming vectors.

Figure 3:
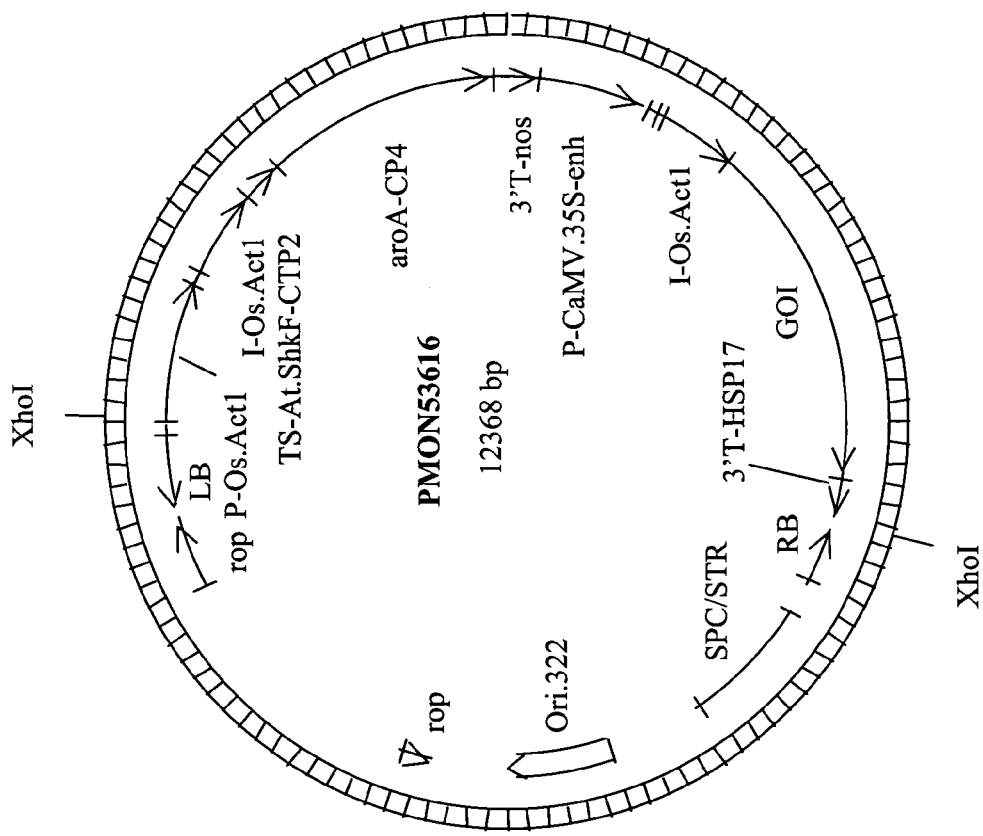
FIG. 3 Plasmid map of plant expression vector pMON 53616
Figure 4:
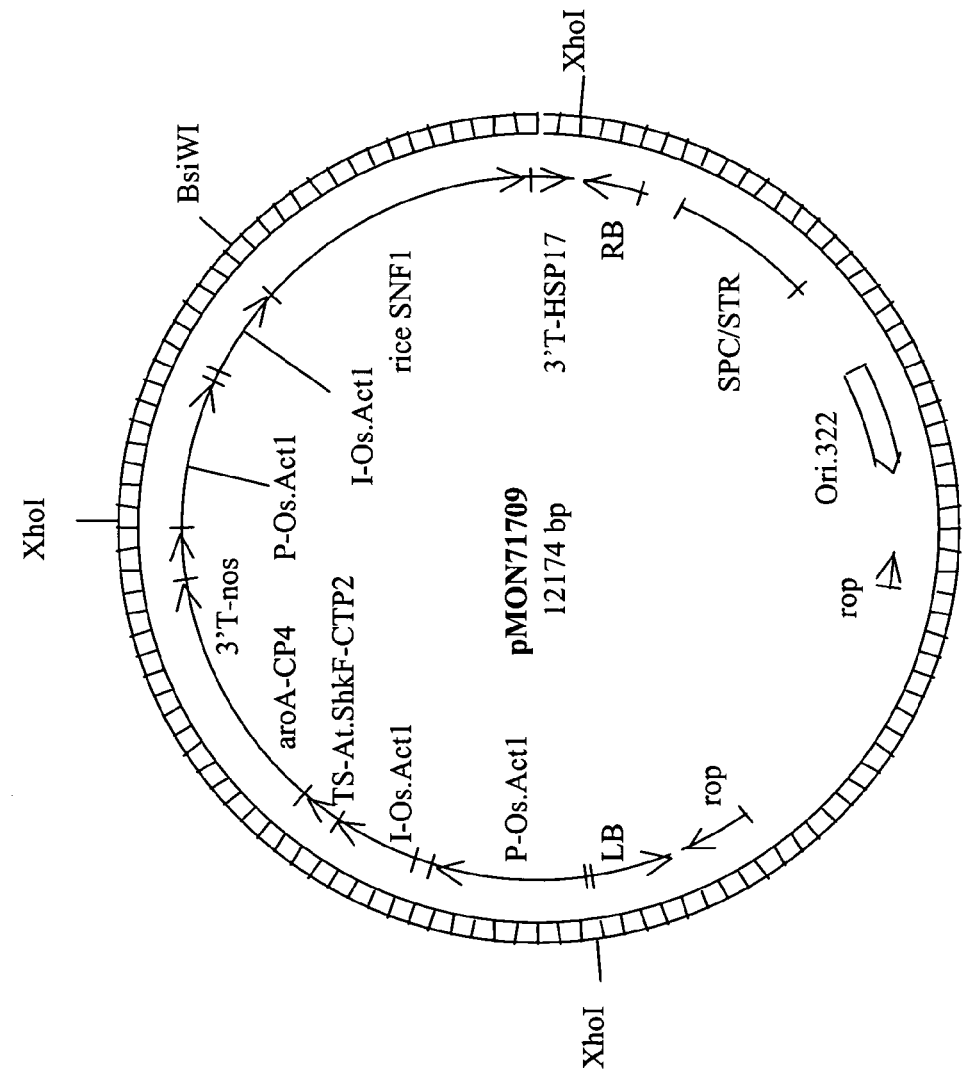
FIG. 4 Plasmid map of plant expression vector pMON 71709

| Gene/Homolog name | Plant of origin | Construct name | Vector for the construct | Cloning sites | Transformed plant | Construct's Figure | Promoter |
|---|---|---|---|---|---|---|---|
| OsPK7 | *Oryza sativa* | pMON80878 | pMON 72472 | attB1 and attB2 | LH59 corn | FIG. 1 | rACT (promoter leader, intron) |
| OsPK7 | Oryza sativa | pMON71709 | pMON 53616 | 5' BsiWI; 3' XhoI (destroyed by ligation to Not1) | LH244 corn, haploid LH244 corn | FIG. 2 | rACT (promoter leader, intron) |
| OsPK7 | Oryza sativa | pMON71712 | pMON 53616 | 5' BsiWI; 3' XhoI (destroyed by ligation to SalI) | LH244 corn | FIG. 3 | CVY-CIK1 (promoter, intron leader) |

TABLE 14-continued

Construction of plant transforming vectors.

Figure 5:
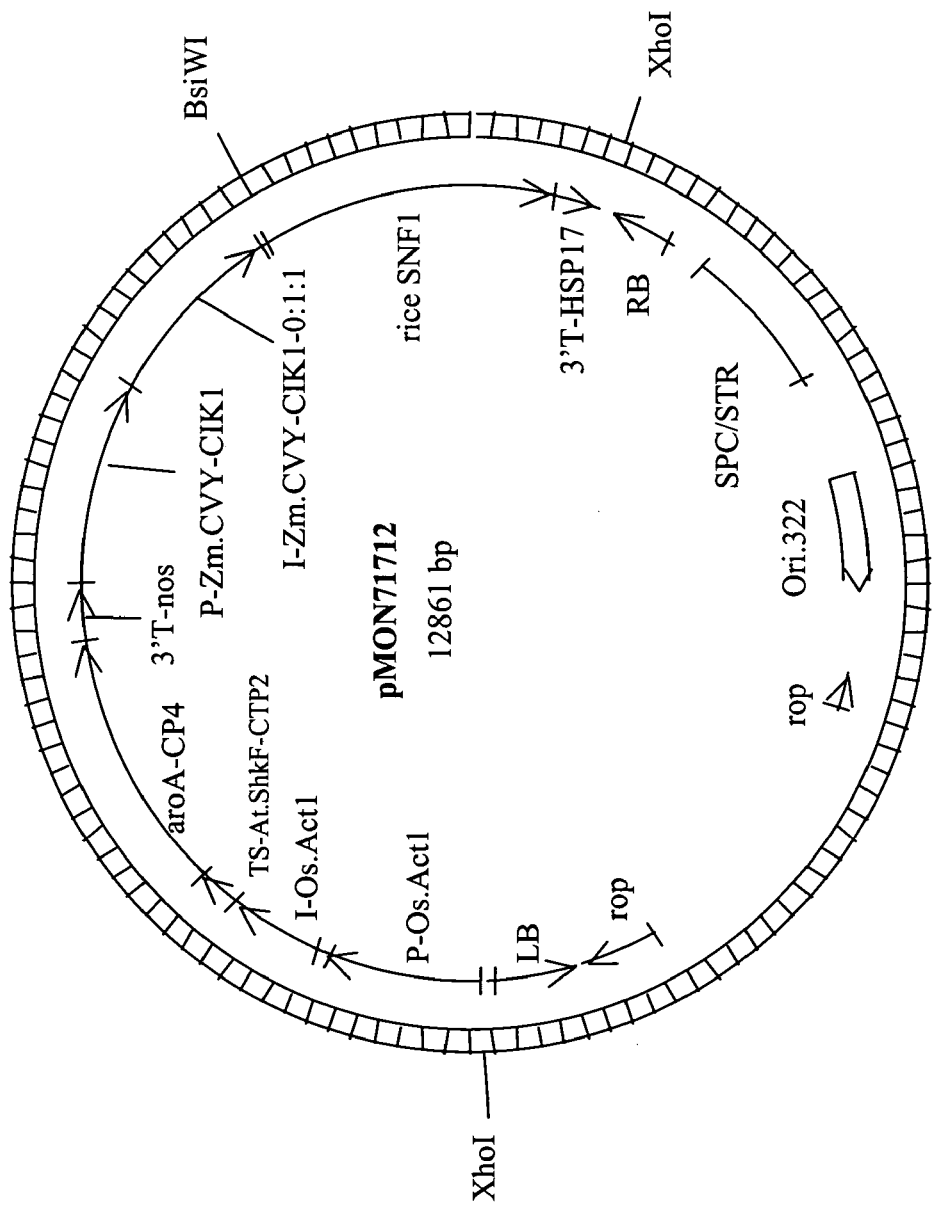
FIG. 5 Plasmid map of plant expression vector pMON 71712
Figure 6:
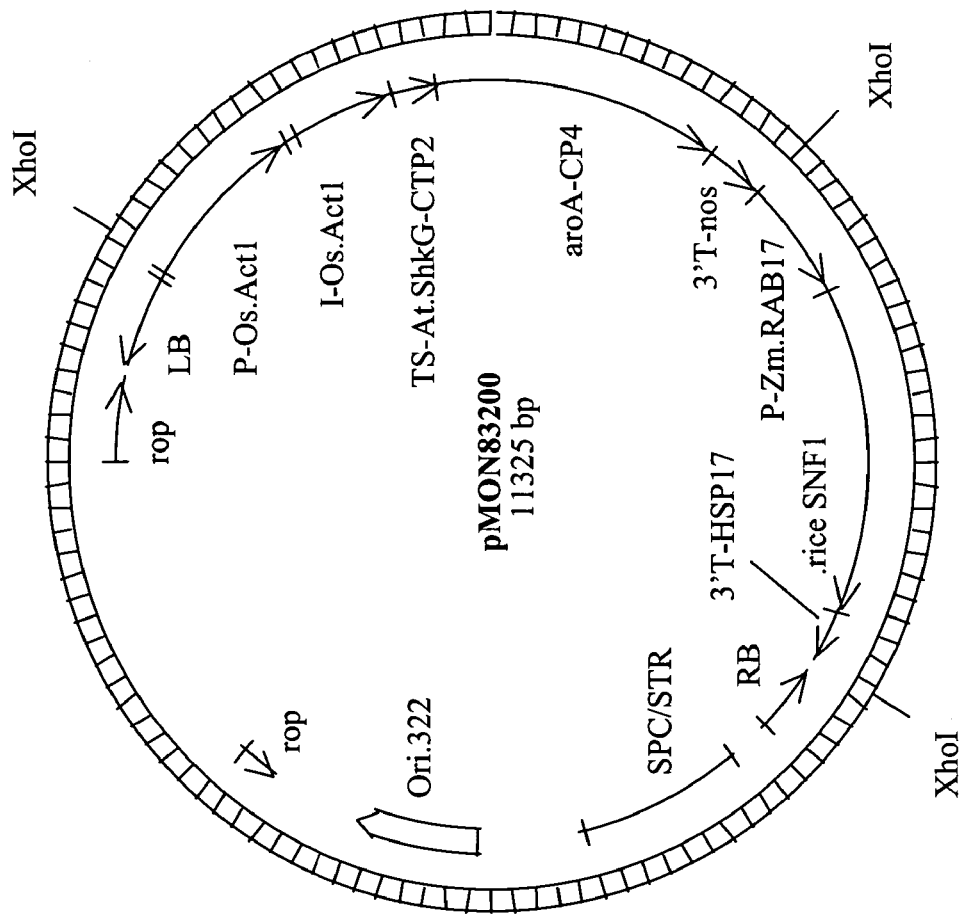
FIG. 6 Plasmid map of plant expression vector pMON 83200
Figure 7:
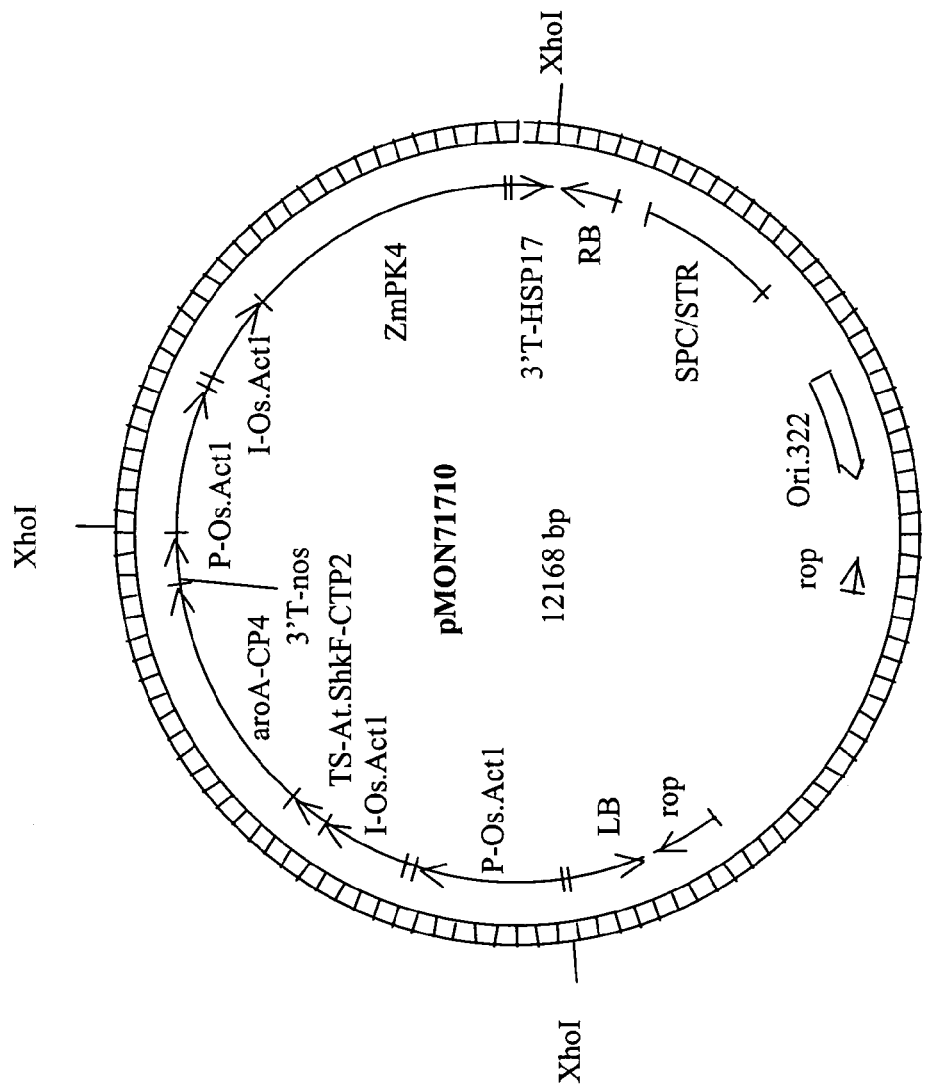
FIG. 7 Plasmid map of plant expression vector pMON 71710
Figure 8:
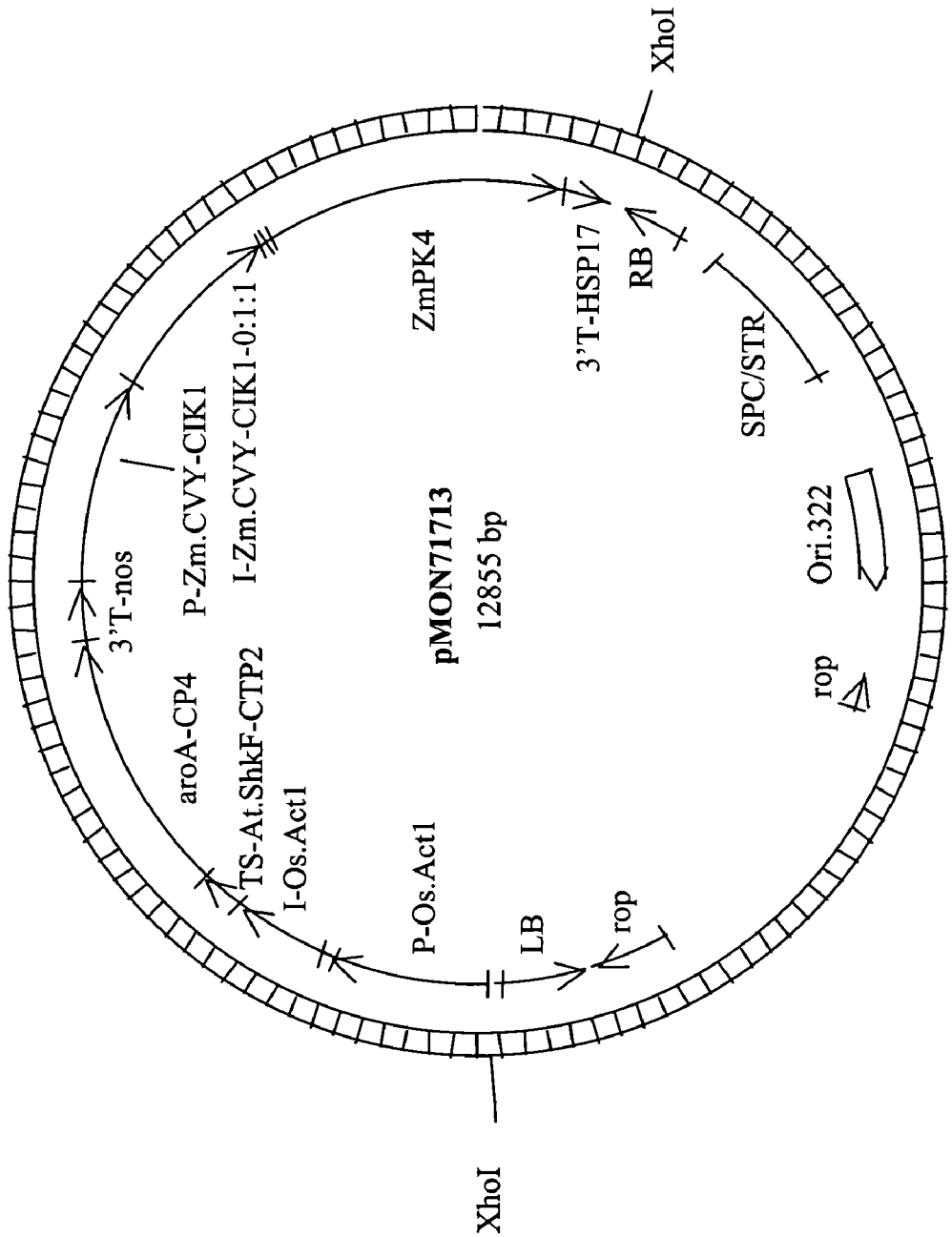
FIG. 8 Plasmid map of plant expression vector pMON 71713

| Gene/Homolog name | Plant of origin | Construct name | Vector for the construct | Cloning sites | Transformed plant | Construct's Figure | Promoter |
|---|---|---|---|---|---|---|---|
| OsPK7 | Oryza sativa | pMON 83200 | pMON 53616 | 5' BsiWI; 3' XhoI (destroyed by ligation to SalI) | LH244 corn | FIG. 4 | Rab17 |
| ZmPK4 | Zea mays | pMON71710 | pMON 53616 | 5' BsiWI; 3' XhoI (destroyed by ligation to SalI) | LH244 corn | FIG. 5 | rACT (promoter leader, intron) |
| ZmPK4 | Zea mays | pMON71713 | pMON 53616 | 5' BsiWI; 3' XhoI (destroyed by ligation to SalI) | LH244 corn | FIG. 6 | CVY-CIK1 (promoter, intron leader) |
| ZmPK4 | Zea mays | pMON83201 | pMON 53616 | 5' BsiWI; 3' XhoI (destroyed by ligation to SalI) | LH244 corn | FIG. 7 | Rab17 |
| ZmPK4 | Zea mays | pMON82629 | pMON 72472 | attB1 and attB2 | LH59 corn | FIG. 8 | rACT (promoter leader, intron) |

The DNA constructs used in the method of the current invention comprise any promoter known to function to cause transcription in plant cells and any antibiotic or herbicide tolerance encoding polynucleotide sequence known to confer antibiotic or herbicide tolerance to plant cells. The antibiotic tolerance polynucleotide sequences include, but are not limited to polynucleotide sequences encoding for proteins involved in tolerance to kanamycin, neomycin, hygromycin, and other antibiotics known in the art. An antibiotic tolerance gene in such a vector can be replaced by a herbicide tolerance gene encoding for 5-enolpyruvylshikimate-3-phosphate synthase (EPSPS, described in U.S. Pat. Nos. 5,627,061, and 5,633,435, herein incorporated by reference in its entirety; Padgette et al. (1996) *Herbicide Resistant Crops*, Lewis Publishers, 53-85, and in Penaloza-Vazquez, et al. (1995) Plant Cell Reports 14:482-487), aroA (U.S. Pat. No. 5,094,945) for glyphosate tolerance, bromoxynil nitrilase (Bxn) for Bromoxynil tolerance (U.S. Pat. No. 4,810,648), phytoene desaturase (crti) (Misawa et al, (1993) Plant Journal 4:833-840, and (1994) Plant Jour 6:481-489) for tolerance to norflurazon, acetohydroxyacid synthase (AHAS, Sathasiivan et al. (1990) Nucl. Acids Res. 18:2188-2193) and the bar gene for tolerance to glufosinate (DeBlock, et al. (1987) EMBO J. 6:2513-2519). Herbicides for which transgenic plant tolerance has been demonstrated and the method of the present invention can be applied include, but are not limited to: glyphosate, glufosinate, sulfonylureas, imidazolinones, bromoxynil, delapon, cyclohezanedione, protoporphyrionogen oxidase inhibitors, and isoxaslutole herbicides.

Genetic elements of transgene DNA constructs used for plant transformation and expression of transgenes in plants include, but are not limited to: plant virus promoters, e.g., P-CaMV.35S promoter (U.S. Pat. No. 5,858,742, herein incorporated by reference in its entirety), the CaMV 35S promoter with a duplicated enhancer (U.S. Pat. No.5,539, 142, herein incorporated by reference in its entirety), the Figwort mosaic virus promoter, P-FMV, as described in U.S. Pat. No. 5,378,619, herein incorporated by reference in its entirety; or the P-AtEF1 a (P-AtEF1 or EF1a), the sugarcane bacilliform virus promoter, commelina yellow mottle virus or other Badnavirus promoters; heterologous plant promoters, e.g., plant actin promoters including the rice actin 1 promoter and intron (U.S. Pat. No. 5,641,876) and rice actin 2 promoter and intron (U.S. Pat. No. 6,429,357), *Arabidopsis* actin promoters, a promoter region from the tomato elongation factor gene and *Arabidopsis thaliana* elongation factor gene 1a; or the DC3 promoter region from carrot (Seffens et al., Develop. Genet. 11:65-76); or the TP12 promoter (GenBank accession no. U68483).

The genetic elements of the DNA construct further comprise 5' leader polynucleotides for example, the Hsp70 non-translated leader sequence from *Petunia hybrida* as described in U.S. Pat. No. 5,362,865, herein incorporated by reference in its entirety.

The genetic elements further comprise herbicide tolerance genes that include, but are not limited to, for example, the aroA:CP4 coding region for EPSPS, a glyphosate resistant enzyme isolated from *Agrobacterium tumefaciens* (AGRTU) strain CP4 as described in U.S. Pat. No. 5,633,435, herein incorporated by reference in its entirety.

The genetic elements of the DNA construct further comprise 3' termination regions that include, but are not limited to, the E9 3' termination region of the pea RbcS gene that functions as a polyadenylation signal; the nos3' is the 3' end of the Ti plasmid nopaline synthase gene that functions as a polyadenylation signal; or the TML is 3' of the end of the Ti plasmid octopine pTi15955 synthase gene (GenBank Accession AF 242881) that functions as a polyadenylation signal. The genetic elements of the DNA construct further comprise the right border (RB) and left borders (LB) of the Ti plasmid of *Agrobacterium tumefaciens* octopine and nopaline strains.

Example 16

The following example describes transformation of soy and corn plants with constructs expressing genes of present invention. Different plants were transformed with constructs in accordance with Table 14.

Corn

Transgenic corn can be produced by particle bombardment transformation methods as described in U.S. Pat. No. 5,424, 412. The vector DNA of plasmid pMON 71709, pMON 71710, pMON 71712, pMON 71713 or pMON 80878 is digested with suitable restriction endonucleases to isolate a plant expression cassette that expresses the polypeptides of the present invention in the plant. The desired expression cassette is purified by agarose gel electrophoresis, then bombarded into embryogenic corn tissue culture cells using a Biolistic® (Dupont, Wilmington, Del.) particle gun with purified isolated DNA fragments. Transformed cells are selected on selection media such glyphosate (N-phosphonomethyl glycine and its salts) containing media and whole plants are regenerated then grown under greenhouse conditions. Fertile seed is collected, planted and the glyphosate tolerant phenotype is back crossed into commercially acceptable corn germplasm by methods known in the art of corn breeding (Sprague et al., Corn and Corn Improvement $3^{rd}$ Edition, Am. Soc. Agron. Publ (1988).

Transgenic corn plants can be produced by an *Agrobacterium* mediated transformation method. A disarmed *Agrobacterium* strain C58 (ABI) harboring DNA as described earlier in the example is used for transforming plants. The construct is first transferred into *Agrobacterium* by a triparental mating method (Ditta et al., Proc. Natl. Acad. Sci. 77:7347-7351). Liquid cultures of *Agrobacterium* are initiated from glycerol stocks or from a freshly streaked plate and grown overnight at 26° C.-28° C. with shaking (approximately 150 rpm) to mid-log growth phase in liquid LB medium, pH 7.0 containing 50 mg/l kanamycin, 50 mg/l streptomycin and spectinomycin and 25 mg/l chloramphenicol with 200 µM acetosyringone (AS). The *Agrobacterium* cells are resuspended in the inoculation medium (liquid CM4C) and the density is adjusted to $OD_{660}$ of 1. Freshly isolated Type II immature LH244 and LH59corn embryos are inoculated with *Agrobacterium* containing a DNA construct of the present invention and co-cultured 2-3 days in the dark at 23° C. The embryos are then transferred to delay media (N6 1-100-12/micro/Carb 500/20 µM AgNO3) and incubated at 28° C. for 4 to 5 days. All subsequent cultures are kept at this temperature. Coleoptiles are removed one week after inoculation. The embryos are transferred to the first selection medium (N61-0-12/Carb 500/ 0.5 mM glyphosate). Two weeks later, surviving tissues are transferred to the second selection medium (N61-0-12/Carb 500/1.0 mM glyphosate). Subculture surviving callus every 2 weeks until events can be identified. This will take 3 subcultures on 1.0 mM glyphosate. Once events are identified, bulk up the tissue to regenerate. For regeneration, callus tissues are transferred to the regeneration medium (MSOD, 0.1 µM ABA) and incubated for two weeks. The regenerating calli are transferred to a high sucrose medium and incubated for two weeks. The plantlets are transferred to MSOD media in culture vessel and kept for two weeks. Then the plants with roots are transferred into soil.

Soy Transformation:

Soybean plants are transformed using an *Agrobacterium*-mediated transformation method, as described by Martinell (U.S. Pat. No. 6,384,301, herein incorporated by reference). For this method, overnight cultures of *Agrobacterium tumefaciens* containing the plasmid that includes a gene of interest, are grown to log phase and then diluted to a final optical density at 660 nm ($OD_{660}$) of 0.3 to 0.6 using standard methods known to one skilled in the art. These cultures are used to inoculate the soybean embryo explants prepared as described below.

Commercially available soybean seeds (e.g., Asgrow A3244) are germinated overnight and the meristematic tissue is excised. The excised tissue is placed in a wounding vessel and mixed with the *Agrobacterium* culture described above. The entire tissue is wounded using sonication. Following the wounding, explants are placed in co-culture for 2-5 days, at which point they are transferred to selection media, i.e., WPM (as described on page 19 of U.S. Pat. No. 6,211,430, incorporated herein by reference) with 75 mM glyphosate (plus antibiotics to control *Agrobacterium* overgrowth), for 6-8 weeks to allow selection and growth of transgenic shoots. Phenotype positive shoots are harvested approximately 6-8 weeks post transformation and placed into selective rooting media (BRM, as described in Table 3 of U.S. Pat. No. 6,384, 301) with 25 mM glyphosate) for 3-5 weeks. Shoots producing roots are transferred to the greenhouse and potted in soil. Shoots that remain healthy on selection, but do not produce roots are transferred to non-selective rooting media (BRM without glyphosate) for up to two weeks. Roots from the shoots that produced roots off selection are tested for expression of the plant selectable marker before they are transferred to the greenhouse and potted in soil. Plants are maintained under standard greenhouse conditions until seed harvest (R1). The collected seeds are analyzed for protein and oil as described in Example.

Plant Selection:

After transformation of crop plants, positive tranformants can by selected by any one, or a combination of many know techniques in the art. Plant can be selected based on the resistance provided by the transforming constructs, which may include antibiotic resistance, or herbicide resistance. Plants can also be selected by screening DNA isolated from transformed plant part with polymerase chain reaction for presence or absence of gene itself, or part of the transforming constructs. Gene or protein specific antibodies can also be utilized for selecting transformed plant expressing desired protein.

Example 17

This example describes a cold germination assay for transgenic corn seeds of the present invention.

Three sets of seeds are used for the experiment. The first set consists of twelve different positive transgenic events where the genes of the present invention are expressed in the seed. The second set consists of negative segregants from the same transgenic events as the positive seeds. The third seed set consists of two cold tolerant and two cold sensitive wild-type lines of corn. A number from one to fourteen is randomly assigned to each of the twelve transgenic events, the cold tolerant wild-type lines, and the cold-sensitive wild-type lines. Positive and negative segregants of the same event are designated as "A" and "B" randomly. Each member of the cold-tolerant or cold-sensitive pair is also designated as "A" and "B" randomly. All seeds are treated with a fungicide "Captan" (Arvesta Corporation, San Francisco, Calif., USA). 0.43 mL Captan is applied per 45 g of corn seeds by mixing it well and drying the fungicide prior to the experiment. Incubations at or below 23 degrees Celsius are conducted in growth chambers (Conviron Model PGV36, Controlled Environments, Winnipeg, Canada).

Ten Petri plates for the cold assay and 5 plates for the warm assay are used. Petri plates (Cat. #353003) can be procured from Becton, Dickinson and Company (Franklin Lakes, N.J. USA, from now on referred to as BD Biosciences). Each plate is prepared for the experiment by placing a Whatman No. 1 paper on the inner side of the lid (90 mm Catalog # 1001090) and on the bottom of the plate (85 mm Catalog # 1001085) manufactured by Whatman International Ltd. (Maidstone, England) and wetting them with 2 and 3 ml of sterile water respectively. Ten desired seeds per plate are placed on the bottom filter paper with the embryo side touching the paper, each plate is labeled, the lid with the moist paper is placed on the plate and plates are placed in a growth chamber set at 9.7° C. (for cold assay) or 25° C. (for warm assay) in the dark. Ten plates are laid across the bottom of a plastic box and stacked up to six layers high before placing them in growth chambers. Seeds are watered with 2 ml of deionized sterile water on the $3^{rd}$ and $10^{th}$ days. Warm control seeds are watered only on the $3^{rd}$ day. Seeds are considered germinated if the emerged radicle size is 1 cm. Warm control seeds are scored for germination four days after planting and cold seeds are scored from days 10 to 14, days 17, 19 and 24 after planting. Scoring is conducted until all seeds have germinated or until the end of 24 days after planting. The order of plates is reversed (top to bottom, and bottom to top) on every watering and scoring day. Six radicles per set of plates are harvested at random on the last day of the experiment for analysis of RNA expression by Taqman assay.

After 24 days of data collection, a germination index is calculated for each set of seeds. The germination index is calculated as per:

Germination index=$(\Sigma([T+1-n_i]*[P_i-P_{i-1}]))/T$

Where: T is the total number of days for which the germination experiment is performed. The number of days after planting is defined by n. The number of times the germination has been counted, including the current day, is indicated by i. P is the percentage of seeds germinated during any given rating. Statistical differences are calculated between positive and negative selections within an event. Additionally, the germination rate is fitted to a model to determine the number of days to 50% germination and confidence intervals are used to determine the statistical significance between positive and negative selections within an event. The Taqman assay confirms the expression of the RNA of the present invention. Any event which achieved 85% or better germination in the warm is used for the cold assay; otherwise it is dropped from the cold assay.

Example 18

This example describes a cold shock assay for transgenic corn seeds of the present invention.

Experimental set-up for the cold shock assay is the same as described in above example's second paragraph, except seeds are grown in potted media for the cold shock assay.

The desired number of 2.5" square plastic pots are placed on flats (n=32, 4×8). Pots are filled with Metro Mix 200 soilless media containing 19:6:12 fertilizer (6 lbs/cubic yard) (Metro Mix, Pots and Flat are obtained from Hummert International, Earth City, Mo.). After planting seeds, pots are placed in a growth chamber set at 23° C., relative humidity of 65% with 12 hour day and night photoperiod (300 uE/m2-min). Planted seeds are watered for 20 minute every other day by sub-irrigation and flats are rotated every third day in a growth chamber for growing corn seedlings.

Chlorophyll fluorescence of plants is measured on the $10^{th}$ day during the dark period of growth by using a PAM-2000 portable fluorometer as per the manufacturer's instructions (Walz, Germany). After chlorophyll measurements, leaf samples from each event are collected for confirming the expression of genes of the present invention. For expression analysis six VI leaf tips from each selection are randomly harvested. Expression analysis can be done using a Taqman assay to estimate the RNA expression the 3' termination sequence or any other part of expression cassette which will be part of the transgenic plant genome. Plants are then repositioned in one flat by alternating between the "A" and "B" selection for a total of sixteen "A" plants and sixteen "B" plants per flat (A & B are described earlier examples). The flats are moved to a growth chamber set at 5° C. The actual temperature at canopy level is 5° C. during the dark cycle and 8° C. during the light cycle. All other conditions such as humidity, day/night cycle and light intensity are kept the same in the growth chamber. The flats are sub-irrigated every day after transfer to the cold temperature. On the $4^{th}$ day chlorophyll fluorescence is measured again. Plants are transferred to normal growth conditions after six days of cold shock treatment and allowed to recover for the next two days. During this recovery period the length of the V3 leaf is measured on the $1^{st}$ and $3^{rd}$ days. After two days of recovery V2 leaf damage is visually estimated by estimating percent of green V2 leaf.

Statistical differences in V3 leaf growth, V2 necrosis and fluorescence during pre-shock and cold shock can be used for estimation of cold shock damage on corn plants.

Example 19

This example describes the early seedling growth assay for transgenic corn seeds of the present invention.

Experimental set-up for the cold shock assay is the same as described in example 15 second paragraph, except seeds are grown in germination paper for the early seedling growth assay.

Three pieces of 12"×18" germination paper (Anchor Paper #SD7606) are used for each entry in the test, "A" and "B". For each entry the papers are numbered #1 to #3. A line is drawn using a wax pencil across the long dimension of the paper at about four inches from the top edge. Wet the papers in a solution of 0.5% $KNO_3$ and 0.1% Thyram. For each paper, eighteen seeds are placed on the line evenly spaced down the length of the paper. The eighteen seeds are positioned on the paper such that the radical will grow downwards, e.g. longer distance to the paper's edge. The wet paper is rolled up starting from one of the short ends. The paper is rolled evenly and tight enough to hold the seeds in place. The roll is secured into place with two large paper clips, one at the top and one at the bottom. The rolls are placed on end in a tall bucket containing about one inch of the $KNO_3$/thyram solution. The top of the bucket is covered with a plastic bag. The bag is secured such that the rolls are protected from a direct breeze or strong flow of air, but not too tight to inhibit free exchange of oxygen to the rolls.

The buckets are incubated in the growth chamber at 23° C. for three days. The chamber is set up for 65% humidity with no light cycle. For the cold stress treatment the buckets are then incubated in a growth chamber at 12° C. for fourteen days. The chamber is set up for 65% humidity with no light cycle. For the warm treatment the buckets are incubated at 23° C. for an additional three days.

After the appropriate treatment the germination papers are unrolled and the seeds are repositioned on the wax pencil line, if necessary. Seeds that did not germinate are discarded. The tip of the radicle and coleoptile are marked on the germination paper. The germination papers are allowed to dry and then the lengths of the radicle and coleoptile for each seed are measured and the data is recorded. This process can be facilitated using an automated caliper for electronic data transfer to a PC. A coleoptile sample is collected from six individual kernels of each entry for confirming the expression of genes of the present invention.

Statistical differences in the length of radical and shoot during pre-shock and cold shock are used for an estimation of the effect of the cold treatment on corn plants. The analysis is conducted independently for the warm and cold treatments.

Example 20

This example describes a wilt assay for transgenic plants of the present invention. 150 seeds from each event and a control set are imbibed by soaking in sterile water overnight. Imbibed seeds are rolled in germination paper. The seeds are placed in 3 rows on one piece of wet 38 lb 11.5'×30" seed paper (Anchor Paper, St. Paul, Minn.) and overlayed with a second wet piece of seed paper. The wet papers are then placed on a 12"×36" piece of wax paper from Anchor Paper, rolled up and fastened with a rubber band. The roll is placed in a 5 Liter Nalgene Pitcher with approximately 1 liter of water and allowed to germinate for 46-50 hours in a growth chamber or a greenhouse. The growth chamber is set with a day/night cycle of 16 hrs/8 hrs and 26° C. daytime/20° nighttime temperatures. The light intensity of the growth chamber is kept at 500 uE/m2-min.

One day before planting, pots are prepared for planting germinated seed. 5.25" square pots (Hummert Cat. No 129300) are filled with dry standard greenhouse media mix (peat moss mix) and adjusted to 330±5 grams by hand compacting the soil and hand watered thoroughly. After watering 1 germinated seed/pot is planted. Seedlings are allowed to grow for 1 week. During this period pots are watered by a capillary matting watering system. A capillary mat (Hummerts Cat. No. 18-4046) is placed on top of a piece of plywood that overlays the greenhouse bench (6 ft.×12 ft.). Watering is done every three hours, beginning at 7.00 AM, five times a day for 12-minute interval using seven 2 GPH (gallons per hour) pressure compensating drippers (Hummerts Cat. # 18-4046) per bench. After one week of growth, the V1 leaf is sampled by taking a leaf tear of approximately 2 square centimeters. This leaf sample from the plant is used to determine the presence of the selectable marker, CP4. Water is turned off for several days (usually over the weekend). After 10 days plants of 8-9 cm height are selected based on the presence and absence of the CP4 gene using standard methods. For each transformation an equal number (24) of transgenic and wild type plants are selected based on matched height. These plants are placed alternating a gene positive plant with a gene negative plant on the capillary mat in a serpentine fashion and subjected to dry treatment as described. After arranging plants as per above description, 8 wettest looking pots are weighed to determine maximum current pot weight. This "maximum current pot weight" is used to calibrate all other pots by adding a desired amount of water to bring them all up to the same weight. 8 random pots are weighed every day to monitor pot weight. When the average pot weight is between 600 to 700 grams this is defined as the first day of the experiment. The height of all plants is taken as the length in cm from the top of the soil to the tip of the longest leaf on the start day of the experiment.

After start of the experiment, 8 pots from different flats are weighed. Plants are allowed to grow without any watering if the average weight of pots is greater than 500 grams. If the average weight is less than 500 grams but greater than 365 grams then 35 ml of water/pot is added. If the average weight is less than 365 grams then enough water is added to bring pot weight to 400 grams assuming that each ml of water weighs 1 gram The treatment ends when the pots have had an average weight below 500 g for 7 days. On the $8^{th}$ day when the plants weigh less than 500 grams, all plants are measured for height in cm. The difference between the height at the end of the dry treatment and the height at the beginning of the dry treatment is the key quantitative phenotype of interest for this experiment. After the first dry treatment all plants are fully watered for three days and measured again to document drought recovery.

For the second round of drought and recovery estimation plants are allowed to dry by turning off the water system for seven days. After seven days plants will develop severe drought stress exhibited by 10-25% of the plants where leaves will lean to touch the top of pots. At this stage all plants are measured and allowed to recover from stress by fully watering and resuming normal growth conditions. During the recovery phase all plants are daily monitored for recovery signs indicated by a flattening of inner whorl leaves.

After 7 days of recovery all plants are measured and sampled for protein expression analysis prior to harvesting. Harvested plants are placed in vented cellophane bags and weighed to determine the fresh weight of the plants. After determining fresh weight, plants are dried for approximately four weeks in a seed drier at ~90° F., 20-40% humidity and weighed to determine the dry weight of plants.

We claim:

1. A method of generating a transgenic plant with enhanced tolerance to environmental stress comprising introducing into the plant a DNA construct comprising a promoter that functions in crop plants, operably linked to a DNA molecule selected from the group consisting of: a) a DNA molecule that encodes a polypeptide sequence at least 90% identical to SEQ ID NO:4 and b) a DNA molecule comprising the polynucleotide sequence of SEQ ID NO:3; wherein said transgenic plant exhibits enhanced stress tolerance compared to a plant of a same plant species not transformed to contain said DNA construct.

2. The method of claim 1, wherein said promoter is a plant virus promoter.

3. The method of claim 1, wherein said promoter comprises a heterologous plant promoter.

4. The method of claim 1, wherein said enhanced stress tolerance is cold stress tolerance.

5. The method of claim 1, wherein said enhanced stress tolerance is water stress tolerance.

6. The method of claim 1, wherein said plant is selected from the group consisting of corn, soybean, wheat, cotton, rice and rapeseed/canola.

7. A transgenic plant transformed with a DNA construct, wherein said DNA construct comprises a promoter that functions in crop plants, operably linked to a DNA molecule selected from the group consisting of:
   a) a DNA molecule that encodes a polypeptide sequence at least 90% identical to SEQ ID NO:4 and
   b) a DNA molecule comprising the polynucleotide sequence of SEQ ID NO:3, wherein the plant exhibits enhanced abiotic stress tolerance compared to a plant of a same plant species not transformed to contain said DNA construct.

8. The transgenic plant of claim 7, wherein said enhanced stress tolerance is cold tolerance.

9. The transgenic plant of claim 7, wherein said enhanced stress tolerance is water stress tolerance.

10. The progeny of said transgenic plant of claim 7, wherein the progeny comprises the construct.

11. The transgenic plant of claim 7 wherein said transgenic plant is selected from the group consisting of corn, soybean, wheat, cotton, rice and rapeseed/canola.

12. A plant part produced by said transgenic plant of claim 7 comprising leaves, roots, stems, shoot, flowers, fibers, fruit, or seed.

13. The transgenic plant of claim 7, wherein said DNA construct comprises a DNA molecule that encodes a polypeptide sequence at least 90% identical to SEQ ID NO:4.

14. A method of generating a transgenic crop plant with enhanced tolerance to cold stress comprising the steps of: a) transforming a plant cell with a DNA construct comprising a promoter that functions in crop plants, operably linked to a DNA molecule selected from the group consisting of: a) a DNA molecule that encodes a polypeptide sequence at least 90% identical to SEQ ID NO:4 and b) a DNA molecule comprising the polynucleotide sequence of SEQ ID NO:3; and b) regenerating said plant cell into a fertile transgenic crop plant; and c) selecting said fertile transgenic crop plant containing said DNA construct; wherein said crop plant exhibits enhanced cold stress tolerance compared to a plant of a same plant species not transformed to contain said DNA construct.

15. The transgenic plant of claim 7, wherein said DNA construct comprises the polynucleotide sequence of SEQ ID NO:3.

16. The transgenic plant of claim 7, wherein said DNA construct comprises a DNA molecule encoding a polypeptide of SEQ ID NO:4.

* * * * *

SEQUENCE LISTING

```
<160> NUMBER OF SEQ ID NOS: 51

<210> SEQ ID NO 1
<211> LENGTH: 1563
<212> TYPE: DNA
<213> ORGANISM: Oryza sativa

<400> SEQUENCE: 1
atgctgatgg cgaccgtctc gccggcgcgg agggagccga cgccgcaggc ggtgcgggcg      60
tccccgatgc catcggcggc ggcggcgttg gtgaggagag gcggtggtgg tagcggggg     120 acggtgctgg ggaagtacga gctggggcgc gtcctgggac agggctcgtt cgcgaaggtg     180
taccaggcga ggcacctgga gaccgacgag tgcgtggcaa tcaaggtgct cgacaaggag     240
aaggccgtga agggcgggat ggtccacctc gtcaagcgcg agatcaacgt gctccgccgg     300
gtgcgccacc cgaacatcgt gcagctgttc gaggtaatgg ccagcaagac caagatctac     360
ttcgtcatgg agtatgtccg cggcggcgag ctcttctccc gcgtctccaa gggacgcctc     420
agggaggaca ccgcgcggcg ctacttccag cagcttgtct ccgccgtcga cttctgccac     480
gcccgcggcg tgttccaccg tgacctcaag cccgagaacc tcctcgtgga tgagaacggg     540
```

```
gacttgaagg tctcggactt cggcctcgcc gccggccccg accagttcga ccccgacggt    600
ctgctccaca cgttctgcgg cacgccggct tacgtcgccc ccgaggtgct caggcgccgc    660
ggatacgacg cgccaaggc ggacatatgg tcatgcggtg tcatcctctt tgcgctcatg     720
gccgggtacc tccctttcca tgaccacaac atcatggttc tgtaccggaa gatctacaat    780
ggggagttca ggtgtccaag gtggttctcc aaggattta ctagattgat aacgcgcctt     840
cttgacgcaa accccaaaac taggatcacc gtgccagaga tcattgagag cgattggttc    900
aagaaaggat acaagccagt caagttttac attgaggatg acaagctcta caacctgtct    960
gatgacgtgc tgaacttgga gcctgctgat cctgttcccc caccattggg tttggcacct    1020
cctgttcctc cacctccaca agggatgat cctgatggtt cagggtctga gtcagattca     1080
tcagtcgtat cctgcccggc acattgtca actggggaga gccagagagt ccgtgggtca    1140
ctaccacgcc cagcaagcct taatgcattt gatatcatat cattctcaaa aggattcaac    1200
ttgtctgggc tgtttgagga aggggggaac agagatcaggt ttgtatctgg tgagcccatg   1260
tctgacattg taaaaagct ggaggagatt gcaaaggtca agagcttcac agtgcggagg     1320
aaggactggc gggtgagcat agagggtaca cgcgaaggag ttaaggggcc tctaaccata    1380
ggcgcggaga tatttgagct tacaccctcc cttgtagtag tggaagtaaa agaaaggca     1440 ggtgataatg aagagtatga ggatttctgc aacatggagt tgaagccagg aatgcagcac    1500
cttgtgcacc agatgctccc agctccaaat ggaactcctg tgagtgagaa ggttgaaagg    1560
taa                                                                 1563
```

<210> SEQ ID NO 2
<211> LENGTH: 521
<212> TYPE: PRT
<213> ORGANISM: Oryza sativa

<400> SEQUENCE: 2

```
Met Leu Met Ala Thr Val Ser Pro Ala Arg Arg Glu Pro Thr Pro Gln
1               5                   10                  15

Ala Val Arg Ala Ser Pro Met Pro Ser Ala Ala Ala Leu Val Arg
            20                  25                  30

Arg Gly Gly Gly Ser Gly Gly Thr Val Leu Gly Lys Tyr Glu Leu
        35                  40                  45

Gly Arg Val Leu Gly Gln Gly Ser Phe Ala Lys Val Tyr Gln Ala Arg
    50                  55                  60

His Leu Glu Thr Asp Glu Cys Val Ala Ile Lys Val Leu Asp Lys Glu
65                  70                  75                  80

Lys Ala Val Lys Gly Gly Met Val His Leu Val Lys Arg Glu Ile Asn
                85                  90                  95

Val Leu Arg Arg Val Arg His Pro Asn Ile Val Gln Leu Phe Glu Val
            100                 105                 110

Met Ala Ser Lys Thr Lys Ile Tyr Phe Val Met Glu Tyr Val Arg Gly
        115                 120                 125

Gly Glu Leu Phe Ser Arg Val Ser Lys Gly Arg Leu Arg Glu Asp Thr
    130                 135                 140

Ala Arg Arg Tyr Phe Gln Gln Leu Val Ser Ala Val Asp Phe Cys His
145                 150                 155                 160

Ala Arg Gly Val Phe His Arg Asp Leu Lys Pro Glu Asn Leu Leu Val
                165                 170                 175

Asp Glu Asn Gly Asp Leu Lys Val Ser Asp Phe Gly Leu Ala Ala Gly
            180                 185                 190
```

Pro Asp Gln Phe Asp Pro Asp Gly Leu Leu His Thr Phe Cys Gly Thr
        195                 200                 205

Pro Ala Tyr Val Ala Pro Glu Val Leu Arg Arg Gly Tyr Asp Gly
    210                 215                 220

Ala Lys Ala Asp Ile Trp Ser Cys Gly Val Ile Leu Phe Ala Leu Met
225                 230                 235                 240

Ala Gly Tyr Leu Pro Phe His Asp His Asn Ile Met Val Leu Tyr Arg
                245                 250                 255

Lys Ile Tyr Asn Gly Glu Phe Arg Cys Pro Arg Trp Phe Ser Lys Asp
            260                 265                 270

Phe Thr Arg Leu Ile Thr Arg Leu Leu Asp Ala Asn Pro Lys Thr Arg
        275                 280                 285

Ile Thr Val Pro Glu Ile Ile Glu Ser Asp Trp Phe Lys Lys Gly Tyr
        290                 295                 300

Lys Pro Val Lys Phe Tyr Ile Glu Asp Asp Lys Leu Tyr Asn Leu Ser
305                 310                 315                 320

Asp Asp Val Leu Asn Leu Glu Pro Ala Asp Pro Val Pro Pro Leu
                325                 330                 335

Gly Leu Ala Pro Pro Val Pro Pro Pro Gln Gly Asp Asp Pro Asp
                340                 345                 350

Gly Ser Gly Ser Glu Ser Asp Ser Ser Val Val Ser Cys Pro Ala Thr
            355                 360                 365

Leu Ser Thr Gly Glu Ser Gln Arg Val Arg Gly Ser Leu Pro Arg Pro
    370                 375                 380

Ala Ser Leu Asn Ala Phe Asp Ile Ile Ser Phe Ser Lys Gly Phe Asn
385                 390                 395                 400

Leu Ser Gly Leu Phe Glu Arg Gly Asn Glu Ile Arg Phe Val Ser
                405                 410                 415

Gly Glu Pro Met Ser Asp Ile Val Lys Lys Leu Glu Glu Ile Ala Lys
                420                 425                 430

Val Lys Ser Phe Thr Val Arg Arg Lys Asp Trp Arg Val Ser Ile Glu
        435                 440                 445

Gly Thr Arg Glu Gly Val Lys Gly Pro Leu Thr Ile Gly Ala Glu Ile
    450                 455                 460

Phe Glu Leu Thr Pro Ser Leu Val Val Val Glu Val Lys Arg Lys Ala
465                 470                 475                 480

Gly Asp Asn Glu Glu Tyr Glu Asp Phe Cys Asn Met Glu Leu Lys Pro
                485                 490                 495

Gly Met Gln His Leu Val His Gln Met Leu Pro Ala Pro Asn Gly Thr
            500                 505                 510

Pro Val Ser Glu Lys Val Glu Arg Ala
        515                 520

<210> SEQ ID NO 3
<211> LENGTH: 2524
<212> TYPE: DNA
<213> ORGANISM: Oryza sativa

<400> SEQUENCE: 3
taattaatct gtcattagta aatgtttact ataacactac gctatcaaat catggtgcaa    60
ttagccttaa aagatttgtc ttgcaattta catgtaatcc gtgtaattgt tttttcctac   120
aatactccat gtatatatta aacattcgat gtgacagcat ggaaattttt gtttaggaa    180 ctaaataggg ccaaaataaa agttcacacc aaaattgaaa atttgattga aattggaatg   240

```
atgtgatgaa aaatttgaaa gtttgtgtgt gtagaaaagt tttaatgtga tggaaaagtt      300
ggaagtttga agaaaaaact ttggggagaa aacatttcaa agcgaaagcg aaatgaaact      360
ctctagagaa gagaagcccc agccgcagat attattcacg atccgttaag ctgttccccc      420
tcccttccaa cgccggccac tcgtctcctc ctcctcccac ctcccgtttc cccgcgcca       480 tcctcctccg cctcgccgcc atggccgcga ccccgccgtc gtcgcagcac cggcggccgc      540
tgtcctcctc cgcctccgcc gcctccctcg ctggcaagcc gcggggggc gggctcctgc       600 tcgggcggta cgagctcggc cgcctcctcg gccacggcac cttcgccaag gtgtaccagg      660
cgcggagcgc ggattccggg gagccggtcg cgatcaaggt gctcgacaag gagaaggcga      720
tgcggcacgg cctcgtcccg cacatcaagc gggagatcgc catcctccgc cgcgtccgcc      780
accccaacat cgtgaggctg ttcgaggtga tggccaccaa gtccaagatc tacttcgtga      840
tggagctcgt ccgcggcggg gagctgttcg gccgcgtcgc caaggggcgg ctcaaggagg      900
acaccgcgcg gcgctacttc cagcagctcg tctccgccgt cgggttctgc cacgcgcgcg      960
gcgtgttcca ccgcgacctc aagcccgaga acctcctcgt cgacgagcac ggcgacctca      1020
aggtctccga cttcggcctc tccgccgtcg ccgaccagtt ccaccccgac ggcctcctcc      1080
acaccttctg cggcacgccc tcctacgtcg cgcccgaggt gctcgcgcgc cgcggctacg      1140
acggcgccaa ggcggacata tggtcctgcg gcatcatcct cttcgtgctc atggctggct      1200
accttccgtt ccatgaccag aatctcatgg ccatgtaccg aaagatttac agggggaat       1260 tccggtgccc gagatggttc tccaaggatc tttccagtct actgaatcgc atccttgaca      1320
cgaacccaga cgaaggatc actgtcaaag aggtcatgga gagcaggtgg ttccagaagg       1380
gattccggcc ggtcagattc tatgttgagg atgatcaggt tcacagcttg gcagatggtg      1440
ataatgatat gccggagttg gaacctagtg agcctcctcc tcctcctccg tttccgccgc      1500
cgccgccgca gcaagatgat gacgqtgagg agtcgggatg ggagtcggac tcatccgtgg      1560
catcatgtcc tgccacattg tcatctgagg agcgtcggca aagacctctc gggtctctca      1620 cacgccagc aagtcttaat gcgttcgata tcatatcgtt ctcaaaggga tttgatttgt       1680
cggggttgtt tgaggagcga gggagtgaag tgaggttcat atcggcagag cctatgcaaa      1740
caatcatcac aaaattggag gagatcgcaa aggtgaagag cttcttcgtt cggcgaaaag      1800
actggcgagt gagcatagaa ggcacgaggg aaggtttgaa gggtccattg acaatcggcg      1860
ctgagatatt tgagctcaca ccaagcctgg tggtagtgga ggtgaagaag aaggcagggg      1920
ataaggaaga atatgatgac ttctgtaaca gggagttgaa acctgggatg cagcatctcg      1980
tacaccatat gggatcagtt ccaaatatac cttctgatac ggagtagttt gaactaagaa      2040
aggtagttct ctttcttgga ggggtataag gaaattttgg attaaaagta tatgtctatg      2100
caagcatgaa cacctgagag gcaaaatgat acccaattcc tttagaccag tgtccatgtt      2160
ttggtgctgt tcgtttcttc aatcgaaatg atgtatgcta gtgtttgcat gctaatatca      2220
gctatcaaat gtctgttttt agctgttaca gtttaaagag agtgacaaat ctgagtatat      2280
ggcatcagta tcaatgaagt ggactagact tttatgtatg ccgcagcagt gcagccattt      2340
gtatttctat gctgccagtt agttctctga atacatatga catcaacact gaagaaatta      2400
gctcgaagtg ctctaaagaa gttctgtttt gggattaaaa ttgtaaatat agggtgaatg      2460
aataaattag acaaagcgtt agcattctaa gtatctagtt gtttattact tctgtgcatc      2520
aatt                                                                  2524
```

<210> SEQ ID NO 4
<211> LENGTH: 508
<212> TYPE: PRT
<213> ORGANISM: Oryza sativa

<400> SEQUENCE: 4

```
Met Ala Ala Thr Pro Pro Ser Ser Gln His Arg Arg Pro Leu Ser Ser
1               5                   10                  15

Ser Ala Ser Ala Ala Ser Leu Ala Gly Lys Pro Arg Gly Gly Gly Leu
            20                  25                  30

Leu Leu Gly Arg Tyr Glu Leu Gly Arg Leu Leu Gly His Gly Thr Phe
        35                  40                  45

Ala Lys Val Tyr Gln Ala Arg Ser Ala Asp Ser Gly Glu Pro Val Ala
    50                  55                  60

Ile Lys Val Leu Asp Lys Glu Lys Ala Met Arg His Gly Leu Val Pro
65                  70                  75                  80

His Ile Lys Arg Glu Ile Ala Ile Leu Arg Arg Val Arg His Pro Asn
                85                  90                  95

Ile Val Arg Leu Phe Glu Val Met Ala Thr Lys Ser Lys Ile Tyr Phe
            100                 105                 110

Val Met Glu Leu Val Arg Gly Gly Glu Leu Phe Gly Arg Val Ala Lys
        115                 120                 125

Gly Arg Leu Lys Glu Asp Thr Ala Arg Arg Tyr Phe Gln Gln Leu Val
    130                 135                 140

Ser Ala Val Gly Phe Cys His Ala Arg Gly Val Phe His Arg Asp Leu
145                 150                 155                 160

Lys Pro Glu Asn Leu Leu Val Asp Glu His Gly Asp Leu Lys Val Ser
                165                 170                 175

Asp Phe Gly Leu Ser Ala Val Ala Asp Gln Phe His Pro Asp Gly Leu
            180                 185                 190

Leu His Thr Phe Cys Gly Thr Pro Ser Tyr Val Ala Pro Glu Val Leu
        195                 200                 205

Ala Arg Arg Gly Tyr Asp Gly Ala Lys Ala Asp Ile Trp Ser Cys Gly
    210                 215                 220

Ile Ile Leu Phe Val Leu Met Ala Gly Tyr Leu Pro Phe His Asp Gln
225                 230                 235                 240

Asn Leu Met Ala Met Tyr Arg Lys Ile Tyr Arg Gly Glu Phe Arg Cys
                245                 250                 255

Pro Arg Trp Phe Ser Lys Asp Leu Ser Ser Leu Leu Asn Arg Ile Leu
            260                 265                 270

Asp Thr Asn Pro Glu Thr Arg Ile Thr Val Lys Glu Val Met Glu Ser
        275                 280                 285

Arg Trp Phe Gln Lys Gly Phe Arg Pro Val Arg Phe Tyr Val Glu Asp
    290                 295                 300

Asp Gln Val His Ser Leu Ala Asp Gly Asp Asn Asp Met Pro Glu Leu
305                 310                 315                 320

Glu Pro Ser Glu Pro Pro Pro Pro Phe Pro Pro Pro Pro
                325                 330                 335

Gln Gln Asp Asp Asp Gly Glu Glu Ser Gly Trp Glu Ser Asp Ser Ser
            340                 345                 350

Val Ala Ser Cys Pro Ala Thr Leu Ser Ser Glu Glu Arg Arg Gln Arg
        355                 360                 365

Pro Leu Gly Ser Leu Thr Arg Pro Ala Ser Leu Asn Ala Phe Asp Ile
    370                 375                 380
```

-continued

```
Ile Ser Phe Ser Lys Gly Phe Asp Leu Ser Gly Leu Phe Glu Glu Arg
385                 390                 395                 400

Gly Ser Glu Val Arg Phe Ile Ser Ala Glu Pro Met Gln Thr Ile Ile
            405                 410                 415

Thr Lys Leu Glu Glu Ile Ala Lys Val Lys Ser Phe Phe Val Arg Arg
        420                 425                 430

Lys Asp Trp Arg Val Ser Ile Glu Gly Thr Arg Glu Gly Leu Lys Gly
            435                 440                 445

Pro Leu Thr Ile Gly Ala Glu Ile Phe Glu Leu Thr Pro Ser Leu Val
    450                 455                 460

Val Val Glu Val Lys Lys Ala Gly Asp Lys Glu Glu Tyr Asp Asp
465                 470                 475                 480

Phe Cys Asn Arg Glu Leu Lys Pro Gly Met Gln His Leu Val His His
                485                 490                 495

Met Gly Ser Val Pro Asn Ile Pro Ser Asp Thr Glu
            500                 505
```

<210> SEQ ID NO 5
<211> LENGTH: 2530
<212> TYPE: DNA
<213> ORGANISM: Oryza sativa

<400> SEQUENCE: 5

```
atccatcatt agcaaatgtt tactataaca ccacgctatt aaatcatggt gcaattagcc      60
ttaaaagatt cgtcttgcaa ttgcaattta catgtaatct gtgtaattgt tttttcctac    120
aatactgcat gtatatatta acattcgat gtgacagcat gaaattttt gttttaggaa      180 ctaaacaggg ccaaaataaa agttcacacc aaaattgaaa atttgattga aattgaaatg    240
atgtgatgaa aaatttaaaa gttcgtgtgt gtaggaaagt tttaatgtga tgaaaaagtt    300
ggaagtttga agaaaaaact ttggggagaa acatttcaa agcgaaagcg aaatgaaact     360
ctctagagaa gagaagcccc agccgcagat attattcacg atccgttaag ctgttccccc    420
tcccttccaa cgccggccac tcgtctcctc ctcctcccac ctcccgtttc ctccgcgcca    480
tcctcctccg cctcggcgcc atggccgcga cccccgccgtc gtcgcgggac ccgtcgccgc    540
agcaccggcg gccgctgtcc tcctccgcct ccctcgctgg caagccgcgg ggggcgggc     600 tcctgctcgg gcggtacgag ctcggccgcc tcctcggcca cggcaccttc gccaaggtgt    660
accaggcgcg gagcgcggat tccggggagc cggtcgcgat caaggtgctc gacaaggaga    720
aggcgatgcg gcacggcctc gtcccgcaca tcaagcggga gatcgccatc ctccgccgcg    780
tccgccaccc caacatcgtg aggctgttcg aggtgatggc caccaagtcc aagatctact    840
tcgtgatgga gctcgtccgc ggcggggagc tgttcggccg cgtcgccaag gggcggctca    900
aggaggacac cgcgcggcgc tacttccagc agctcgtctc cgccgtcggg ttctgccacg    960
cgcgcggcgt gttccaccgc gacctcaagc ccgagaacct cctcgtcgac gagcacggcg   1020
acctcaaggt ctccgacttc ggcctctccg ccgtcgccga ccagttccac ccgacggcc    1080 tcctccacac cttctgcggc acgccctcct acgtcgcgcc cgaggtgctc gcgcgccgcg   1140
gctacgacgg cgccaaggcg gacatatggt cctgcggcat catcctcttc gtgctcatgg   1200
ctggctacct tccgttccat gaccagaatc tcatggccat gtaccgaaag atttacaggg   1260
gggaattccg gtgcccgaga tggttctcca aggatctttc cagtctactg aatcgcatcc   1320
ttgacacgaa cccagagaca aggatcactg tcaaagaggt catggagagc aggtggttcc   1380
```

-continued

```
agaagggatt ccggccggtc agattctatg ttgaggatga tcaggttcac agcttggcag    1440
atggtgataa tgatatgccg gagttggaac ctagtgagcc tcctcctcct cctccgtttc    1500
cgccgccgcc gccgcagcaa gatgatgacg gtgaggagtc gggatgggag tcggactcat    1560
ccgtggcatc atgtcctgcc acattgtcat ctgaggagc tcggcaaaga cctctcgggt     1620
ctctcacacg gccagcaagt cttaatgcgt tcgatatcat atcgttctca aagggatttg    1680
atttgtcggg gttgtttgag gagcgaggga gtgaagtgag gttcatatcg gcagagccta    1740
tgcaaacaat catcacaaaa ttggaggaga tcgcaaaggt gaagagcttc ttcgttcggc    1800
gaaaagactg gcgagtgagc atagaaggca cgagggaagg tttgaagggt ccattgacaa    1860
tcagcgctga gatatttgag ctcacaccaa gcctggtggt agtggaggtg aagaagaagg    1920
caggggataa ggaagaatat gatgacttct gtaacaggga gttgaaacct gggatgcagc    1980
atctcgtaca ccatatggga tcagttccaa ataccttc tgatacggag tagtttgaac      2040
taagaaaggt agttctcttt cttggagggg tataaggaaa ttttggatta aaagtatatg    2100
tctatgcaag catgaacacc tgagaggcaa atgataccc aattcctta gaccagtgtc      2160 catgttttgg tgctgttcgt ttcttcaatc gaaatgatgt atgctagtgt ttgcatgcta    2220
atatcagcta tcaaatgtct gtttttagct gttacagttt aaagagagtg acaaatctga    2280
gtatatggca tcagtatcaa tgaagtggac tagacttta tgtatgccgc agcagtgcag     2340
ccatttgtat ttctatgctg ccagttagtt ctctgaatac atatgacatc aacactgaag    2400
aaattagctc gaagtgctct aaagaagttc tgttttggga ttaaaattgt aaatataggg    2460
tgaatgaata aattagacaa agcgttagca ttctaagtat ctagttgttt attacttctg    2520
tgcatcaatt                                                           2530
```

<210> SEQ ID NO 6
<211> LENGTH: 510
<212> TYPE: PRT
<213> ORGANISM: Oryza sativa

<400> SEQUENCE: 6

```
Met Ala Ala Thr Pro Pro Ser Ser Arg Asp Pro Ser Pro Gln His Arg
1               5                   10                  15

Arg Pro Leu Ser Ser Ala Ser Leu Ala Gly Lys Pro Arg Gly Gly
            20                  25                  30

Gly Leu Leu Leu Gly Arg Tyr Glu Leu Gly Arg Leu Leu Gly His Gly
        35                  40                  45

Thr Phe Ala Lys Val Tyr Gln Ala Arg Ser Ala Asp Ser Gly Glu Pro
    50                  55                  60

Val Ala Ile Lys Val Leu Asp Lys Glu Lys Ala Met Arg His Gly Leu
65                  70                  75                  80

Val Pro His Ile Lys Arg Glu Ile Ala Ile Leu Arg Arg Val Arg His
                85                  90                  95

Pro Asn Ile Val Arg Leu Phe Glu Val Met Ala Thr Lys Ser Lys Ile
            100                 105                 110

Tyr Phe Val Met Glu Leu Val Arg Gly Gly Glu Leu Phe Gly Arg Val
        115                 120                 125

Ala Lys Gly Arg Leu Lys Glu Asp Thr Ala Arg Arg Tyr Phe Gln Gln
    130                 135                 140

Leu Val Ser Ala Val Gly Phe Cys His Ala Arg Gly Val Phe His Arg
145                 150                 155                 160

Asp Leu Lys Pro Glu Asn Leu Leu Val Asp Glu His Gly Asp Leu Lys
```

165                 170                 175
Val Ser Asp Phe Gly Leu Ser Ala Val Ala Asp Gln Phe His Pro Asp
                 180                 185                 190

Gly Leu Leu His Thr Phe Cys Gly Thr Pro Ser Tyr Val Ala Pro Glu
             195                 200                 205

Val Leu Ala Arg Arg Gly Tyr Asp Gly Ala Lys Ala Asp Ile Trp Ser
         210                 215                 220

Cys Gly Ile Ile Leu Phe Val Leu Met Ala Gly Tyr Leu Pro Phe His
225                 230                 235                 240

Asp Gln Asn Leu Met Ala Met Tyr Arg Lys Ile Tyr Arg Gly Glu Phe
                 245                 250                 255

Arg Cys Pro Arg Trp Phe Ser Lys Asp Leu Ser Ser Leu Leu Asn Arg
             260                 265                 270

Ile Leu Asp Thr Asn Pro Glu Thr Arg Ile Thr Val Lys Glu Val Met
         275                 280                 285

Glu Ser Arg Trp Phe Gln Lys Gly Phe Arg Pro Val Arg Phe Tyr Val
     290                 295                 300

Glu Asp Asp Gln Val His Ser Leu Ala Asp Gly Asp Asn Asp Met Pro
305                 310                 315                 320

Glu Leu Glu Pro Ser Glu Pro Pro Pro Pro Phe Pro Pro
                 325                 330                 335

Pro Pro Gln Gln Asp Asp Gly Glu Ser Gly Trp Glu Ser Asp
             340                 345                 350

Ser Ser Val Ala Ser Cys Pro Ala Thr Leu Ser Ser Glu Glu Arg Arg
         355                 360                 365

Gln Arg Pro Leu Gly Ser Leu Thr Arg Pro Ala Ser Leu Asn Ala Phe
     370                 375                 380

Asp Ile Ile Ser Phe Ser Lys Gly Phe Asp Leu Ser Gly Leu Phe Glu
385                 390                 395                 400

Glu Arg Gly Ser Glu Val Arg Phe Ile Ser Ala Glu Pro Met Gln Thr
                 405                 410                 415

Ile Ile Thr Lys Leu Glu Glu Ile Ala Lys Val Lys Ser Phe Phe Val
             420                 425                 430

Arg Arg Lys Asp Trp Arg Val Ser Ile Glu Gly Thr Arg Glu Gly Leu
         435                 440                 445

Lys Gly Pro Leu Thr Ile Ser Ala Glu Ile Phe Glu Leu Thr Pro Ser
     450                 455                 460

Leu Val Val Val Glu Val Lys Lys Lys Ala Gly Asp Lys Glu Glu Tyr
465                 470                 475                 480

Asp Asp Phe Cys Asn Arg Glu Leu Lys Pro Gly Met Gln His Leu Val
                 485                 490                 495

His His Met Gly Ser Val Pro Asn Ile Pro Ser Asp Thr Glu
             500                 505                 510

<210> SEQ ID NO 7
<211> LENGTH: 1700
<212> TYPE: DNA
<213> ORGANISM: Zea mays

<400> SEQUENCE: 7
taccctcgag gccggcctcc tccgcggggc cgccaagcg cgtgggcctt ctgctcggcc    60
gctacgagct gggccgcctg ctcggccacg gcaccttcgc caaggtctac cacgcccgcc   120
aagccgacac cggcgagacc gtcgccatca aggtgctcga caaggagaag gccctccgca   180

-continued

```
acggcctcgt cccgcacatc aagcgcgaga tcgccatcct ccgccgcgtg cgccacccca      240
atatcgtccg cctcttcgag gtcatggcca ccaagtccaa gatctacttc gtcatggagt      300
tcgtccgcgg cggggagctc ttcgcgcgcg tcgccaaggg ccgcctcaag gaggataccg      360
cgcgaaggta cttccagcag cttatctccg ccgtcggctt ctgccacgcc cggggcgtct      420
tccaccgcga cctcaagccc gagaatctgc tcgtcgacga gcgcggcgac ctcaaggtct      480
ccgattttgg cctctcggcg gtggccgatc agttccaccc cgacggcctc ctccacacct      540
tctgtggcac gccctcctac gtcgccccgg aggtgctcgc gcgccgcggt tatgacggcg      600
ccaaggcgga catatggtcg tgtggtgtca tcctgttcgt gctgatggct ggctaccttc      660
cttttcatga ccagaacctc atggcgatgt accgtaagat ctacagggg gaattccggt       720 gtccgaggtg gttttccaag gatcttagca gtctattgat tcgacttctt gacacgaacc      780
cagagaccag gatcaccgtg gctcagataa tggagagcag gtggtttaag aaagggttcc      840
gaccggtcag attctacgtc gaggatgacc aagtgcacag cttagcagac ggtgaggatg      900
aggtgccgga actggggcct agtgagcctc aactccacc tccccgcca ccaccgcaga        960 aagaggacga cggtgatgat tctggttggg aatcagactc gtctgtagca tcctgcccag     1020
ccacattgtc atcagaggag aggagacggc ctgctggatc gctcccacgg ccagtaagtc     1080
taaatgcatt tgatatcata tcattctcaa ggggattcaa tctgtcgggg ttgtttgagg     1140
agcgaggcaa tgaagtgaga tttgtctcag cacatcccat gcaaacgatt ataacaaaat     1200
tgggggagat cgcgaaggtg aagagctttg cagttcggcg gaaggactgg cgggttagct     1260
tggaaggcac gagagaaagt gaaaagggtc cattgacaat cggggctgaa gtatttgagc     1320
tcacaccaag ccttgtggtc gtggaggtga ggatgaaggc aggggacagg caagaatatg     1380 aggattttg tgagagggag ttgaagcctg ggatgcagca cctggtgcac catacaacct      1440
cggttccaga tataccttct gatactgatt agcttaaaag gtagtgtgct cttgattgga     1500
atgattgtgg tgaagaaatt tggattgaaa ggatgcacct ttctgtttca gcgtaagcat     1560
ctgtgcagga aaatgttatt catagatttc cgtagttttt ttttgttaat attcttctg     1620 caatccaaaa tgttttgcga tagtagtttt gtgctaatac caatttacaa aaaaaaaaa     1680 aaaaaagcgg ccctcgagct                                                 1700
```

<210> SEQ ID NO 8
<211> LENGTH: 489
<212> TYPE: PRT
<213> ORGANISM: Zea mays

<400> SEQUENCE: 8

```
Pro Ser Arg Pro Ala Ser Ser Ala Gly Pro Ala Lys Arg Val Gly Leu
1               5                   10                  15

Leu Leu Gly Arg Tyr Glu Leu Gly Arg Leu Leu Gly His Gly Thr Phe
            20                  25                  30

Ala Lys Val Tyr His Ala Arg Gln Ala Asp Thr Gly Glu Thr Val Ala
        35                  40                  45

Ile Lys Val Leu Asp Lys Glu Lys Ala Leu Arg Asn Gly Leu Val Pro
    50                  55                  60

His Ile Lys Arg Glu Ile Ala Ile Leu Arg Arg Val Arg His Pro Asn
65                  70                  75                  80

Ile Val Arg Leu Phe Glu Val Met Ala Thr Lys Ser Lys Ile Tyr Phe
                85                  90                  95

Val Met Glu Phe Val Arg Gly Gly Glu Leu Phe Ala Arg Val Ala Lys
```

-continued

```
            100                 105                 110
Gly Arg Leu Lys Glu Asp Thr Ala Arg Arg Tyr Phe Gln Gln Leu Ile
        115                 120                 125
Ser Ala Val Gly Phe Cys His Ala Arg Gly Val Phe His Arg Asp Leu
    130                 135                 140
Lys Pro Glu Asn Leu Leu Val Asp Glu Arg Gly Asp Leu Lys Val Ser
145                 150                 155                 160
Asp Phe Gly Leu Ser Ala Val Ala Asp Gln Phe His Pro Asp Gly Leu
                165                 170                 175
Leu His Thr Phe Cys Gly Thr Pro Ser Tyr Val Ala Pro Glu Val Leu
            180                 185                 190
Ala Arg Arg Gly Tyr Asp Gly Ala Lys Ala Asp Ile Trp Ser Cys Gly
        195                 200                 205
Val Ile Leu Phe Val Leu Met Ala Gly Tyr Leu Pro Phe His Asp Gln
    210                 215                 220
Asn Leu Met Ala Met Tyr Arg Lys Ile Tyr Arg Gly Glu Phe Arg Cys
225                 230                 235                 240
Pro Arg Trp Phe Ser Lys Asp Leu Ser Ser Leu Leu Ile Arg Leu Leu
                245                 250                 255
Asp Thr Asn Pro Glu Thr Arg Ile Thr Val Ala Gln Ile Met Glu Ser
            260                 265                 270
Arg Trp Phe Lys Lys Gly Phe Arg Pro Val Arg Phe Tyr Val Glu Asp
        275                 280                 285
Asp Gln Val His Ser Leu Ala Asp Gly Glu Asp Glu Val Pro Glu Leu
    290                 295                 300
Gly Pro Ser Glu Pro Pro Thr Pro Pro Pro Pro Pro Pro Pro Gln Lys
305                 310                 315                 320
Glu Asp Asp Gly Asp Asp Ser Gly Trp Glu Ser Asp Ser Ser Val Ala
                325                 330                 335
Ser Cys Pro Ala Thr Leu Ser Ser Glu Arg Arg Arg Pro Ala Gly
            340                 345                 350
Ser Leu Pro Arg Pro Val Ser Leu Asn Ala Phe Asp Ile Ile Ser Phe
        355                 360                 365
Ser Arg Gly Phe Asn Leu Ser Gly Leu Phe Glu Glu Arg Gly Asn Glu
    370                 375                 380
Val Arg Phe Val Ser Ala His Pro Met Gln Thr Ile Ile Thr Lys Leu
385                 390                 395                 400
Gly Glu Ile Ala Lys Val Lys Ser Phe Ala Val Arg Arg Lys Asp Trp
                405                 410                 415
Arg Val Ser Leu Glu Gly Thr Arg Glu Ser Glu Lys Gly Pro Leu Thr
            420                 425                 430
Ile Gly Ala Glu Val Phe Glu Leu Thr Pro Ser Leu Val Val Val Glu
        435                 440                 445
Val Arg Met Lys Ala Gly Asp Arg Gln Glu Tyr Glu Asp Phe Cys Glu
    450                 455                 460
Arg Glu Leu Lys Pro Gly Met Gln His Leu Val His His Thr Thr Ser
465                 470                 475                 480
Val Pro Asp Ile Pro Ser Asp Thr Asp
                485
```

<210> SEQ ID NO 9
<211> LENGTH: 1993
<212> TYPE: DNA
<213> ORGANISM: Zea mays

<400> SEQUENCE: 9

```
ccacgcgtcc gaagctgcct gcttccgctg ccggccgtgc tacctaatcg ccgcgcttgt      60
tttcccaccg cccgatggcc gccatcacgc cgccgacgca gtcggagccg tcgccgcaga     120
cggggcgccc ggcctcgtct gccgccgccg cggccaagcg tggagggggc ggggctggtg     180
ccgccggcgg gccgctgatg gggaagtacg agctggggcg cctcctgggg cacggcacct     240
tcgcgaaggt gtaccacgcg cggcacgtcg acacggggga caacgttgcc atcaaggtgc     300
tcgacaagga gaaggccgtg aagagcgggc tcgtcccgca catcaagcgc gagatcgctg     360
tgctacgccg cgtgcgccac ccgaacatcg tgcacctgtt cgaggttatg ccacgaaga     420
ctaagatcta cttcgtcatg gagctcgtcc gcggcggcga gctcttctcc cgcgtctcca     480
agggccgact cagggaggac accgcgcgcc gctacttcca gcagctcgtc tccgccgtgg     540
ggttctgcca cgcccgcggc gtcttccacc gcgacctgaa gcccgagaat ctactcgtcg     600
acgagcaggg gaacctcaag gtatcggatt ttgggctctc cgccgtcgcc gagcagttcc     660
gtcccgacgg cctgctccac accttctgcg gcacgccggc ctatgtggcc cccgaagtgc     720
tcggccgccg cgggtacgac ggcgccaagg cagatgtgtg gtcgtgcggt gtcatcctct     780
tgtgctcat ggccggatat ctccccttcc atgacaaaaa catcatggcc atgtacaaga     840
agatttacaa gggcgagttc cgctgtgcga ggtggttctc caaagacctt accagcttgc     900
tgatgcgcat tcttcacact aatcccaaca ctcggatcac tttgccggag atcatggagt     960
cccgctggtt caagaaagga ttcaagcctg tcaagttcta tatcgaggat gaccagctgc    1020
ataacgttat agatgacgaa gatggcctgt tagatatggg acctgctggt cctgttcctc    1080
caccattgcc acctccaccg ccacctctac ctccaccaaa ggttgatggt gatgaatcag    1140
ggtcggactc agactcgtcg atctcatcct gccctgcttc aatgttatct gatgagagcc    1200
aaaggccccg tggctctcta ccacgtccag caagtcttaa tgcctttgat atcatatcat    1260
tttcaagggg atttaactta tcagggttat ttgaggagaa aggggatgaa gtgaggttca    1320
tctcggctga gcccatgtca gatatcataa ccaaattgga ggacatagcg aagctgaaga    1380
gcttcaagtt gcggaggaag gactggcgca tctgcctgga gggtacaagg aaggagtta    1440
agggcatt aacaattggc gcggagatat ttgaactcac acctccccctt gtaatggtgg    1500
aggtaaaaaa gaaggcaggg gataatgaag agtacgagaa cttctgtgac aaggaattga    1560
agccagggat gcagcacctt gtccaccata tggtccgagc tccaagtatg ctgcttactg    1620
atgccaagta gatcgaaagg cttttgaactt aacaacagca cttcgcacgg agctactggt    1680
aacaggcgtg acattcagag cggcatgagg ctagaggaga cagttgagca cagcacagtt    1740
gaccagaaga gatagtcgtc ggaacaaaaa ccttgaccag ttccacagcg ctgtagtttc    1800
gcagatgatg agcagctcgg catctcatga ctgaataaac gcaatgcccg ccatggaggg    1860
agactccggt gtctttcttg tacctgagat ggttaagttg ttactcgaat gctgtatcac    1920
gagtggtgta gtcctgctat tcgtaatatt tcgattaacc atcaaaaaaa aaaaaaaaaa    1980
aaagggcggc cgc                                                        1993
```

<210> SEQ ID NO 10
<211> LENGTH: 518
<212> TYPE: PRT
<213> ORGANISM: Zea mays

<400> SEQUENCE: 10

-continued

```
Met Ala Ala Ile Thr Pro Pro Thr Gln Ser Glu Pro Ser Pro Gln Thr
1               5                   10                  15

Gly Arg Pro Ala Ser Ser Ala Ala Ala Ala Lys Arg Gly Gly
            20                  25                  30

Gly Ala Gly Ala Ala Gly Gly Pro Leu Met Gly Lys Tyr Glu Leu Gly
        35                  40                  45

Arg Leu Leu Gly His Gly Thr Phe Ala Lys Val Tyr His Ala Arg His
    50                  55                  60

Val Asp Thr Gly Asp Asn Val Ala Ile Lys Val Leu Asp Lys Glu Lys
65                  70                  75                  80

Ala Val Lys Ser Gly Leu Val Pro His Ile Lys Arg Glu Ile Ala Val
                85                  90                  95

Leu Arg Arg Val Arg His Pro Asn Ile Val His Leu Phe Glu Val Met
                100                 105                 110

Ala Thr Lys Thr Lys Ile Tyr Phe Val Met Glu Leu Val Arg Gly Gly
            115                 120                 125

Glu Leu Phe Ser Arg Val Ser Lys Gly Arg Leu Arg Glu Asp Thr Ala
    130                 135                 140

Arg Arg Tyr Phe Gln Leu Val Ser Ala Val Gly Phe Cys His Ala
145                 150                 155                 160

Arg Gly Val Phe His Arg Asp Leu Lys Pro Glu Asn Leu Leu Val Asp
                165                 170                 175

Glu Gln Gly Asn Leu Lys Val Ser Asp Phe Gly Leu Ser Ala Val Ala
            180                 185                 190

Glu Gln Phe Arg Pro Asp Gly Leu Leu His Thr Phe Cys Gly Thr Pro
    195                 200                 205

Ala Tyr Val Ala Pro Glu Val Leu Gly Arg Arg Gly Tyr Asp Gly Ala
210                 215                 220

Lys Ala Asp Val Trp Ser Cys Gly Val Ile Leu Phe Val Leu Met Ala
225                 230                 235                 240

Gly Tyr Leu Pro Phe His Asp Lys Asn Ile Met Ala Met Tyr Lys Lys
                245                 250                 255

Ile Tyr Lys Gly Glu Phe Arg Cys Ala Arg Trp Phe Ser Lys Asp Leu
            260                 265                 270

Thr Ser Leu Leu Met Arg Ile Leu His Thr Asn Pro Asn Thr Arg Ile
    275                 280                 285

Thr Leu Pro Glu Ile Met Glu Ser Arg Trp Phe Lys Lys Gly Phe Lys
290                 295                 300

Pro Val Lys Phe Tyr Ile Glu Asp Asp Gln Leu His Asn Val Ile Asp
305                 310                 315                 320

Asp Glu Asp Gly Leu Leu Asp Met Gly Pro Ala Gly Pro Val Pro Pro
                325                 330                 335

Pro Leu Pro Pro Pro Pro Pro Leu Pro Pro Lys Val Asp Gly
            340                 345                 350

Asp Glu Ser Gly Ser Asp Ser Asp Ser Ser Ile Ser Ser Cys Pro Ala
            355                 360                 365

Ser Met Leu Ser Asp Glu Ser Gln Arg Pro Arg Gly Ser Leu Pro Arg
    370                 375                 380

Pro Ala Ser Leu Asn Ala Phe Asp Ile Ile Ser Phe Ser Arg Gly Phe
385                 390                 395                 400

Asn Leu Ser Gly Leu Phe Glu Glu Lys Gly Asp Glu Val Arg Phe Ile
                405                 410                 415

Ser Ala Glu Pro Met Ser Asp Ile Ile Thr Lys Leu Glu Asp Ile Ala
```

```
                420             425             430
Lys Leu Lys Ser Phe Lys Leu Arg Arg Lys Asp Trp Arg Ile Cys Leu
            435                 440                 445

Glu Gly Thr Arg Glu Gly Val Lys Gly Pro Leu Thr Ile Gly Ala Glu
        450                 455                 460

Ile Phe Glu Leu Thr Pro Pro Leu Val Met Val Glu Val Lys Lys Lys
465                 470                 475                 480

Ala Gly Asp Asn Glu Glu Tyr Glu Asn Phe Cys Asp Lys Glu Leu Lys
                485                 490                 495

Pro Gly Met Gln His Leu Val His His Met Val Arg Ala Pro Ser Met
            500                 505                 510

Leu Leu Thr Asp Ala Lys
        515

<210> SEQ ID NO 11
<211> LENGTH: 863
<212> TYPE: DNA
<213> ORGANISM: Zea mays
<220> FEATURE:
<221> NAME/KEY: misc_feature
<222> LOCATION: (635)..(635)
<223> OTHER INFORMATION: n is a, c, g, or t
<220> FEATURE:
<221> NAME/KEY: misc_feature
<222> LOCATION: (701)..(701)
<223> OTHER INFORMATION: n is a, c, g, or t
<220> FEATURE:
<221> NAME/KEY: misc_feature
<222> LOCATION: (817)..(817)
<223> OTHER INFORMATION: n is a, c, g, or t
<220> FEATURE:
<221> NAME/KEY: misc_feature
<222> LOCATION: (820)..(820)
<223> OTHER INFORMATION: n is a, c, g, or t

<400> SEQUENCE: 11
cggacgcgtg ggtggagagc aggtggtgta agaaagggtt ccgaccggtc agattctacg      60
tcgaggatgt ccgagtgcac agcttagcag actggtgacg atgaggcgcc ggaactgagg     120
ctcactgtca ctgggcctcc accccacct ctctctgtgg tggtggtggt ggtggcgcgg      180
gagggagagg acgacggcga tgattctggc tgggagtcag actcctctgt agcatcctgc     240
ccagccacat tgtcatcaga ggaaaggaga cggcctgtcg gatcgctccc acggccagta     300
agtctaaacg cgtttgatat catctcattc tcaaggggat tcaatctgtc ggggttgttc     360
gaggagcgag gcaatgaagt gagatttgtc tcagcacatc ccatgcaaac gatcataacg     420
aaactggagg agatcgcgaa ggtgaagagc tttgcagttc ggcggaagga ctggcgggtt     480
agcttggaag gcacgagaga aagtgaaaag ggtccattga caatcggggc tgaagtattt     540
gagctcacac caagccttgt ggtcgtggag gtgaggatga aggcagggga caggcaagaa     600
tatgaggatt tttgtgagag ggagttgaaa cctgngatgc agcacctggt gcaccataca     660
gcctcggttc cagatatacc ttctgatact gattagctta naaggtagtg tgctcttgat     720
tggaatgatt gtggtgaaga aatttggatt gaaaggatgc acctttctgt ttcagcgtaa     780
gcatctgtgc aggaaaatgt tattcataga tttccgnagn ttttttttg taatattctt      840 tctgcaatcc aaaatgtttt gcg                                             863

<210> SEQ ID NO 12
<211> LENGTH: 97
<212> TYPE: PRT
<213> ORGANISM: Zea mays
```

```
<220> FEATURE:
<221> NAME/KEY: misc_feature
<222> LOCATION: (78)..(78)
<223> OTHER INFORMATION: Xaa can be any naturally occurring amino acid

<400> SEQUENCE: 12

Met Gln Thr Ile Ile Thr Lys Leu Glu Glu Ile Ala Lys Val Lys Ser
1               5                   10                  15

Phe Ala Val Arg Arg Lys Asp Trp Arg Val Ser Leu Glu Gly Thr Arg
            20                  25                  30

Glu Ser Glu Lys Gly Pro Leu Thr Ile Gly Ala Glu Val Phe Glu Leu
        35                  40                  45

Thr Pro Ser Leu Val Val Glu Val Arg Met Lys Ala Gly Asp Arg
    50                  55                  60

Gln Glu Tyr Glu Asp Phe Cys Glu Arg Glu Leu Lys Pro Xaa Met Gln
65                  70                  75                  80

His Leu Val His His Thr Ala Ser Val Pro Asp Ile Pro Ser Asp Thr
                85                  90                  95

Asp

<210> SEQ ID NO 13
<211> LENGTH: 2023
<212> TYPE: DNA
<213> ORGANISM: Zea mays

<400> SEQUENCE: 13
ccacgcgtcc gcgccgcgct tgttttccca ccgcccgatg ccgccatca cgccgccgac      60 gcagtcggag ccgtcgccgc agacggggcg cccggcctcg tctgccgccg ccgcggccaa    120
gcgtggaggg ggcggggctg gtgccgccgg cgggccgctg atggggaagt acgagctggg    180
gcgcctcctg gggcacggca ccttcgcgaa ggtgtaccac gcgcggcacg tcgacacggg    240
ggacaacgtt gccatcaagg tgctcgacaa ggagaaggcc gtgaagagcg gctcgtccc     300 gcacatcaag gcgcgagatcg ctgtgctacg ccgcgtgcgc cacccgaaca tcgtgcacct    360
gttcgaggtt atggccacaa agactaagat ctacttcgtc atggagctcg tccgcggcgg    420
cgagctcttc tcccgcgtct ccaagggccg actcagggag gacaccgcgc gccgctactt    480
ccagcagctc gtctccgccg tggggttctg ccacgcccgc ggcgtcttcc accgcgacct    540
gaagcccgag aatctactcg tcgacgagca ggggaacctc aaggtatcgg attttgggct    600
ctccgccgtc gccgagcagt tccgtcccga cggcctgctc cacacttct gcggcacgcc     660 ggcctatgtg gccccgaag tgctcggccg ccgcgggtac gacggcgcca aggcagacgt     720
gtggtcgtgc ggtgtcatcc tctttgtgct catggccgga tatctccctt tccatgacaa    780
aaacatcatg gccatgtaca agaagattta caagggcgag ttccgctgtg cgaggtggtt    840
ctccaaagac cttaccagct tgctgatgcg cattcttcac actaatccca acactcggat    900
cactttgccg gagatcatgg agtcccgctg gttcaagaaa ggattcaagc ctgtcaagtt    960
ctatatcgag gatgaccagc tgcataacgt tatagatgac gaagatggcc tgttagatat   1020
gggacctgct ggtcctgttc ctccaccatt gccacctcca ccgccacctc tacctccacc   1080
aaaggttgat ggtgatgaat cagggtctga ctcagactcg tcgatctcat cctgccctgc   1140
ttcaatgtta tctgatgaga gccaaggcc ccgtggctct ctaccacgtc cagcaagtct    1200
taatgccttt gatatcatat cattttcaag gggatttaac ttatcagggt tatttgagga   1260
gaaaggggat gaagtgaggt tcatctcggc tgagcccatg tcagatatca taaccaaatt   1320
```

-continued

```
ggaggacata gcgaagctga agagcttcaa gttgcggagg aaggactggc gcatctgcct    1380
ggagggtaca agggaaggag ttaaggggcc attaacaatt ggcgcggaga tatttgaact    1440
cacacctccc cttgtaatgg tggaggtaaa aagaaggca ggggataatg aagagtacga     1500
gaacttctgt gacaaggaat tgaagccagg gatgcagcac cttgtccacc atatggtccg    1560
agctccaagt atgctgctta ctgatgccaa gtagatcgaa aggctttgaa cttaacaaca    1620
gcacttcgca cggagctact ggtaacaggc gtgacattct gagcggcatg aggctagagg    1680
agacagttga gcacagcaca gttgaccaga agagatagtc gccggaacaa aaaccttgac    1740
cagttccaca gcgctgtagt ttcgcagatg atgagcagct cggcatctca tgactgaata    1800
aacgcaatgc ccgccatgga gggagactcc ggtgtctttc ttgtacctga ggtggttaag    1860
ttgttactcg aatgctgtat cacgagtggt gtagtcctgc tattcgtaat atttcgatta    1920
accatcaaaa aaaaaaaaaa aaaaaaaaaa aaaaaaaaaa aaaaaaaaaa aaaaaaaaaa    1980
aaaaaaaaaa aaaaaaaaaa aaaaaaaaaa aaagggcggc cgc                      2023
```

<210> SEQ ID NO 14
<211> LENGTH: 518
<212> TYPE: PRT
<213> ORGANISM: Zea mays

<400> SEQUENCE: 14

```
Met Ala Ala Ile Thr Pro Pro Thr Gln Ser Glu Pro Ser Pro Gln Thr
  1               5                  10                  15

Gly Arg Pro Ala Ser Ala Ala Ala Ala Lys Arg Gly Gly Gly
             20                  25                  30

Gly Ala Gly Ala Ala Gly Gly Pro Leu Met Gly Lys Tyr Glu Leu Gly
         35                  40                  45

Arg Leu Leu Gly His Gly Thr Phe Ala Lys Val Tyr His Ala Arg His
     50                  55                  60

Val Asp Thr Gly Asp Asn Val Ala Ile Lys Val Leu Asp Lys Glu Lys
 65                  70                  75                  80

Ala Val Lys Ser Gly Leu Val Pro His Ile Lys Arg Glu Ile Ala Val
                 85                  90                  95

Leu Arg Arg Val Arg His Pro Asn Ile Val His Leu Phe Glu Val Met
            100                 105                 110

Ala Thr Lys Thr Lys Ile Tyr Phe Val Met Glu Leu Val Arg Gly Gly
        115                 120                 125

Glu Leu Phe Ser Arg Val Ser Lys Gly Arg Leu Arg Glu Asp Thr Ala
    130                 135                 140

Arg Arg Tyr Phe Gln Gln Leu Val Ser Ala Val Gly Phe Cys His Ala
145                 150                 155                 160

Arg Gly Val Phe His Arg Asp Leu Lys Pro Glu Asn Leu Leu Val Asp
                165                 170                 175

Glu Gln Gly Asn Leu Lys Val Ser Asp Phe Gly Leu Ser Ala Val Ala
            180                 185                 190

Glu Gln Phe Arg Pro Asp Gly Leu Leu His Thr Phe Cys Gly Thr Pro
        195                 200                 205

Ala Tyr Val Ala Pro Glu Val Leu Gly Arg Arg Gly Tyr Asp Gly Ala
    210                 215                 220

Lys Ala Asp Val Trp Ser Cys Gly Val Ile Leu Phe Val Leu Met Ala
225                 230                 235                 240

Gly Tyr Leu Pro Phe His Asp Lys Asn Ile Met Ala Met Tyr Lys Lys
                245                 250                 255
```

-continued

```
Ile Tyr Lys Gly Glu Phe Arg Cys Ala Arg Trp Phe Ser Lys Asp Leu
            260                 265                 270
Thr Ser Leu Leu Met Arg Ile Leu His Thr Asn Pro Asn Thr Arg Ile
        275                 280                 285
Thr Leu Pro Glu Ile Met Glu Ser Arg Trp Phe Lys Lys Gly Phe Lys
    290                 295                 300
Pro Val Lys Phe Tyr Ile Glu Asp Gln Leu His Asn Val Ile Asp
305                 310                 315                 320
Asp Glu Asp Gly Leu Leu Asp Met Gly Pro Ala Gly Pro Val Pro Pro
                325                 330                 335
Pro Leu Pro Pro Pro Pro Pro Leu Pro Pro Lys Val Asp Gly
            340                 345                 350
Asp Glu Ser Gly Ser Asp Ser Asp Ser Ser Ile Ser Ser Cys Pro Ala
                355                 360                 365
Ser Met Leu Ser Asp Glu Ser Gln Arg Pro Arg Gly Ser Leu Pro Arg
        370                 375                 380
Pro Ala Ser Leu Asn Ala Phe Asp Ile Ile Ser Phe Ser Arg Gly Phe
385                 390                 395                 400
Asn Leu Ser Gly Leu Phe Glu Glu Lys Gly Asp Glu Val Arg Phe Ile
            405                 410                 415
Ser Ala Glu Pro Met Ser Asp Ile Ile Thr Lys Leu Glu Asp Ile Ala
        420                 425                 430
Lys Leu Lys Ser Phe Lys Leu Arg Arg Lys Asp Trp Arg Ile Cys Leu
    435                 440                 445
Glu Gly Thr Arg Glu Gly Val Lys Gly Pro Leu Thr Ile Gly Ala Glu
450                 455                 460
Ile Phe Glu Leu Thr Pro Pro Leu Val Met Val Glu Val Lys Lys Lys
465                 470                 475                 480
Ala Gly Asp Asn Glu Glu Tyr Glu Asn Phe Cys Asp Lys Glu Leu Lys
                485                 490                 495
Pro Gly Met Gln His Leu Val His His Met Val Arg Ala Pro Ser Met
        500                 505                 510
Leu Leu Thr Asp Ala Lys
        515
```

<210> SEQ ID NO 15
<211> LENGTH: 2022
<212> TYPE: DNA
<213> ORGANISM: Glycine max

<400> SEQUENCE: 15

```
tgaagctcca tcaccactag cgaacacttc cattgttttt atctcacagg atcgatcgat    60
atcaccagca tcaccatggc agaggtggcg ccgccgaaga aggaaaaccc gaaccttctc   120
ctggggcggt cgagctcgg gaagctcctc gggcacggaa ccttcgcgaa ggtccaccac   180
gcgcgcaaca tcaaaaccgg agaaggagtc gccatcaaga tcatcaacaa ggagaaaatc   240
ctaaagggg gtttggtctc ccacataaag cgcgagatct ccattctccg gcgcgtgcgc   300
caccccaaca tcgtgcaact cttcgaagtg atggccacca agaccaagat ctacttcgtc   360
atggagtacg tgcgtggcgg cgaactcttc aacaaggtcg caagggaag attaaaagaa   420
gaagttgcga gaaattactt tcagcagtta gtttccgcgg tggagttttg ccacgcgcgc   480
ggcgtgttcc acagggacct gaagcccgag aacctgttgc tggacgagga tgggaacctt   540
aaagtctccg actttggtct cagtgccgtg tcggatcaga taaggcagga cgggctgttc   600
```

-continued

```
cacacgtttt gtgggacacc tgcgtatgtt gctcctgagg tcttgtcgcg gaaaggctac      660
gatggtgcaa aggttgatat ttggtcttgt ggggttgttt tgtttgttct gatggccggc      720
tatttgccct tcaatgaccg taacgttatg gctatgtata agaagattta caagggtgag      780
tttcggtgtc ccaggtggtt ttcttctgaa cttacaagac ttctctctag gcttcttgat      840
actaaccctc agacaaggat ttctattcct gaagtcatgg agaatcgctg gttcaagaag      900
ggtttcaagc agattaagtt ttatgtggag gatgatagag tttgtagttt tgacgagaaa      960
ctgttacttc atcatgatga tgatttggca acatcggatt ctgaggttga gattaggagg     1020
aagaatagta atggttcgtt gccgaggcct gcgagtttga atgcgtttga catcatatcg     1080
ttttctcagg gctttgatct atcagggttg tttgaggaaa agggtgatga ggcgaggttt     1140
gtgtcatctg ctccggtgtc gaagattata tcaaaattgg aggaggttgc tcagttggtt     1200
agtttcagtg tgaggaagaa agattgcagg gtgagcttgg aggggtgtag agaaggtgtg     1260
aaggggcctt tgactattgc tgctgaggtt tttgagttga ccttccttgg tggtggtg     1320 gaggtcaaga aaaagggagg ggataaggcc gagtatgaga agttttgtaa ctctgagttg     1380
agacccgcgt tggagaattt agggatggag gaatctgctt cttcttcttc ttcttgtcat     1440
caatctacac acactcaatc tgaattccaa caacatcgaa cactttctga ctctgccctt     1500
aacagacatt cagataatga atgtttgttc gaacgagagt taggtctagc agatgagact     1560
agtatctcac aacatggtga atcaaagttc gaatgtcaac aggaaaatat ggccatgttt     1620
actatctgac catgtcttga gcactatgat tgtttccaaa gaatgaaaac aaaaaagata     1680
atgaatgctt gcattaatta aggtagcagg agaatgacag aagatgatag catactattt     1740
ctctcttgtt gttttaggct gtgtgtaagt taaattttac tttcttttc cctcgagaat     1800 tttccggcat ttttaggttt gctccttgac tggagcatta gattctactg tatttgtatg     1860
tccaaatgtt gtgtttctgt aaggctaatt taatttaaat atagtgaatg aagtgtacat     1920
gtcaacagtt cacatgtctt ggtaaattgc tctgtaactg tatttatttc cattctttat     1980
tgcaagtaat gagaaaataa taatgcaact ttcttgtgat tc                        2022
```

<210> SEQ ID NO 16
<211> LENGTH: 517
<212> TYPE: PRT
<213> ORGANISM: Glycine max

<400> SEQUENCE: 16

```
Met Ala Glu Val Ala Pro Pro Lys Lys Glu Asn Pro Asn Leu Leu Leu
1               5                   10                  15

Gly Arg Phe Glu Leu Gly Lys Leu Leu Gly His Gly Thr Phe Ala Lys
            20                  25                  30

Val His His Ala Arg Asn Ile Lys Thr Gly Glu Gly Val Ala Ile Lys
        35                  40                  45

Ile Ile Asn Lys Glu Lys Ile Leu Lys Gly Gly Leu Val Ser His Ile
    50                  55                  60

Lys Arg Glu Ile Ser Ile Leu Arg Arg Val His Pro Asn Ile Val
65                  70                  75                  80

Gln Leu Phe Glu Val Met Ala Thr Lys Thr Lys Ile Tyr Phe Val Met
                85                  90                  95

Glu Tyr Val Arg Gly Gly Glu Leu Phe Asn Lys Val Ala Lys Gly Arg
            100                 105                 110

Leu Lys Glu Glu Val Ala Arg Asn Tyr Phe Gln Gln Leu Val Ser Ala
```

```
            115                 120                 125
Val Glu Phe Cys His Ala Arg Gly Val Phe His Arg Asp Leu Lys Pro
130                 135                 140

Glu Asn Leu Leu Leu Asp Glu Asp Gly Asn Leu Lys Val Ser Asp Phe
145                 150                 155                 160

Gly Leu Ser Ala Val Ser Asp Gln Ile Arg Gln Asp Gly Leu Phe His
                165                 170                 175

Thr Phe Cys Gly Thr Pro Ala Tyr Val Ala Pro Glu Val Leu Ser Arg
            180                 185                 190

Lys Gly Tyr Asp Gly Ala Lys Val Asp Ile Trp Ser Cys Gly Val Val
        195                 200                 205

Leu Phe Val Leu Met Ala Gly Tyr Leu Pro Phe Asn Asp Arg Asn Val
    210                 215                 220

Met Ala Met Tyr Lys Lys Ile Tyr Lys Gly Glu Phe Arg Cys Pro Arg
225                 230                 235                 240

Trp Phe Ser Ser Glu Leu Thr Arg Leu Leu Ser Arg Leu Leu Asp Thr
                245                 250                 255

Asn Pro Gln Thr Arg Ile Ser Ile Pro Glu Val Met Glu Asn Arg Trp
            260                 265                 270

Phe Lys Lys Gly Phe Lys Gln Ile Lys Phe Tyr Val Glu Asp Asp Arg
        275                 280                 285

Val Cys Ser Phe Asp Glu Lys Leu Leu Leu His His Asp Asp Asp Leu
    290                 295                 300

Ala Thr Ser Asp Ser Glu Val Glu Ile Arg Arg Lys Asn Ser Asn Gly
305                 310                 315                 320

Ser Leu Pro Arg Pro Ala Ser Leu Asn Ala Phe Asp Ile Ile Ser Phe
                325                 330                 335

Ser Gln Gly Phe Asp Leu Ser Gly Leu Phe Glu Glu Lys Gly Asp Glu
            340                 345                 350

Ala Arg Phe Val Ser Ser Ala Pro Val Ser Lys Ile Ile Ser Lys Leu
        355                 360                 365

Glu Glu Val Ala Gln Leu Val Ser Phe Ser Val Arg Lys Lys Asp Cys
    370                 375                 380

Arg Val Ser Leu Glu Gly Cys Arg Glu Gly Val Lys Gly Pro Leu Thr
385                 390                 395                 400

Ile Ala Ala Glu Val Phe Glu Leu Thr Pro Ser Leu Val Val Val Glu
                405                 410                 415

Val Lys Lys Lys Gly Gly Asp Lys Ala Glu Tyr Glu Lys Phe Cys Asn
            420                 425                 430

Ser Glu Leu Arg Pro Ala Leu Glu Asn Leu Gly Met Glu Glu Ser Ala
        435                 440                 445

Ser Ser Ser Ser Ser Cys His Gln Ser Thr His Thr Gln Ser Glu Phe
    450                 455                 460

Gln Gln His Arg Thr Leu Ser Asp Ser Ala Leu Asn Arg His Ser Asp
465                 470                 475                 480

Asn Glu Cys Leu Phe Glu Arg Glu Leu Gly Leu Ala Asp Glu Thr Ser
                485                 490                 495

Ile Ser Gln His Gly Glu Ser Lys Phe Glu Cys Gln Gln Glu Asn Met
            500                 505                 510

Ala Met Phe Thr Ile
            515

<210> SEQ ID NO 17
```

<211> LENGTH: 1975
<212> TYPE: DNA
<213> ORGANISM: Glycine max

<400> SEQUENCE: 17

| | | | | | |
|---|---|---|---|---|---|
| caatgaagct | ccatcaccac | tagcgaacac | ttccattgtt | tttatctcac | aggatcgatt | 60 |
| tatccccacc | accaccacca | tggcagaggt | ggcggcgccg | aagaaggaaa | acccgaatct | 120 |
| tctccttggg | cggttcgagc | tcggaaagct | cctcgggcac | ggaaccttcg | cgaaggtcca | 180 |
| ccacgcgcgc | aacatcaaaa | ccggagaagg | agtcgccatc | aagatcatca | acaaggagaa | 240 |
| aatcctaaag | ggtggtttgg | tctcccacat | caagcgcgag | atctccatcc | tccgccgcgt | 300 |
| gcgccacccc | aacatcgtgc | aactcttcga | agtcatggcc | acaaagacca | agatctactt | 360 |
| cgtcatggaa | ttcgtccgtg | gcggcgaact | cttcaacaag | gtcgcaaagg | gaaggttaaa | 420 |
| agaagaagtc | gccagaaagt | acttccaaca | gttggtttcc | gcggtggagt | tttgccacgc | 480 |
| gcgcggcgtg | ttccacaggg | atttaaagcc | cgagaatttg | ttgctggacg | aggatgggaa | 540 |
| ccttaaagtc | tccgactttg | gactcagtgc | cgtgtcggac | cagataaggc | atgacgggct | 600 |
| gttccacacg | ttttgcggaa | cacccgcgta | tgttgctcct | gaggttttgg | cgcggaaagg | 660 |
| gtacgatggt | gcaaaggttg | atatttggtc | ttgtggggtt | gttttgtttg | ttttgatggc | 720 |
| gggttatttg | cccttccatg | accgtaacgt | tatggctatg | tataagaaga | tttcaaggg | 780 |
| tgagtttcgg | tgtcccaggt | ggttttcttc | tgaacttaca | agacttttct | ctaggcttct | 840 |
| cgatactaac | cctcagacaa | ggatttctat | tcccgaaatc | atggagaatc | gctggttcaa | 900 |
| gaagggtttc | aagcagatta | agttttatgt | ggaggatgat | agagtttgta | gttttgatga | 960 |
| gaaacagctg | cagcatcatg | atggcgatga | ttatttggca | acatcggatt | ctgaggttga | 1020 |
| gattagaagg | aagaatagta | attgcaatag | tactagtaat | ggtaattcgt | tgccgaggcc | 1080 |
| tgcgagtttg | aatgcgtttg | acataatatc | gttttctcaa | ggctttgatc | tatcaggggtt | 1140 |
| gtttgaggag | aagggtgatg | aggcgaggtt | tgtgtcttct | gctccggtgt | cgaagattat | 1200 |
| atcgaaattg | gaggaggttg | ctcagttggt | tagcttcact | gtgaggaaga | aagattgcag | 1260 |
| ggtgagcttg | gaggggtgta | gagaaggtgt | gaaagggcct | ttgactattg | ctgctgagat | 1320 |
| ttttgagttg | acaccttcct | tggtggtggt | ggaggtgaag | aaaaaaggag | gggataaggc | 1380 |
| agagtatgag | aagttttgta | actctgagct | gaaacccgcg | ttggagaatt | tggggatgga | 1440 |
| ggattctgct | tcttcttctt | cttcttgtca | tcaatctaca | cacactcaat | ctgaattcca | 1500 |
| acaacaacat | cgaacatttt | ctgactctgc | ccttaacaga | cattcagata | ataatgaatg | 1560 |
| cttatatgat | caagagttgg | gtctagcaga | agagactagt | atcccacaac | ttggtgaacc | 1620 |
| aaagttcgaa | tttcaacagg | aaaatgtgcc | catgttact | atttgactgt | gtctacaaca | 1680 |
| ctattgtttt | caaagaatga | aacatgtgga | aaaccaaaaa | agataatga | atgtttgcat | 1740 |
| taattaaggt | accaggagaa | tgacagaaga | tgacaacata | ctatttctct | cttgttattt | 1800 |
| ttaggctgtg | tgtaagttaa | attttacttt | cttttcccct | caagaatttt | ccggcatttt | 1860 |
| taggtttgct | ccttgactgg | agcattagat | gctactgtat | ttctttgtcc | aaatgttgta | 1920 |
| ttattgtaag | gctaatttaa | ttttaaatat | agtgaatgaa | gaagtttata | tgtgt | 1975 |

<210> SEQ ID NO 18
<211> LENGTH: 528
<212> TYPE: PRT
<213> ORGANISM: Glycine max

<400> SEQUENCE: 18

```
Met Ala Glu Val Ala Ala Pro Lys Lys Glu Asn Pro Asn Leu Leu Leu
1               5                   10                  15

Gly Arg Phe Glu Leu Gly Lys Leu Leu Gly His Gly Thr Phe Ala Lys
            20                  25                  30

Val His His Ala Arg Asn Ile Lys Thr Gly Glu Gly Val Ala Ile Lys
        35                  40                  45

Ile Ile Asn Lys Glu Lys Ile Leu Lys Gly Gly Leu Val Ser His Ile
    50                  55                  60

Lys Arg Glu Ile Ser Ile Leu Arg Arg Val Arg His Pro Asn Ile Val
65                  70                  75                  80

Gln Leu Phe Glu Val Met Ala Thr Lys Thr Lys Ile Tyr Phe Val Met
                85                  90                  95

Glu Phe Val Arg Gly Gly Glu Leu Phe Asn Lys Val Ala Lys Gly Arg
            100                 105                 110

Leu Lys Glu Glu Val Ala Arg Lys Tyr Phe Gln Gln Leu Val Ser Ala
        115                 120                 125

Val Glu Phe Cys His Ala Arg Gly Val Phe His Arg Asp Leu Lys Pro
    130                 135                 140

Glu Asn Leu Leu Leu Asp Glu Asp Gly Asn Leu Lys Val Ser Asp Phe
145                 150                 155                 160

Gly Leu Ser Ala Val Ser Asp Gln Ile Arg His Asp Gly Leu Phe His
                165                 170                 175

Thr Phe Cys Gly Thr Pro Ala Tyr Val Ala Pro Glu Val Leu Ala Arg
            180                 185                 190

Lys Gly Tyr Asp Gly Ala Lys Val Asp Ile Trp Ser Cys Gly Val Val
        195                 200                 205

Leu Phe Val Leu Met Ala Gly Tyr Leu Pro Phe His Asp Arg Asn Val
    210                 215                 220

Met Ala Met Tyr Lys Lys Ile Tyr Lys Gly Glu Phe Arg Cys Pro Arg
225                 230                 235                 240

Trp Phe Ser Ser Glu Leu Thr Arg Leu Phe Ser Arg Leu Leu Asp Thr
                245                 250                 255

Asn Pro Gln Thr Arg Ile Ser Ile Pro Glu Ile Met Glu Asn Arg Trp
            260                 265                 270

Phe Lys Lys Gly Phe Lys Gln Ile Lys Phe Tyr Val Glu Asp Asp Arg
        275                 280                 285

Val Cys Ser Phe Asp Glu Lys Gln Leu Gln His His Asp Gly Asp Asp
    290                 295                 300

Tyr Leu Ala Thr Ser Asp Ser Glu Val Glu Ile Arg Arg Lys Asn Ser
305                 310                 315                 320

Asn Cys Asn Ser Thr Ser Asn Gly Asn Ser Leu Pro Arg Pro Ala Ser
                325                 330                 335

Leu Asn Ala Phe Asp Ile Ile Ser Phe Ser Gln Gly Phe Asp Leu Ser
            340                 345                 350

Gly Leu Phe Glu Glu Lys Gly Asp Glu Ala Arg Phe Val Ser Ser Ala
        355                 360                 365

Pro Val Ser Lys Ile Ile Ser Lys Leu Glu Glu Val Ala Gln Leu Val
    370                 375                 380

Ser Phe Thr Val Arg Lys Lys Asp Cys Arg Val Ser Leu Glu Gly Cys
385                 390                 395                 400

Arg Glu Gly Val Lys Gly Pro Leu Thr Ile Ala Ala Glu Ile Phe Glu
                405                 410                 415
```

```
Leu Thr Pro Ser Leu Val Val Glu Val Lys Lys Gly Gly Asp
            420                 425                 430

Lys Ala Glu Tyr Glu Lys Phe Cys Asn Ser Glu Leu Lys Pro Ala Leu
        435                 440                 445

Glu Asn Leu Gly Met Glu Asp Ser Ala Ser Ser Ser Ser Cys His
    450                 455                 460

Gln Ser Thr His Thr Gln Ser Glu Phe Gln Gln His Arg Thr Phe
465             470                 475                 480

Ser Asp Ser Ala Leu Asn Arg His Ser Asp Asn Glu Cys Leu Tyr
                485                 490                 495

Asp Gln Glu Leu Gly Leu Ala Glu Glu Thr Ser Ile Pro Gln Leu Gly
            500                 505                 510

Glu Pro Lys Phe Glu Phe Gln Gln Glu Asn Val Pro Met Phe Thr Ile
        515                 520                 525

<210> SEQ ID NO 19
<211> LENGTH: 1885
<212> TYPE: DNA
<213> ORGANISM: Glycine max
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (33)..(39)
<223> OTHER INFORMATION: n is a, c, g, or t
<220> FEATURE:
<221> NAME/KEY: misc_feature
<222> LOCATION: (41)..(43)
<223> OTHER INFORMATION: n is a, c, g, or t
<220> FEATURE:
<221> NAME/KEY: misc_feature
<222> LOCATION: (45)..(47)
<223> OTHER INFORMATION: n is a, c, g, or t
<220> FEATURE:
<221> NAME/KEY: misc_feature
<222> LOCATION: (49)..(52)
<223> OTHER INFORMATION: n is a, c, g, or t
<220> FEATURE:
<221> NAME/KEY: misc_feature
<222> LOCATION: (54)..(73)
<223> OTHER INFORMATION: n is a, c, g, or t

<400> SEQUENCE: 19
agagccatgc taggccttac agnacnncnc ttnnnnnnnt nnngnnnann nncnnnnnnn      60
nnnnnnnnnn nnnccaaggt gtactacgcg cgtaacatca aaaccggcga aggcgtggcc     120
atcaaggtaa tcgacaagga gaagatcctc aaaggaggtt tggtggcgca catcaagcgt     180
gagatctcta tcctgcgccg tgttcgccac cctaacatcg ttcagctctt cgaagtcatg     240
gccaccaaga gcaagatcta tttcgtaatg gaatacgttc gcggcggcga gcttttcaac     300
aaggtcgcca agggaaggct caaagaagag gtcgcgagaa agtactttca gcaattaatc     360
tctgctgtgg gattctgcca cgccagaggg gtgtaccaca gagatctcaa gcctgaaaat     420
ttgttgcttg atgagaatgg caatctcaaa gtctctgatt ttggattgag tgcggtgtct     480
gatcaaatcc gacaggatgg tcttttccac acttttgtg ggacacctgc gtatgttgct     540
```

```
cctgaggttt tggcgaggaa agggtacgat ggtgctaagg tggatctttg gtcttgtggg    600
gtggtgttgt ttgtgttgat ggcggggtat ttgccctttc atgaccagaa tgtgatggca    660
atgtataaga agatttatag agggagtttc cggtgtccga ggtggttttc tcctgatttg    720
tccaggcttc tcacaaggct tcttgatacc aagcctgaaa cccggattgc gattcctgaa    780
attatggaga ataagtggtt caagaaaggg tttaagcaga tcaagtttta tgtggaggat    840
gataggcttt gcaatgtggt ggatgatgat ggccttatgg acaatgatga tgacactgct    900
tcgattgttt ctgttgcttc gttttcggat tactcggttt ccgagtctga ttctgagatt    960
gagactagga ggaggatcaa tgctcccttg cctagacctc ctagtttgaa tgcctttgac    1020
attatatcgt tctcgccggg cttttaatctt tcggggttgt ttgaggagaa agaggatgag    1080
acaaggtttg tgactgctgc accggttaac aggatcattt ccaagctgga ggagattgct    1140
cagttggtta ggttttcggt gaggaagaag gattgcaggg tgagtttgga gggtaccaga    1200 gaggggggtta gagggccttt gactattgct gctgagatat ttgagttgac accttctttg    1260
gttgtggtgg aggtgaagaa aaaaggaggg gatagagccg agtatgagag gttttgtaac    1320
gatgagttaa agcctggatt gcagaatttg atggtggagg agtctgctac ttcttcagag    1380
ttgtctacac ctattcaacc ttccctacta cgtggccttt ctgaacctgt gccggatatt    1440
tcttctgata ttgaaaccccc gctctgtata ccttctgatg attgaagact cagatataga    1500
gaagaagaga aaaatggtta aggactttct ctctaatctc tgtatcacac acactctttc    1560
tttctctctc tctcttttt tttttatgtt atagattgtg tatggaaatt ggtaaaaaaa    1620
tttccacaca ggattgattg tcctgctttt aggtttgctt cttgactgga gcgttaggtg    1680
cctactgttt gtctaattgc catacgagaa aaaaggctaa ttgaaatata gtgaatgagt    1740
atgtatttat tttctacttt tcttggctct gtatagcaag tgataataaa aataacaaaa    1800
cggtttagtg ctaatccatg cggcattgca ctggctttgt gtttggctct atattcaagt    1860
taaataagat catttgaaat tggag    1885
```

<210> SEQ ID NO 20
<211> LENGTH: 475
<212> TYPE: PRT
<213> ORGANISM: Glycine max
<220> FEATURE:
<221> NAME/KEY: misc_feature
<222> LOCATION: (6)..(6)
<223> OTHER INFORMATION: Xaa can be any naturally occurring amino acid

<400> SEQUENCE: 20

Met Leu Gly Leu Thr Xaa Lys Val Tyr Tyr Ala Arg Asn Ile Lys Thr
1               5                   10                  15

Gly Glu Gly Val Ala Ile Lys Val Ile Asp Lys Glu Lys Ile Leu Lys
            20                  25                  30

Gly Gly Leu Val Ala His Ile Lys Arg Glu Ile Ser Ile Leu Arg Arg
        35                  40                  45

Val Arg His Pro Asn Ile Val Gln Leu Phe Glu Val Met Ala Thr Lys
    50                  55                  60

Ser Lys Ile Tyr Phe Val Met Glu Tyr Val Arg Gly Gly Glu Leu Phe
65                  70                  75                  80

Asn Lys Val Ala Lys Gly Arg Leu Lys Glu Glu Val Ala Arg Lys Tyr
                85                  90                  95

Phe Gln Gln Leu Ile Ser Ala Val Gly Phe Cys His Ala Arg Gly Val
            100                 105                 110

```
Tyr His Arg Asp Leu Lys Pro Glu Asn Leu Leu Asp Glu Asn Gly
        115                 120                 125

Asn Leu Lys Val Ser Asp Phe Gly Leu Ser Ala Val Ser Asp Gln Ile
130                 135                 140

Arg Gln Asp Gly Leu Phe His Thr Phe Cys Gly Thr Pro Ala Tyr Val
145                 150                 155                 160

Ala Pro Glu Val Leu Ala Arg Lys Gly Tyr Asp Gly Ala Lys Val Asp
                165                 170                 175

Leu Trp Ser Cys Gly Val Val Leu Phe Val Leu Met Ala Gly Tyr Leu
            180                 185                 190

Pro Phe His Asp Gln Asn Val Met Ala Met Tyr Lys Lys Ile Tyr Arg
        195                 200                 205

Gly Glu Phe Arg Cys Pro Arg Trp Phe Ser Pro Asp Leu Ser Arg Leu
    210                 215                 220

Leu Thr Arg Leu Leu Asp Thr Lys Pro Glu Thr Arg Ile Ala Ile Pro
225                 230                 235                 240

Glu Ile Met Glu Asn Lys Trp Phe Lys Lys Gly Phe Lys Gln Ile Lys
                245                 250                 255

Phe Tyr Val Glu Asp Asp Arg Leu Cys Asn Val Val Asp Asp Gly
            260                 265                 270

Leu Met Asp Asn Asp Asp Thr Ala Ser Ile Val Ser Val Ala Ser
        275                 280                 285

Phe Ser Asp Tyr Ser Val Ser Glu Ser Asp Ser Glu Ile Glu Thr Arg
    290                 295                 300

Arg Arg Ile Asn Ala Pro Leu Pro Arg Pro Pro Ser Leu Asn Ala Phe
305                 310                 315                 320

Asp Ile Ile Ser Phe Ser Pro Gly Phe Asn Leu Ser Gly Leu Phe Glu
                325                 330                 335

Glu Lys Glu Asp Glu Thr Arg Phe Val Thr Ala Ala Pro Val Asn Arg
            340                 345                 350

Ile Ile Ser Lys Leu Glu Glu Ile Ala Gln Leu Val Arg Phe Ser Val
        355                 360                 365

Arg Lys Lys Asp Cys Arg Val Ser Leu Glu Gly Thr Arg Glu Gly Val
    370                 375                 380

Arg Gly Pro Leu Thr Ile Ala Ala Glu Ile Phe Glu Leu Thr Pro Ser
385                 390                 395                 400

Leu Val Val Val Glu Val Lys Lys Lys Gly Gly Asp Arg Ala Glu Tyr
                405                 410                 415

Glu Arg Phe Cys Asn Asp Glu Leu Lys Pro Gly Leu Gln Asn Leu Met
            420                 425                 430

Val Glu Glu Ser Ala Thr Ser Ser Glu Leu Ser Thr Pro Ile Gln Pro
        435                 440                 445

Ser Leu Leu Arg Gly Leu Ser Glu Pro Val Pro Asp Ile Ser Ser Asp
    450                 455                 460

Ile Glu Thr Pro Leu Cys Ile Pro Ser Asp Asp
465                 470                 475

<210> SEQ ID NO 21
<211> LENGTH: 947
<212> TYPE: DNA
<213> ORGANISM: Gossypium hirsutum

<400> SEQUENCE: 21
cccacgcgtc cgaattaatc tcggccgttc attttttgcca cgcgcgtggc gtttaccacc      60
```

```
gtgacctgaa ggctggagaa tctacttctc gatgaaaatg gggatttgaa agtctctgat      120 ttcggggttga gtgctgtatc ggatcagatc cggcaagacg gtttgtttca cacgttttgt     180 ggaacccccgg cttttgttgc gccggaagtt ttggcgagga aaggatacga tgcggcgaaa     240
gtagatatct ggtcttgtgg agtgatttta tttgttctaa tggcagggta tttaccattt     300
caagatcaga acattatggc tatgtacaag aagatttaca agggtgagtt tcggtgtccg     360
agatggtttt cacccgagtt aattcggtta ctcaccaaac tcctagacac caacccggaa     420
acaagaatta cgattccaga aatcatggag aaacgctggt tcaaaaaggg gtttaaacat     480
attaagttct acatcgaaga tgataagtta tgcagtgtcg aagacgatga taatgatgtt    540
gggccatgtt cagaccaatc atcaatgtct gagtcagaaa cagagttgga aacgaggaaa    600
cgagttggca cattgccaag gccagctagt ttaaacgcgt tcgaccttat atctttctcc    660
ccagggttca acctatccgg gttgttcgag gaaggagaag aaggttcccg gtttgtttca    720
ggggcaccgg tttcgacaat catatcgaaa ttggaggaga tagccaaggt tgttagcttt    780
actgtgagga aaaggattg tagagtgagc ttggagggtt ctagagaagg agctaaaggt    840
ccattatcga ttgctgctga gatattcgaa ttaaccccctt cattagtcgt tgtggaagtg    900
aagaagaaag gaggtgaacg aggagagtat gaggattttt tgtaaca               947
```

<210> SEQ ID NO 22
<211> LENGTH: 313
<212> TYPE: PRT
<213> ORGANISM: Gossypium hirsutum
<220> FEATURE:
<221> NAME/KEY: misc_feature
<222> LOCATION: (24)..(24)
<223> OTHER INFORMATION: Xaa can be any naturally occurring amino acid

<400> SEQUENCE: 22

His Ala Ser Glu Leu Ile Ser Ala Val His Phe Cys His Ala Arg Gly
1               5                   10                  15

Val Tyr His Arg Asp Leu Lys Xaa Glu Asn Leu Leu Leu Asp Glu Asn
            20                  25                  30

Gly Asp Leu Lys Val Ser Asp Phe Gly Leu Ser Ala Val Ser Asp Gln
        35                  40                  45

Ile Arg Gln Asp Gly Leu Phe His Thr Phe Cys Gly Thr Pro Ala Phe
    50                  55                  60

Val Ala Pro Glu Val Leu Ala Arg Lys Gly Tyr Asp Ala Ala Lys Val
65                  70                  75                  80

Asp Ile Trp Ser Cys Gly Val Ile Leu Phe Val Leu Met Ala Gly Tyr
                85                  90                  95

Leu Pro Phe Gln Asp Gln Asn Ile Met Ala Met Tyr Lys Lys Ile Tyr
            100                 105                 110

Lys Gly Glu Phe Arg Cys Pro Arg Trp Phe Ser Pro Glu Leu Ile Arg
        115                 120                 125

Leu Leu Thr Lys Leu Leu Asp Thr Asn Pro Glu Thr Arg Ile Thr Ile
    130                 135                 140

Pro Glu Ile Met Glu Lys Arg Trp Phe Lys Lys Gly Phe Lys His Ile
145                 150                 155                 160

Lys Phe Tyr Ile Glu Asp Asp Lys Leu Cys Ser Val Glu Asp Asp
                165                 170                 175

Asn Asp Val Gly Pro Cys Ser Asp Gln Ser Ser Met Ser Glu Ser Glu
            180                 185                 190

Thr Glu Leu Glu Thr Arg Lys Arg Val Gly Thr Leu Pro Arg Pro Ala

```
              195                 200                 205
Ser Leu Asn Ala Phe Asp Leu Ile Ser Phe Ser Pro Gly Phe Asn Leu
    210                 215                 220

Ser Gly Leu Phe Glu Glu Gly Glu Gly Ser Arg Phe Val Ser Gly
225                 230                 235                 240

Ala Pro Val Ser Thr Ile Ile Ser Lys Leu Glu Glu Ile Ala Lys Val
                245                 250                 255

Val Ser Phe Thr Val Arg Lys Lys Asp Cys Arg Val Ser Leu Glu Gly
                260                 265                 270

Ser Arg Glu Gly Ala Lys Gly Pro Leu Ser Ile Ala Ala Glu Ile Phe
            275                 280                 285

Glu Leu Thr Pro Ser Leu Val Val Val Glu Val Lys Lys Lys Gly Gly
            290                 295                 300

Glu Arg Gly Glu Tyr Glu Asp Phe Leu
305                 310

<210> SEQ ID NO 23
<211> LENGTH: 1838
<212> TYPE: DNA
<213> ORGANISM: Triticum aestivum

<400> SEQUENCE: 23
aaagccaaag ccaagccaac ctgttcccgt tccgttcctc ccaccccgc tcaacccgcc      60 tccctcccg cgcctccgcc cgtcccatg gcggccaccc cgccgtcgtc gcgggacccg      120
tcgccgcagc cccgccggcc ggccgccgcc gcgggccggc ccgccgccag cggcaccggc      180
accataggca acggcaagcg cggcgggctc ctgctcggcc gctacgagct gggccgcgtc      240
ctcggccacg gcaccttcgc caaggtctac acgcccgcc acgccgacac gggcgagacg      300
gtcgccatca aggtgctcga caaggagaag gcgctgcggg cgggcctcgt cccgcacatc      360
aagcgcgaga tcaccatcct ccgccgcgtc cgccacccca acatcgtgcg cctcttcgag      420
gtcatggcca ccaagtccaa gatctacttc gtcatggagt tcgtccgcgg cggcgagctc      480
ttcgcgcgcg tcgccaaggg ccgcctcaag gaggacaccg cgcgccgcta cttccagcag      540
ctcatctccg ccgtcggctt ctgccacgcg cgcggcgtct ccaccgcga cctcaagccc      600 gagaacctcc tcgtcgacga gcgcggggac ctcaaggtct ccgacttcgg cctctccgcc      660
gtcgccgacc agttccaccc cgacggcctc ctccacacct tctgcggcac ccctcctac      720 gtcgcgccgg agatgctcgc gcgccgcgga tacgacggcg ccaaggctga catatggtcc      780
tgcggcgtca tcctcttcgt cctcatggcc ggctacctcc ctttccatga ccagaacctc      840
atggccatgt accgcaagat ttacagaggg gagttccggt gtccgagatg gttctccaga      900
gatctcacca gcctattgaa tcggcttctt gacaccaacc cggagacaag gatcaccatg      960
gcggaagtca tgcagagcag gtggtttcag aaggggattt cggcccgtca ggttctatgt     1020
tgaagacgat cagctgcaca gcttagggga cagtgagagt gaggagctgg ggctggtcga     1080
acctacggag cctcctcttc ctcctccact ttccgccgcc gctgccgcca ccaccgcagc     1140
aagaggatga tgactcaggg tgggagtcgg attcctctgt cgcatcctgc cctgccacgc     1200
tgtcgtgcga ggagcggcaa cggcctgccg ggcgtctcac acggccagca agcctcaacg     1260
ctttcgatat catatccttc tccaagggat ttgatctatc agggctgttc gaggagcgag     1320
ggagcgaagt gagattcatc tcggcacaac ccatggaaac cattgttaca aaattggagg     1380
agattgccaa gatgaagagc ttctccattc gccgcaagga ctggcgcgta agcatagaag     1440
```

```
gcaccaggga aggggagaag gggccattga cgattggggc tgagatattt gagcttacac   1500
caagcctctt ggtgttggag gtgaagaaga aggcagggga taaggcagag tatgatgact   1560
tctgcaacaa agagttgaaa cctgggatgg agcctctcgt gcaccaccaa tctggttcgg   1620
ctcgaaatgt accttctgat actgagtagt tctaaaggta gctctcttgc ttgaaaggaa   1680
tataaggaaa ttttggattg aaaggatgcg tcttttatat gtttattaag catgggacct   1740
gagcagaaaa acgctattca tattccttag tcccttttgt gttagtatta ttcatttttg   1800
caatccagaa tttttcatgc ttaaaaaaaa aaaaaaaa                           1838
```

<210> SEQ ID NO 24
<211> LENGTH: 519
<212> TYPE: PRT
<213> ORGANISM: Triticum aestivum
<220> FEATURE:
<221> NAME/KEY: misc_feature
<222> LOCATION: (302)..(302)
<223> OTHER INFORMATION: Xaa can be any naturally occurring amino acid
<220> FEATURE:
<221> NAME/KEY: misc_feature
<222> LOCATION: (341)..(341)
<223> OTHER INFORMATION: Xaa can be any naturally occurring amino acid

<400> SEQUENCE: 24

```
Met Ala Ala Thr Pro Pro Ser Ser Arg Asp Pro Ser Pro Gln Pro Arg
1               5                   10                  15

Arg Pro Ala Ala Ala Gly Arg Pro Ala Ala Ser Gly Thr Gly Thr
            20                  25                  30

Ile Gly Asn Gly Lys Arg Gly Gly Leu Leu Leu Gly Arg Tyr Glu Leu
        35                  40                  45

Gly Arg Val Leu Gly His Gly Thr Phe Ala Lys Val Tyr His Ala Arg
    50                  55                  60

His Ala Asp Thr Gly Glu Thr Val Ala Ile Lys Val Leu Asp Lys Glu
65                  70                  75                  80

Lys Ala Leu Arg Ala Gly Leu Val Pro His Ile Lys Arg Glu Ile Thr
                85                  90                  95

Ile Leu Arg Arg Val Arg His Pro Asn Ile Val Arg Leu Phe Glu Val
            100                 105                 110

Met Ala Thr Lys Ser Lys Ile Tyr Phe Val Met Glu Phe Val Arg Gly
        115                 120                 125

Gly Glu Leu Phe Ala Arg Val Ala Lys Gly Arg Leu Lys Glu Asp Thr
    130                 135                 140

Ala Arg Arg Tyr Phe Gln Gln Leu Ile Ser Ala Val Gly Phe Cys His
145                 150                 155                 160

Ala Arg Gly Val Phe His Arg Asp Leu Lys Pro Glu Asn Leu Leu Val
                165                 170                 175

Asp Glu Arg Gly Asp Leu Lys Val Ser Asp Phe Gly Leu Ser Ala Val
            180                 185                 190

Ala Asp Gln Phe His Pro Asp Gly Leu Leu His Thr Phe Cys Gly Thr
        195                 200                 205

Pro Ser Tyr Val Ala Pro Glu Met Leu Ala Arg Arg Gly Tyr Asp Gly
    210                 215                 220

Ala Lys Ala Asp Ile Trp Ser Cys Gly Val Ile Leu Phe Val Leu Met
225                 230                 235                 240

Ala Gly Tyr Leu Pro Phe His Asp Gln Asn Leu Met Ala Met Tyr Arg
                245                 250                 255

Lys Ile Tyr Arg Gly Glu Phe Arg Cys Pro Arg Trp Phe Ser Arg Asp
```

```
                    260                 265                 270
Leu Thr Ser Leu Leu Asn Arg Leu Leu Asp Thr Asn Pro Glu Thr Arg
            275                 280                 285
Ile Thr Met Ala Glu Val Met Gln Ser Arg Trp Phe Gln Xaa Gly Phe
        290                 295                 300
Arg Pro Val Arg Phe Tyr Val Glu Asp Asp Gln Leu His Ser Leu Gly
305                 310                 315                 320
Asp Ser Glu Ser Glu Leu Gly Leu Val Glu Pro Thr Glu Pro Pro
                325                 330                 335
Leu Pro Pro Pro Xaa Pro Pro Leu Pro Pro Pro Gln Gln Glu
            340                 345                 350
Asp Asp Asp Ser Gly Trp Glu Ser Asp Ser Ser Val Ala Ser Cys Pro
            355                 360                 365
Ala Thr Leu Ser Cys Glu Glu Arg Gln Arg Pro Ala Gly Arg Leu Thr
        370                 375                 380
Arg Pro Ala Ser Leu Asn Ala Phe Asp Ile Ile Ser Phe Ser Lys Gly
385                 390                 395                 400
Phe Asp Leu Ser Gly Leu Phe Glu Glu Arg Gly Ser Glu Val Arg Phe
                405                 410                 415
Ile Ser Ala Gln Pro Met Glu Thr Ile Val Thr Lys Leu Glu Glu Ile
            420                 425                 430
Ala Lys Met Lys Ser Phe Ser Ile Arg Arg Lys Asp Trp Arg Val Ser
        435                 440                 445
Ile Glu Gly Thr Arg Glu Gly Glu Lys Gly Pro Leu Thr Ile Gly Ala
        450                 455                 460
Glu Ile Phe Glu Leu Thr Pro Ser Leu Leu Val Leu Glu Val Lys Lys
465                 470                 475                 480
Lys Ala Gly Asp Lys Ala Glu Tyr Asp Asp Phe Cys Asn Lys Glu Leu
                485                 490                 495
Lys Pro Gly Met Glu Pro Leu Val His His Gln Ser Gly Ser Ala Arg
            500                 505                 510
Asn Val Pro Ser Asp Thr Glu
        515

<210> SEQ ID NO 25
<211> LENGTH: 2110
<212> TYPE: DNA
<213> ORGANISM: Triticum aestivum

<400> SEQUENCE: 25
gaaatagttt tcgcagagcc gttaagctca cctccttcga ggccggctgc tccacctcca    60
cctccaccta atcccattc gcctcgcctc ccgcccacc gccaccaccc gtcgatggcg     120
gccatcaagc cgccgccgcc tgaccggccg ccgcaggccg cgcggctgcc gtcccttcc    180
tcttcctcct cggcggtggc ggcggccaag cgaggcgcca caggctcccg cgggctgctc    240
atggggcgct acgagctggg ccgcgtcctg gcaaaggca ccttcgccaa ggtgtaccac     300
gcgcggcacg tgcagaccgg cgagagcgtg ccatcaagg tgctcgaccg ggagaaggcc     360
gtgcggagcg gcctcgtctc gcacatcaag gcgagatcg ccgtgctccg ccgcgtgcgc    420
cacccccaaca tcgtgcacct cttcgaggtc atggccacca agaccaagat ctacttcgtc    480
atggagctcg tccgcggcgg cgagctcttc tcccgcgtct ccaagggccg cctcaaggag    540
gacattgcgc ccgctactt ccagcacctc atctccgccg tcggcttctg ccacacccgc    600
ggggtcttcc accgggacct caagccggag aacctcctcg tcgacgaggc gggcaacctc    660
```

```
aaggtgtccg acttcggcct ctccgccgtc gccgagccgt tccagccaga gggtctcctc    720
cacaccttct gcggcacgcc ggcctacgtc gcgcccgaag tcctcgcccg ccgtggatac    780
gaaggcgcca aggccgacat atggtcctgc ggtgtcatcc tctttgttct catggccgga    840
tacctccctt ccatgaccca gaacctcatg gccatgtacc gtaaggttta caagggagag    900
ttccgatgtc caaggtggtt ctccaaggac cttactagct tgatcatgcg ttttcttgac    960
acaaacccaa gcaccaggat caccttgccg gaggtcatgg agagccggtg gttcaagaaa   1020
ggtttccggc cagtcaagtt ctatattgaa gatgaccagc tgtacaacgt cattgatgcc   1080
gagaatgata tgctcgactt gggtctccct gaccctcttc ctcaaccatt gcttcctcca   1140
ccttcatctc catctccgca agaagttgat ggagatgact cagggtcaga atccgacgca   1200
tcagtcgtgt cctgccctgc cacatcgtca tttgaagagc gccacaggct ccgcgggcca   1260
ctcccacgcc ccgcaagcct taacgcgttt gatatcatat cattctcaag gggattcaac   1320
ttgtcgggc tgtttgagga aaaagggac gaggtgagat tcatctcgag tgaacctatg   1380
tcggcatta taacgaaatt agaggagatc gcaaatgtga agagcttcgc ggtgcggaag   1440
aaggattggc gggtgagcct agagggcaca agggaagggg ttaaggggcc actaacaatc   1500
tgcgcggaga tatttgaact cacaccctcc cttgtagtag tggaggtaaa aaagaaggcg   1560
ggggataagg aagagtatga tgatttctgc aacaaggaat tgaagccagg aatgcagcat   1620
cttgtgcacc agatggcccc agttccaatt acacctacca tttctgagta ggccgaaagg   1680
ccttcaaggt aacaggcgcc accgccccta gagctaacgg ggatagggg agcgactctc   1740
caagctagaa agaaactgga gtcgggtgca actgacagga gcaagagttc ttgtagtctc   1800
gggcactgac gatgatgagc gcggttactt ggttaactct ggagagcata cgtaatgtta   1860
tccgagacgg gagctagatt gtggctgtat atggtgtcac cctagctgct gtttaaatgt   1920
ttgtactttt ctctacttaa tttgctgatg atgattgtgt atgtactccc gctgttggtt   1980
tatcagcaga accgaataat tttgggcaat cgttaattca aggaccaaac tgattgagga   2040
ataaattggg tgcaacatgc attgcatgca ccctttggcc accaggcaca tgcagacgtg   2100
cttggattcc                                                         2110
```

<210> SEQ ID NO 26
<211> LENGTH: 518
<212> TYPE: PRT
<213> ORGANISM: Triticum aestivum

<400> SEQUENCE: 26

Met Ala Ala Ile Lys Pro Pro Pro Asp Arg Pro Pro Gln Ala Ala
1               5                   10                  15

Arg Leu Pro Ser Pro Ser Ser Ser Ser Ala Val Ala Ala Ala Lys
                20                  25                  30

Arg Gly Ala Thr Gly Ser Arg Gly Leu Leu Met Gly Arg Tyr Glu Leu
            35                  40                  45

Gly Arg Val Leu Gly Lys Gly Thr Phe Ala Lys Val Tyr His Ala Arg
        50                  55                  60

His Val Gln Thr Gly Glu Ser Val Ala Ile Lys Val Leu Asp Arg Glu
65                  70                  75                  80

Lys Ala Val Arg Ser Gly Leu Val Ser His Ile Lys Arg Glu Ile Ala
                85                  90                  95

Val Leu Arg Arg Val Arg His Pro Asn Ile Val His Leu Phe Glu Val
            100                 105                 110

```
Met Ala Thr Lys Thr Lys Ile Tyr Phe Val Met Glu Leu Val Arg Gly
        115                 120                 125
Gly Glu Leu Phe Ser Arg Val Ser Lys Gly Arg Leu Lys Glu Asp Ile
        130                 135                 140
Ala Arg Arg Tyr Phe Gln His Leu Ile Ser Ala Val Gly Phe Cys His
145                 150                 155                 160
Thr Arg Gly Val Phe His Arg Asp Leu Lys Pro Glu Asn Leu Leu Val
                    165                 170                 175
Asp Glu Ala Gly Asn Leu Lys Val Ser Asp Phe Gly Leu Ser Ala Val
                180                 185                 190
Ala Glu Pro Phe Gln Pro Glu Gly Leu Leu His Thr Phe Cys Gly Thr
        195                 200                 205
Pro Ala Tyr Val Ala Pro Glu Val Leu Ala Arg Arg Gly Tyr Glu Gly
        210                 215                 220
Ala Lys Ala Asp Ile Trp Ser Cys Gly Val Ile Leu Phe Val Leu Met
225                 230                 235                 240
Ala Gly Tyr Leu Pro Phe His Asp Gln Asn Leu Met Ala Met Tyr Arg
                245                 250                 255
Lys Val Tyr Lys Gly Glu Phe Arg Cys Pro Arg Trp Phe Ser Lys Asp
                260                 265                 270
Leu Thr Ser Leu Ile Met Arg Phe Leu Asp Thr Asn Pro Ser Thr Arg
        275                 280                 285
Ile Thr Leu Pro Glu Val Met Glu Ser Arg Trp Phe Lys Lys Gly Phe
        290                 295                 300
Arg Pro Val Lys Phe Tyr Ile Glu Asp Asp Gln Leu Tyr Asn Val Ile
305                 310                 315                 320
Asp Ala Glu Asn Asp Met Leu Asp Leu Gly Leu Pro Asp Pro Leu Pro
                325                 330                 335
Gln Pro Leu Leu Pro Pro Ser Ser Pro Ser Pro Gln Glu Val Asp
                340                 345                 350
Gly Asp Asp Ser Gly Ser Glu Ser Asp Ala Ser Val Val Ser Cys Pro
                355                 360                 365
Ala Thr Ser Ser Phe Glu Glu Arg His Arg Leu Arg Gly Pro Leu Pro
        370                 375                 380
Arg Pro Ala Ser Leu Asn Ala Phe Asp Ile Ile Ser Phe Ser Arg Gly
385                 390                 395                 400
Phe Asn Leu Ser Gly Leu Phe Glu Glu Lys Gly Asp Glu Val Arg Phe
                405                 410                 415
Ile Ser Ser Glu Pro Met Ser Gly Ile Ile Thr Lys Leu Glu Glu Ile
                420                 425                 430
Ala Asn Val Lys Ser Phe Ala Val Arg Lys Lys Asp Trp Arg Val Ser
        435                 440                 445
Leu Glu Gly Thr Arg Glu Gly Val Lys Gly Pro Leu Thr Ile Cys Ala
        450                 455                 460
Glu Ile Phe Glu Leu Thr Pro Ser Leu Val Val Val Glu Val Lys Lys
465                 470                 475                 480
Lys Ala Gly Asp Lys Glu Glu Tyr Asp Asp Phe Cys Asn Lys Glu Leu
                485                 490                 495
Lys Pro Gly Met Gln His Leu Val His Gln Met Ala Pro Val Pro Ile
                500                 505                 510
Thr Pro Thr Ile Ser Glu
        515
```

<210> SEQ ID NO 27
<211> LENGTH: 527
<212> TYPE: PRT
<213> ORGANISM: Triticum aestivum

<400> SEQUENCE: 27

Met Ser Ala Ile Lys Pro Pro Pro Asp Arg Pro Gln Ala Ala
1               5                   10                  15

Arg Leu Pro Ser Pro Ser Ser Ser Ala Ala Ala Ala Lys
            20              25              30

Gln Gly Gly Thr Gly Ser Arg Gly Leu Leu Met Gly Arg Tyr Glu Leu
        35                  40                  45

Gly Arg Val Leu Gly Lys Gly Thr Phe Ala Lys Val Tyr His Ala Arg
50                  55                  60

His Val Gln Thr Gly Glu Ser Val Ala Ile Lys Val Leu Asp Arg Glu
65                  70                  75                  80

Lys Ala Val Arg Ser Gly Leu Val Ser His Ile Lys Arg Glu Ile Ala
                85                  90                  95

Val Leu Arg Arg Val Arg His Pro Asn Ile Val His Leu Phe Glu Val
            100                 105                 110

Met Ala Thr Lys Thr Lys Ile Tyr Phe Val Met Glu Leu Val Val Ala
        115                 120                 125

Ala Leu Leu Arg Phe Ser Lys Gly Arg Leu Lys Glu Asp Ile Ala Arg
    130                 135                 140

Arg Tyr Phe Gln His Leu Ile Ser Ala Val Gly Phe Cys His Thr Arg
145                 150                 155                 160

Gly Val Phe His Arg Asp Leu Lys Pro Glu Asn Leu Leu Val Asp Glu
                165                 170                 175

Ala Gly Asn Leu Lys Val Ser Asp Phe Gly Leu Ser Ala Val Ala Glu
            180                 185                 190

Pro Phe Gln Pro Glu Gly Leu Leu His Thr Phe Cys Gly Thr Arg Ala
        195                 200                 205

Tyr Val Ala Pro Glu Val Leu Ala Arg Arg Gly Tyr Glu Gly Ala Lys
    210                 215                 220

Ala Asp Ile Trp Ser Cys Gly Val Ile Leu Phe Val Leu Met Ala Gly
225                 230                 235                 240

Tyr Leu Pro Phe His Asp Gln Asn Leu Met Ala Met Tyr Arg Lys Phe
                245                 250                 255

Thr Arg Glu Ser Ser Met Ser Arg Trp Phe Ser Lys Asp Leu Thr Ser
            260                 265                 270

Leu Ile Met Arg Phe Leu Asp Thr Asn Pro Ser Thr Arg Ile Thr Leu
        275                 280                 285

Pro Glu Ser Trp Arg Ala Gly Gly Ser Arg Lys Val Ser Gly Gln Ser
    290                 295                 300

Ser Ser Ile Leu Lys Thr Asn Gln Leu Tyr Asn Val Ile Asp Ala Glu
305                 310                 315                 320

Asn Asp Met Leu Asp Leu Gly Leu Pro Asp Pro Leu Pro Gln Pro Leu
                325                 330                 335

Pro Pro Pro Pro Pro Ser Pro Ser Pro Gln Gln Val Asp Gly Asp Asp
            340                 345                 350

Ser Gly Ser Glu Ser Asp Ala Ser Val Val Ser Cys Pro Ala Thr Ser
        355                 360                 365

Ser Phe Glu Glu Arg His Arg Leu Arg Gly Pro Leu Pro Arg Pro Ala
    370                 375                 380

Ser Leu Asn Ala Phe Asp Ile Ile Ser Phe Ser Arg Gly Phe Asn Leu
385                 390                 395                 400

Ser Gly Leu Phe Glu Glu Lys Gly Asp Glu Val Arg Phe Ile Ser Gly
            405                 410                 415

Glu Pro Met Pro Asp Ile Ile Thr Lys Leu Glu Ile Ala Asn Val
            420                 425                 430

Lys Ser Phe Ala Cys Glu Glu Gly Leu Ala Gly Asp Leu Glu Gly Thr
        435                 440                 445

Arg Glu Gly Val Lys Gly Pro Leu Thr Ile Cys Ala Glu Ile Phe Glu
    450                 455                 460

Leu Thr Pro Ser Leu Val Val Glu Val Lys Lys Ala Gly Asp
465                 470                 475                 480

Lys Glu Glu Tyr Asp Asp Phe Cys Asn Lys Leu Lys Pro Gly Met
            485                 490                 495

Gln His Leu Val His Gln Met Val Pro Val Pro Asn Thr Pro Thr Ile
        500                 505                 510

Ser Glu Leu Ala Glu Thr Val Gln Gly Asn Arg Arg His Arg Pro
    515                 520                 525

<210> SEQ ID NO 28
<211> LENGTH: 877
<212> TYPE: DNA
<213> ORGANISM: Hordeum vulgare

<400> SEQUENCE: 28
cccgggctgc aggaattcgg cacgaggtgc tcgacttggg tctctctgat cctcttcctc      60
aaccattgcc acctccacct ccacctccgc aagaagttga tggaaatgac tcagggtcag     120
aatcggactc atcagtcatg tcctgccctg ccacatcgtc atttgaagag cgccagaggc     180
tccgcgggcc actcccacgc cccgcaagtc ttaatgcatt cgatatcata tcattctcaa     240
ggggattcaa cttgtcgggg ctgtttgagg aaaaagggga cgaggtgaga ttcatctcga     300
gtgaacctat gtcggacatt ataacgaaat tggaggagat cgcaaatgtg aagagctttg     360
cggtgcggaa gaaggattgg cgggtgagcc tagagggtac aagggaagga gttaaggggc     420
cactaacaat cggcgcagag atatttgaac tcacaccctc ccttgtagta gtggaggtaa     480
aaaagaaggc gggggataag gaagagtatg atgatttctg caacaaggaa ttgaagccag     540
gaatggagca tcttgtgcac cagatggtcc cagttccaaa tacacctacc atttctgagt     600
aggccaaagg ccttgaaggt tactggcgcc actgccccta gagctaacgg ggataggagg     660
agcgactctc tccaagctag aaacaggccg agtcgtgtg gaactgacag gaggagcatc     720
tcttgtagtg tgggacggga gccccctgac cagctcgggc agggcactga tgatgagcgc     780
ggtttactct tacgagctcg cttctctgga gagcataaca caatgttgtc cgagacggag     840
ctagattgtg gctgtagtac tgtatatggc gtcgccc                              877

<210> SEQ ID NO 29
<211> LENGTH: 199
<212> TYPE: PRT
<213> ORGANISM: Hordeum vulgare

<400> SEQUENCE: 29

Arg Ala Ala Gly Ile Arg His Glu Val Leu Asp Leu Gly Leu Ser Asp
1               5                   10                  15

Pro Leu Pro Gln Pro Leu Pro Pro Pro Pro Pro Pro Gln Glu Val
            20                  25                  30

Asp Gly Asn Asp Ser Gly Ser Glu Ser Asp Ser Val Met Ser Cys
        35                  40                  45

Pro Ala Thr Ser Ser Phe Glu Glu Arg Gln Arg Leu Arg Gly Pro Leu
 50                  55                  60

Pro Arg Pro Ala Ser Leu Asn Ala Phe Asp Ile Ile Ser Phe Ser Arg
65                  70                  75                  80

Gly Phe Asn Leu Ser Gly Leu Phe Glu Glu Lys Gly Asp Glu Val Arg
                85                  90                  95

Phe Ile Ser Ser Glu Pro Met Ser Asp Ile Ile Thr Lys Leu Glu Glu
                100                 105                 110

Ile Ala Asn Val Lys Ser Phe Ala Val Arg Lys Lys Asp Trp Arg Val
            115                 120                 125

Ser Leu Glu Gly Thr Arg Glu Gly Val Lys Gly Pro Leu Thr Ile Gly
        130                 135                 140

Ala Glu Ile Phe Glu Leu Thr Pro Ser Leu Val Val Glu Val Lys
145                 150                 155                 160

Lys Lys Ala Gly Asp Lys Glu Glu Tyr Asp Asp Phe Cys Asn Lys Glu
                165                 170                 175

Leu Lys Pro Gly Met Glu His Leu Val His Gln Met Val Pro Val Pro
                180                 185                 190

Asn Thr Pro Thr Ile Ser Glu
        195

<210> SEQ ID NO 30
<211> LENGTH: 750
<212> TYPE: DNA
<213> ORGANISM: Allium porrum

<400> SEQUENCE: 30
gcctgtgaaa tattacattg agaacgatag atttcataag tggtgtagct tagatgaaga      60
gaatgctaat gacgaggagg aggtagaatc tggagatgaa tcgggactct tcagtttgct     120
tcctgcccct gccgcgcttg acgagggaaa agaaagaaaa aggacagggg aaactccaat     180
aggcctttga gtttgaatgc atttgacata atttcctttt caagaggatt tgatctttcg     240
ggtttgtttg atgaaacagg agatgaaact agatttgtgt cgggtgaatc gataccgaac     300
atcatatcga aactagagga gattgcaaag gttgggagtt ttacctttag aagaaggat      360 tgtagggtta gtttagaagg gacgcgggaa ggagtgaagg gcccgcttac aattggtgct     420
gagatatttg agctgacgcc ttgtttggtt gttgttgagc ttaagaagaa agcaggagac     480
aaagcagagt atgaggagtt tgtaacaag gagctgaaac ctgggttgct acatcttatg     540
tttcctgatg gcggtgttcc ttccaacaca acttctgata cagagtaggc agtgcaggga     600
attctagttt ctaggtgtt ggcctcctgg gccccccggg accttctgat tctcaattgt     660
tatctgtatt atatagcagt gttttatgat tcattttgtg ttagatttgt agtaagaaat     720
ttatgttaac ttagatgaaa atcaagtttc                                      750

<210> SEQ ID NO 31
<211> LENGTH: 148
<212> TYPE: PRT
<213> ORGANISM: Allium porrum

<400> SEQUENCE: 31

Arg Gly Lys Arg Lys Lys Asp Arg Gly Asn Ser Asn Arg Pro Leu
1               5                   10                  15

```
Ser Leu Asn Ala Phe Asp Ile Ile Ser Phe Ser Arg Gly Phe Asp Leu
         20                  25                  30

Ser Gly Leu Phe Asp Glu Thr Gly Asp Glu Thr Arg Phe Val Ser Gly
     35                  40                  45

Glu Ser Ile Pro Asn Ile Ile Ser Lys Leu Glu Ile Ala Lys Val
 50                  55                  60

Gly Ser Phe Thr Phe Arg Lys Lys Asp Cys Arg Val Ser Leu Glu Gly
 65                  70                  75                  80

Thr Arg Glu Gly Val Lys Gly Pro Leu Thr Ile Gly Ala Glu Ile Phe
                 85                  90                  95

Glu Leu Thr Pro Cys Leu Val Val Val Glu Leu Lys Lys Lys Ala Gly
            100                 105                 110

Asp Lys Ala Glu Tyr Glu Glu Phe Cys Asn Lys Glu Leu Lys Pro Gly
            115                 120                 125

Leu Leu His Leu Met Phe Pro Asp Gly Gly Val Pro Ser Asn Thr Thr
        130                 135                 140

Ser Asp Thr Glu
145

<210> SEQ ID NO 32
<211> LENGTH: 1235
<212> TYPE: DNA
<213> ORGANISM: Allium porrum

<400> SEQUENCE: 32
aattcggcac gagagacggt ccgattccaa ttccgttctg ctgatccggc acgaggctgg     60
gcaagctcct cggccatggc aacttcgcca aggtctacct cgcgcgcaac ctcgcctcca    120
acgaggaagt cgctatcaag gtcttcgata aggagaaaat cctcaaatcc ggcctcgtca    180
accacaccaa acgcgagatc tcaatcctcc gccgtcttcg tcatcccaat gtcgtcgagc    240
tcttcgaggt catggccacc aaatcaaaga tctatttcgt aatagagtac gtccgaggtg    300
gtgaattgtt cggcaaggta gccaagggc gtctcaacga aacacggca agaaagtact     360 ttcagcaatt gatttccgcc gttgatttct gccacgccag aggcgtgtac caccgagatc    420
tgaagccgga gaatttgttg ttagacgata atggcgattt gaaggtgtcg gatttcgggt    480
tgagcgctgt atcggaccag atgaggcagg atggtttgtt tcacacgttt tgtggtactc    540
cagcctacgt tgctccagag gttctcggaa ggaaagggta tgatgggct aaatttgaca     600 tttggtcatg tggtgttatt tgttttttgt tgatggcagg gtacttgccc tttcatgatc    660
aaaacgtgat ggctatgtat aagaagattt ataaggga gtttaggtgt ccgagatggt     720
tttcaaagga tttgacaagg ttgctgatga ggcttcttga tacaaatccc aaaacccgga    780
ttactattcc ggggggatg gagaacagat ggttcaagaa tggattcgag cctgtgaaat     840
attacattga gaatgataga tttcataagt ggtgtagctt agatgaagag aacgctaatg    900
acgaggagga ggtagaatct gctcgtgccg cggtctcttc agttgcttcc tgccctgccg    960
cgcttgatga gggaaagaag aaaaggacag ggaaactcca taggccttta aggttgaatg   1020
catttgacat aatttccttt tcaagaggat ttgatctttc gggtttgttt gatgaaacag   1080
gagacgaaac tagatttgtg tcgggtgaat caatacccaa catcatattt cctcttccaa   1140
aaccgtttta agcaatccgg agtttgtata ccttcccttc caaagccctt gtctctaaat   1200
cgccatcgct gcaccaatag ccgccactga ccacc                              1235

<210> SEQ ID NO 33
```

<211> LENGTH: 368
<212> TYPE: PRT
<213> ORGANISM: Allium porrum

<400> SEQUENCE: 33

```
Ser Gly Thr Arg Leu Gly Lys Leu Leu Gly His Gly Asn Phe Ala Lys
1               5                   10                  15

Val Tyr Leu Ala Arg Asn Leu Ala Ser Asn Glu Glu Val Ala Ile Lys
            20                  25                  30

Val Phe Asp Lys Glu Lys Ile Leu Lys Ser Gly Leu Val Asn His Thr
        35                  40                  45

Lys Arg Glu Ile Ser Ile Leu Arg Arg Leu Arg His Pro Asn Val Val
    50                  55                  60

Glu Leu Phe Glu Val Met Ala Thr Lys Ser Lys Ile Tyr Phe Val Ile
65                  70                  75                  80

Glu Tyr Val Arg Gly Gly Glu Leu Phe Gly Lys Val Ala Lys Gly Arg
                85                  90                  95

Leu Asn Glu Asn Thr Ala Arg Lys Tyr Phe Gln Gln Leu Ile Ser Ala
            100                 105                 110

Val Asp Phe Cys His Ala Arg Gly Val Tyr His Arg Asp Leu Lys Pro
        115                 120                 125

Glu Asn Leu Leu Leu Asp Asp Asn Gly Asp Leu Lys Val Ser Asp Phe
    130                 135                 140

Gly Leu Ser Ala Val Ser Asp Gln Met Arg Gln Asp Gly Leu Phe His
145                 150                 155                 160

Thr Phe Cys Gly Thr Pro Ala Tyr Val Ala Pro Glu Val Leu Gly Arg
                165                 170                 175

Lys Gly Tyr Asp Gly Ala Lys Phe Asp Ile Trp Ser Cys Gly Val Ile
            180                 185                 190

Leu Phe Leu Leu Met Ala Gly Tyr Leu Pro Phe His Asp Gln Asn Val
        195                 200                 205

Met Ala Met Tyr Lys Lys Ile Tyr Lys Gly Glu Phe Arg Cys Pro Arg
    210                 215                 220

Trp Phe Ser Lys Asp Leu Thr Arg Leu Leu Met Arg Leu Leu Asp Thr
225                 230                 235                 240

Asn Pro Lys Thr Arg Ile Thr Ile Pro Gly Gly Met Glu Asn Arg Trp
                245                 250                 255

Phe Lys Asn Gly Phe Glu Pro Val Lys Tyr Tyr Ile Glu Asn Asp Arg
            260                 265                 270

Phe His Lys Trp Cys Ser Leu Asp Glu Glu Asn Ala Asn Asp Glu Glu
        275                 280                 285

Glu Val Glu Ser Ala Arg Ala Val Ser Ser Val Ala Ser Cys Pro
    290                 295                 300

Ala Ala Leu Asp Glu Gly Lys Lys Lys Arg Thr Gly Lys Leu His Arg
305                 310                 315                 320

Pro Leu Arg Leu Asn Ala Phe Asp Ile Ile Ser Phe Ser Arg Gly Phe
                325                 330                 335

Asp Leu Ser Gly Leu Phe Asp Glu Thr Gly Asp Glu Thr Arg Phe Val
            340                 345                 350

Ser Gly Glu Ser Ile Pro Asn Ile Ile Phe Pro Leu Pro Lys Pro Phe
        355                 360                 365
```

<210> SEQ ID NO 34
<211> LENGTH: 1427
<212> TYPE: DNA

-continued

```
<213> ORGANISM: Brassica napus

<400> SEQUENCE: 34
gtcgacccac gcgtccggtc cgcggcggcg agctcttcaa caaagtcgcc aaagggcgcc      60
tcaaggagga tgtcgcccgc aagtacttcc agcagctgat ctccgccgtc acgttctgcc     120
acgcccgcgg cgtctaccac cgcgacatca agccggagaa tctcctcctc gacgagaacg     180
ggaacctcaa agtctccgac tttgggctca gcgctgtctc cgatcagatt cgccaggacg     240
ggcttttcca cacgttctgt gggaccctg cttacgtggc gccagaggtt ttggctagga      300
aggggtacga cgcgggtaaa gttgatatct ggtcttgtgg tgttgtgttg tttgttttga     360
tggctggtta cctcccttt cacgaccgta acgttatggc tatgtacaag aagatttaca     420
aaggagagtt taggtgtccg agttggttct ctcccgagct cacgaggttg tgttctcgcc     480
tcctcgagac gaatccggag aaacggttta cgttccctca gattatggag aactcttggt     540
tcaagaaagg gtttaagcat gttaagttct acgtggaaga tgataagctt tgtaacgttg     600
ttgatgatga cgatgagttg gagactggtt ccgttgagtc tgatcggtct tctaccgttt     660
ctgaatcgga cgttgagttt ttcaagcccg cgaggagagt tggggggttg cctaggcctg     720
cgagtttgaa tgcttttgat atatatcgtt ctcgcaaggg tttgatttgt ctggtctgtt     780
tgatgatgat ggggaagggt ctaggtttgt ctcgggagct ccggtttcga agattatatc     840
gaagctggaa gagattgcta agttgtgag ctttaccgtg aggaagaagg attgtagagt      900
gagtcttgaa gggtcgagac aaggagtgaa aggtcctttg actattgctg cggagatatt     960
cgagctgacg ccgtctttgg ttgttgtgga agttaagaag aaaggagggg atagaactga    1020
gtatgaagag ttttgtaaca aggagttgaa accgaagttg cagaccttga cggctgatga    1080
agtagatgat cctgtggcgg tgtcagcggt ggttgatgaa accgcgtctg gagtggcgaa    1140
ttctccgccg gtttgtttct tgccttctga cactgagtag aagatgagat catgaggggt    1200
tttgttaacc gaactgatga aactgcttag ggttggtgaa atgtagaacc gaagtatgta    1260
acatgttatg ttttacagtt ggagagatcg ttagagacgg actttgaatt atgttttac     1320 taaccttta gcagttttt tgtgttcttg tgtgtgtgtg gaagagtttg taaacagttt     1380
cgtatcagat cttttaatat gtaaaaaaaa aaaaaagggg cggccgc                  1427
```

```
<210> SEQ ID NO 35
<211> LENGTH: 392
<212> TYPE: PRT
<213> ORGANISM: Brassica napus
<220> FEATURE:
<221> NAME/KEY: misc_feature
<222> LOCATION: (248)..(248)
<223> OTHER INFORMATION: Xaa can be any naturally occurring amino acid

<400> SEQUENCE: 35

Arg Pro Thr Arg Pro Val Arg Gly Gly Glu Leu Phe Asn Lys Val Ala
1               5                  10                  15

Lys Gly Arg Leu Lys Glu Asp Val Ala Arg Lys Tyr Phe Gln Gln Leu
            20                  25                  30

Ile Ser Ala Val Thr Phe Cys His Ala Arg Gly Val Tyr His Arg Asp
        35                  40                  45

Ile Lys Pro Glu Asn Leu Leu Leu Asp Glu Asn Gly Asn Leu Lys Val
    50                  55                  60

Ser Asp Phe Gly Leu Ser Ala Val Ser Asp Gln Ile Arg Gln Asp Gly
65                  70                  75                  80
```

-continued

```
Leu Phe His Thr Phe Cys Gly Thr Pro Ala Tyr Val Ala Pro Glu Val
             85                  90                  95
Leu Ala Arg Lys Gly Tyr Asp Ala Gly Lys Val Asp Ile Trp Ser Cys
            100                 105                 110
Gly Val Val Leu Phe Val Leu Met Ala Gly Tyr Leu Pro Phe His Asp
        115                 120                 125
Arg Asn Val Met Ala Met Tyr Lys Lys Ile Tyr Lys Gly Glu Phe Arg
    130                 135                 140
Cys Pro Ser Trp Phe Ser Pro Glu Leu Thr Arg Leu Cys Ser Arg Leu
145                 150                 155                 160
Leu Glu Thr Asn Pro Glu Lys Arg Phe Thr Phe Pro Gln Ile Met Glu
                165                 170                 175
Asn Ser Trp Phe Lys Lys Gly Phe Lys His Val Lys Phe Tyr Val Glu
            180                 185                 190
Asp Asp Lys Leu Cys Asn Val Val Asp Asp Asp Glu Leu Glu Thr
        195                 200                 205
Gly Ser Val Glu Ser Asp Arg Ser Ser Thr Val Ser Glu Ser Asp Val
    210                 215                 220
Glu Phe Phe Lys Pro Ala Arg Arg Val Gly Gly Leu Pro Arg Pro Ala
225                 230                 235                 240
Ser Leu Asn Ala Phe Asp Ile Xaa Ser Phe Ser Gln Gly Phe Asp Leu
                245                 250                 255
Ser Gly Leu Phe Asp Asp Gly Glu Gly Ser Arg Phe Val Ser Gly
            260                 265                 270
Ala Pro Val Ser Lys Ile Ile Ser Lys Leu Glu Glu Ile Ala Lys Val
    275                 280                 285
Val Ser Phe Thr Val Arg Lys Lys Asp Cys Arg Val Ser Leu Glu Gly
290                 295                 300
Ser Arg Gln Gly Val Lys Gly Pro Leu Thr Ile Ala Ala Glu Ile Phe
305                 310                 315                 320
Glu Leu Thr Pro Ser Leu Val Val Glu Val Lys Lys Lys Gly Gly
                325                 330                 335
Asp Arg Thr Glu Tyr Glu Glu Phe Cys Asn Lys Glu Leu Lys Pro Lys
            340                 345                 350
Leu Gln Thr Leu Thr Ala Asp Glu Val Asp Asp Pro Val Ala Val Ser
        355                 360                 365
Ala Val Val Asp Glu Thr Ala Ser Gly Val Ala Asn Ser Pro Pro Val
    370                 375                 380
Cys Phe Leu Pro Ser Asp Thr Glu
385                 390

<210> SEQ ID NO 36
<211> LENGTH: 1840
<212> TYPE: DNA
<213> ORGANISM: Pisum sativum

<400> SEQUENCE: 36
gcacgaggtc catcacaaga aactagagaa acctctcatc tccatccatg gcagtagtag      60
cagctcccaa gaagaacaac tcattcaaca agaaagacaa cccaaatctt ctattgggtc     120
gtttcgaatt aggaaaactc ctcggccatg gaaccttcgc caaggtccac ctagctaaaa     180
acatcaaaac cggtgaagca gtagctataa agatcataag caaagacaaa atccttaaaa     240
gtggtttagt ttcacacatc aaacgagaaa tctccattct ccgccgtgtc cgccacccca     300
acatcgtcca gctgttcgaa gtcatggcga caaagacaaa gatctacttc gtgatggaat     360
```

```
atgtacgagg tggagagctt ttcaataaag ttgctaaagg taggttgaaa gaagaggttg      420
cgagaaaata ttttcaacag ttaatatgtg cggttgaatt ttgtcatgct agaggtgttt      480
ttcatagaga tataaagcct gagaatttgt tgcttgatga aaatggtaac cttaaagttt      540
ccgattttgg gttaagtgct gtgtcggatg agattaagca agatggggttg tttcatactt     600 tttgtggtac acctgcatat gttgctcctg aggttttgtc taggaaaggt tatgatggtg      660
gtaaggttga tatttggtct tgtggtgttg tttttgtttgt tttaatggct ggttatttac     720
cttttcatga tcctaataat gttatggtta tgtataagaa gatttataaa ggtgatttta     780
ggtgtcctag atggttttct cctgagcttg ttaaccttct tactaggctt cttgatacta     840
agcctcaaac taggatttcg attccggaga ttatggagaa tcgttggttt aagataggtt     900
ttaagcgtat taagttttat gttgaggatg atgttgtttg taatcttgat tctcttggtc     960
ttgatggtaa taatggtaat gatggtaatg atgataagaa ggtgctaaac attgatgaac    1020
accgtgatga agcgttggaa tcggtatcag aatcagaatg ggattctgag gttgtgaata    1080
gaaggaagaa tcgtcagctt ggttcattgc caaggcctgc gagtttgaat gcttttgaca    1140
ttatatcgtt ttcgcaaggc tttgatcttt ctggattgtt tgaggaaaag ggcgacgaag    1200
caaggtttgt gtctggtgcg tcggtgtcaa agattatgac gaaattggag gaagttgctc    1260
agttggttag tttcaaagtg aggaagaaag attgcagggt tagcttcgag ggttcaagag    1320
aaggggtaaa agggccgttg agtatcgctg ctgaggtatt cgagttaacc ccgtctttgg    1380
ttgttgttga agtgaagaaa aaaggagggg ataaagttga gtatgatagg ttttttaaaca   1440 ctgaattgaa gtctgctttg catagtttaa ccatggaaga atctgcaggt tcttcatgtc    1500
aaaatacacc agatgaaact ttgcaacaac gcgcgttttc tgattccgcc attgacaaac    1560
attcagatag cattgaatct ctgaacttag acacctgaag aatgaatgac ctataataag    1620
ataaaaaggg tattttatttt tcaatgtttt tataggctgt gtatttatag tacttaaatt    1680
tatgttactt ttttctccag gattgtcctg ttttttttgtt ttgtgtgtgt cctaatgttg    1740
taagatgaat gccaattcaa ttttaatata ctcaataaaa caaacatgtt atgttttggc    1800
caaaaaaaaa aaaaaaaaaa aaaaaaaaaa aaaaaaaaa                             1840
```

<210> SEQ ID NO 37
<211> LENGTH: 516
<212> TYPE: PRT
<213> ORGANISM: Pisum sativum

<400> SEQUENCE: 37

```
Met Ala Val Val Ala Ala Pro Lys Lys Asn Asn Ser Phe Asn Lys Lys
1               5                   10                  15

Asp Asn Pro Asn Leu Leu Leu Gly Arg Phe Glu Leu Gly Lys Leu Leu
                20                  25                  30

Gly His Gly Thr Phe Ala Lys Val His Leu Ala Lys Asn Ile Lys Thr
            35                  40                  45

Gly Glu Ala Val Ala Ile Lys Ile Ile Ser Lys Asp Lys Ile Leu Lys
        50                  55                  60

Ser Gly Leu Val Ser His Ile Lys Arg Glu Ile Ser Ile Leu Arg Arg
65                  70                  75                  80

Val Arg His Pro Asn Ile Val Gln Leu Phe Glu Val Met Ala Thr Lys
                85                  90                  95

Thr Lys Ile Tyr Phe Val Met Glu Tyr Val Arg Gly Gly Glu Leu Phe
                100                 105                 110
```

```
Asn Lys Val Ala Lys Gly Arg Leu Lys Glu Val Ala Arg Lys Tyr
        115                 120                 125
Phe Gln Gln Leu Ile Cys Ala Val Glu Phe Cys His Ala Arg Gly Val
130                 135                 140
Phe His Arg Asp Ile Lys Pro Glu Asn Leu Leu Leu Asp Glu Asn Gly
145                 150                 155                 160
Asn Leu Lys Val Ser Asp Phe Gly Leu Ser Ala Val Ser Asp Glu Ile
                165                 170                 175
Lys Gln Asp Gly Leu Phe His Thr Phe Cys Gly Thr Pro Ala Tyr Val
                180                 185                 190
Ala Pro Glu Val Leu Ser Arg Lys Gly Tyr Asp Gly Lys Val Asp
                195                 200                 205
Ile Trp Ser Cys Gly Val Val Leu Phe Val Leu Met Ala Gly Tyr Leu
                210                 215                 220
Pro Phe His Asp Pro Asn Asn Val Met Val Met Tyr Lys Lys Ile Tyr
225                 230                 235                 240
Lys Gly Asp Phe Arg Cys Pro Arg Trp Phe Ser Pro Glu Leu Val Asn
                245                 250                 255
Leu Leu Thr Arg Leu Leu Asp Thr Lys Pro Gln Thr Arg Ile Ser Ile
                260                 265                 270
Pro Glu Ile Met Glu Asn Arg Trp Phe Lys Ile Gly Phe Lys Arg Ile
                275                 280                 285
Lys Phe Tyr Val Glu Asp Val Val Cys Asn Leu Asp Ser Leu Gly
                290                 295                 300
Leu Asp Gly Asn Asn Gly Asn Asp Gly Asn Asp Lys Lys Val Leu
305                 310                 315                 320
Asn Ile Asp Glu His Arg Asp Glu Ala Leu Glu Ser Val Ser Glu Ser
                325                 330                 335
Glu Trp Asp Ser Glu Val Val Asn Arg Arg Lys Asn Arg Gln Leu Gly
                340                 345                 350
Ser Leu Pro Arg Pro Ala Ser Leu Asn Ala Phe Asp Ile Ile Ser Phe
                355                 360                 365
Ser Gln Gly Phe Asp Leu Ser Gly Leu Phe Glu Glu Lys Gly Asp Glu
                370                 375                 380
Ala Arg Phe Val Ser Gly Ala Ser Val Ser Lys Ile Met Thr Lys Leu
385                 390                 395                 400
Glu Glu Val Ala Gln Leu Val Ser Phe Lys Val Arg Lys Lys Asp Cys
                405                 410                 415
Arg Val Ser Phe Glu Gly Ser Arg Glu Gly Val Lys Gly Pro Leu Ser
                420                 425                 430
Ile Ala Ala Glu Val Phe Glu Leu Thr Pro Ser Leu Val Val Val Glu
                435                 440                 445
Val Lys Lys Lys Gly Gly Asp Lys Val Glu Tyr Asp Arg Phe Leu Asn
                450                 455                 460
Thr Glu Leu Lys Ser Ala Leu His Ser Leu Thr Met Glu Glu Ser Ala
465                 470                 475                 480
Gly Ser Ser Cys Gln Asn Thr Pro Asp Glu Thr Leu Gln Gln Arg Ala
                485                 490                 495
Phe Ser Asp Ser Ala Ile Asp Lys His Ser Asp Ser Ile Glu Ser Leu
                500                 505                 510
Asn Leu Asp Thr
                515
```

<210> SEQ ID NO 38
<211> LENGTH: 1124
<212> TYPE: DNA
<213> ORGANISM: Medicago truncatula
<220> FEATURE:
<221> NAME/KEY: misc_feature
<222> LOCATION: (5)..(5)
<223> OTHER INFORMATION: n is a, c, g, or t

<400> SEQUENCE: 38

```
tgatnacgcc aagctcgaaa ttaaccctca ctaaagggaa caaaagctgg agctccaccg      60
cggtggcggc cgctctagag ccagtgcctc ccccgcgcgg ctggaggtac atttccatca     120
ctagaagaaa aaaaaatcat aacacctcca attccaatcc aatagaaccc tttccactcc     180
ggattatcca tccatggcag ttgtagctgc tcccaagaag aacaactcaa tgaacaagaa     240
agataatcca aatcttctat tgggacgttt tgaattagga aaacttcttg gccatggaac     300
ctttgcaaaa gtccaccttg ccaagaacct caaacaggt gaatccgtag ctataaagat      360
cataagtaaa gataaaatcc ttaaagtgg tttagtttca catatcaaac gagaaatctc      420
cattctgcgc cgtgttcgtc accccaacat tgttcaactc tttgaagtca tggctacaaa     480
gacaaagatt tactttgtga tggaatatgt acgaggtggt gagcttttca caaggttgc      540
taaaggtagg ttgaaagaag aagttgcaag gaaatatttt cagcagttaa tatgtgctgt     600
tggattttgt catgctagag gtgtttttca tagagatcta aagcctgaaa atttgttgct     660
tgatgaaaaa ggtaacctta agtttcaga ttttggtctt agtgctgtgt cggatgaaat      720
taagcaagat gggttgtttc atacttttg tggtacacct gcttatgttg ctcctgaggt     780
tttgtctagg aaaggttatg atggtgctaa ggttgatatt tggtcttgtg ggttgtttt     840
gtttgttttg atggctggtt atttacctt tcatgatcct aataatgtta tggctatgta      900
taagaagatt tataaaggtg aatttaggtg tcctagatgg ttttcaccag aacttgttag     960
tcttcttact aggcttcttg atattaaacc tcaaactagg atttctattc ctgagattat    1020
ggagaatcgt tggtttaaga taggttttaa gcatattaaa ttttatgttg aggatgatgt    1080
tgtttgtgat cttgattcac ttgatcttga tggtgaggat aata                     1124
```

<210> SEQ ID NO 39
<211> LENGTH: 310
<212> TYPE: PRT
<213> ORGANISM: Medicago truncatula

<400> SEQUENCE: 39

```
Met Ala Val Val Ala Ala Pro Lys Lys Asn Asn Ser Met Asn Lys Lys
1               5                   10                  15

Asp Asn Pro Asn Leu Leu Leu Gly Arg Phe Glu Leu Gly Lys Leu Leu
            20                  25                  30

Gly His Gly Thr Phe Ala Lys Val His Leu Ala Lys Asn Leu Lys Thr
        35                  40                  45

Gly Glu Ser Val Ala Ile Lys Ile Ile Ser Lys Asp Lys Ile Leu Lys
    50                  55                  60

Ser Gly Leu Val Ser His Ile Lys Arg Glu Ile Ser Ile Leu Arg Arg
65                  70                  75                  80

Val Arg His Pro Asn Ile Val Gln Leu Phe Glu Val Met Ala Thr Lys
                85                  90                  95

Thr Lys Ile Tyr Phe Val Met Glu Tyr Val Arg Gly Gly Glu Leu Phe
            100                 105                 110
```

-continued

```
Asn Lys Val Ala Lys Gly Arg Leu Lys Glu Glu Val Ala Arg Lys Tyr
        115                 120                 125
Phe Gln Gln Leu Ile Cys Ala Val Gly Phe Cys His Ala Arg Gly Val
    130                 135                 140
Phe His Arg Asp Leu Lys Pro Glu Asn Leu Leu Asp Glu Lys Gly
145                 150                 155                 160
Asn Leu Lys Val Ser Asp Phe Gly Leu Ser Ala Val Ser Asp Glu Ile
                165                 170                 175
Lys Gln Asp Gly Leu Phe His Thr Phe Cys Gly Thr Pro Ala Tyr Val
            180                 185                 190
Ala Pro Glu Val Leu Ser Arg Lys Gly Tyr Asp Gly Ala Lys Val Asp
        195                 200                 205
Ile Trp Ser Cys Gly Val Val Leu Phe Val Leu Met Ala Gly Tyr Leu
    210                 215                 220
Pro Phe His Asp Pro Asn Asn Val Met Ala Met Tyr Lys Lys Ile Tyr
225                 230                 235                 240
Lys Gly Glu Phe Arg Cys Pro Arg Trp Phe Ser Pro Glu Leu Val Ser
                245                 250                 255
Leu Leu Thr Arg Leu Leu Asp Ile Lys Pro Gln Thr Arg Ile Ser Ile
            260                 265                 270
Pro Glu Ile Met Glu Asn Arg Trp Phe Lys Ile Gly Phe Lys His Ile
        275                 280                 285
Lys Phe Tyr Val Glu Asp Val Val Cys Asp Leu Asp Ser Leu Asp
    290                 295                 300
Leu Asp Gly Glu Asp Asn
305                 310

<210> SEQ ID NO 40
<211> LENGTH: 2083
<212> TYPE: DNA
<213> ORGANISM: Arabidopsis thaliana

<400> SEQUENCE: 40
taaacagaga cgcgttgcta tttttagtga tgaatctcta aaaacagtag agagagaaac      60
cttcttcttc tttcttcttc ttctacaaaa tttcacaaaa cgagagagag gagagattca     120
aacaaacgaa tcaacaggtg agaaattcga aatctttgcg agctcgtctc gcccagaatc     180
tcgatttctc cacctttcct cttcaattca tcttccaaat ccctaaaaaa aagactcaaa     240 cttttaatt ttggtccaaa aaagactcaa actttcttca tcaatggcgg agaaaatcac     300
gagagagacg tcgttaccta agagagaag cagcccacaa gctctaatcc tgggacgata     360
cgaaatgggt aagcttctcg gccatggtac cttcgctaaa gtttacctcg cacgtaacgt     420
gaaaacaaac gaaagcgtag caatcaaagt aatcgacaag gagaaagttc tcaaaggagg     480
tttaatcgca cacatcaaac gcgagatctc gattcttcga cgtgttcgtc acccaaacat     540
cgttcagcta ttcgaagtca tggcgacgaa agctaagatc tatttcgtga tggagtatgt     600
tcgtggaggt gagttattca ataaagtagc taaaggtcgt cttaaagaag aagtagctcg     660
caaatatttc cagcaattga tctctgctgt tactttctgt cacgcgagag gtgtttatca     720
tagagatctg aaacctgaga atcttttgtt agatgagaat ggtaatctta aagtctctga     780
ctttggactt agtgctgtct ctgatcagat tcgtcaagat gggcttttc atacgttttg     840 tggtactcct gcttatgttg ctcctgaggt tttagctagg aaaggttatg atgctgctaa     900
agttgatatt tggtcttgtg gtgttatctt gtttgtgttg atggctggtt atttgccgtt     960
```

-continued

```
tcatgatcgg aatgttatgg ctatgtataa gaagatttac agaggggagt ttaggtgtcc    1020
taggtggttt tctactgagc ttaccaggtt gttgtcgaag cttttggaga cgaatccgga    1080
gaaacggttc actttccctg agattatgga gaattcttgg tttaagaaag ggtttaagca    1140
tattaagttt tatgtggagg atgataagtt gtgtaatgtt gttgatgatg atgaactgga    1200
gtctgactcg gtggagtcgg atagagattc cgcggcttct gagtcggaga ttgagtattt    1260
ggagcctagg aggagagttg gagggttgcc tagacctgcg agtttgaatg ctttcgatat    1320
tatatcgttt tcgcaaggtt ttgatttatc gggtttgttt gatgacgatg gggagggttc    1380
taggtttgtt tcgggagctc cggtttcgaa gattatatcg aagttggaag agattgctaa    1440
agttgtgagc tttactgtga ggaagaagga ttgtagggta agtcttgaag gttcaagaca    1500
aggagtgaaa ggtccattga cgattgcagc agagatattc gaattgacac catcgttggt    1560
tgttgtggaa gtcaagaaga aggaggaga taaaacagag tatgaagatt tctgtaacaa    1620
tgaattgaaa cccaagttgc aaaacttgac agctgatgat gtagtagctg agcctgtcgc    1680
ggtttcagcg gttgatgaaa ccgctatccc gaattctcca accatttctt tcttgccgtc    1740
tgacactgaa tagaaggact tgatggaaga ccacaaagcc agagatcatg aggggtatgt    1800
atgtacactg tatgtttttgg gttttgtaat ctggattggg aaagaaaaaa agctgcttac    1860
ggttggtgaa atttagaatc gaattatatg taatacttat gtttctgttg gagaggatcg    1920
ttagagaaat tgagttatgt tttttactaa cctttttagca gttttttttt gtaatgggag    1980
aattgtaaac agtttcgcat aatcagatct ttgatatgta taaaaacaat gaaataaata    2040
aaagaaagtt cctttcttct tagtgaactc tcgagagatc tat                     2083
```

<210> SEQ ID NO 41
<211> LENGTH: 489
<212> TYPE: PRT
<213> ORGANISM: Arabidopsis thaliana

<400> SEQUENCE: 41

```
Met Ala Glu Lys Ile Thr Arg Glu Thr Ser Leu Pro Lys Glu Arg Ser
1               5                   10                  15

Ser Pro Gln Ala Leu Ile Leu Gly Arg Tyr Glu Met Gly Lys Leu Leu
                20                  25                  30

Gly His Gly Thr Phe Ala Lys Val Tyr Leu Ala Arg Asn Val Lys Thr
            35                  40                  45

Asn Glu Ser Val Ala Ile Lys Val Ile Asp Lys Glu Lys Val Leu Lys
        50                  55                  60

Gly Gly Leu Ile Ala His Ile Lys Arg Glu Ile Ser Ile Leu Arg Arg
65                  70                  75                  80

Val Arg His Pro Asn Ile Val Gln Leu Phe Glu Val Met Ala Thr Lys
                85                  90                  95

Ala Lys Ile Tyr Phe Val Met Glu Tyr Val Arg Gly Gly Glu Leu Phe
            100                 105                 110

Asn Lys Val Ala Lys Gly Arg Leu Lys Glu Glu Val Ala Arg Lys Tyr
        115                 120                 125

Phe Gln Gln Leu Ile Ser Ala Val Thr Phe Cys His Ala Arg Gly Val
    130                 135                 140

Tyr His Arg Asp Leu Lys Pro Glu Asn Leu Leu Leu Asp Glu Asn Gly
145                 150                 155                 160

Asn Leu Lys Val Ser Asp Phe Gly Leu Ser Ala Val Ser Asp Gln Ile
                165                 170                 175
```

```
Arg Gln Asp Gly Leu Phe His Thr Phe Cys Gly Thr Pro Ala Tyr Val
                180                 185                 190

Ala Pro Glu Val Leu Ala Arg Lys Gly Tyr Asp Ala Ala Lys Val Asp
            195                 200                 205

Ile Trp Ser Cys Gly Val Ile Leu Phe Val Leu Met Ala Gly Tyr Leu
        210                 215                 220

Pro Phe His Asp Arg Asn Val Met Ala Met Tyr Lys Lys Ile Tyr Arg
225                 230                 235                 240

Gly Glu Phe Arg Cys Pro Arg Trp Phe Ser Thr Leu Thr Arg Leu
                245                 250                 255

Leu Ser Lys Leu Leu Glu Thr Asn Pro Glu Lys Arg Phe Thr Phe Pro
            260                 265                 270

Glu Ile Met Glu Asn Ser Trp Phe Lys Lys Gly Phe Lys His Ile Lys
            275                 280                 285

Phe Tyr Val Glu Asp Asp Lys Leu Cys Asn Val Val Asp Asp Asp Glu
        290                 295                 300

Leu Glu Ser Asp Ser Val Glu Ser Asp Arg Asp Ser Ala Ala Ser Glu
305                 310                 315                 320

Ser Glu Ile Glu Tyr Leu Glu Pro Arg Arg Arg Val Gly Gly Leu Pro
                325                 330                 335

Arg Pro Ala Ser Leu Asn Ala Phe Asp Ile Ile Ser Phe Ser Gln Gly
                340                 345                 350

Phe Asp Leu Ser Gly Leu Phe Asp Asp Gly Glu Gly Ser Arg Phe
            355                 360                 365

Val Ser Gly Ala Pro Val Ser Lys Ile Ile Ser Lys Leu Glu Glu Ile
            370                 375                 380

Ala Lys Val Val Ser Phe Thr Val Arg Lys Lys Asp Cys Arg Val Ser
385                 390                 395                 400

Leu Glu Gly Ser Arg Gln Gly Val Lys Gly Pro Leu Thr Ile Ala Ala
                405                 410                 415

Glu Ile Phe Glu Leu Thr Pro Ser Leu Val Val Glu Val Lys Lys
            420                 425                 430

Lys Gly Gly Asp Lys Thr Glu Tyr Glu Asp Phe Cys Asn Asn Glu Leu
            435                 440                 445

Lys Pro Lys Leu Gln Asn Leu Thr Ala Asp Asp Val Val Ala Glu Pro
450                 455                 460

Val Ala Val Ser Ala Val Asp Glu Thr Ala Ile Pro Asn Ser Pro Thr
465                 470                 475                 480

Ile Ser Phe Leu Pro Ser Asp Thr Glu
                485

<210> SEQ ID NO 42
<211> LENGTH: 2449
<212> TYPE: DNA
<213> ORGANISM: Arabidopsis thaliana

<400> SEQUENCE: 42
tattccattt ccattgtttc tatatctatg gaaatgaaaa ataattcatt gatcttttct      60
atctaaataa aaaaattctc cttcggtttc aaattatttt ttattgtttg tattagaaac    120
aatcaatttt tctaacatag tattagtttt ttaagcattt aaagcaaaaa aaaaaaaaac    180
agttgaccaa taggctatat atatgtgttg gtggtataca aaaagtgaga tttatttgta    240
taccaattct gaaacatttc caaatatacc acaagaaaaa tcctatttct ggaaaaagcc    300
ctaaaaacag aacagaggaa gacgagaaaa acagagaaag agagagagag agagagagat    360
```

| | |
|---|---|
| cgtcttcttc tacaacctct caataatcaa acaaaaaaac gtgttttttt ttttttttgcg | 420 |
| aattcgatct tcgatcaaga agatcttgat ctcaaaatcc aaactttcct tcaccatttc | 480 |
| atgagaatct ctcgctttca atggcggatt tgttaagaaa agtgaaatcg ataaagaaga | 540 |
| agcaggatca gagcaatcat caagctctga tccttggcaa atacgaaatg ggtaggcttc | 600 |
| ttggccacgg aaccttcgct aaagtctatc tcgcacgaaa cgctcaatct ggagaaagcg | 660 |
| tagcgatcaa ggtaattgac aaagagaaag ttctcaaatc cggtttaatc gcacacatca | 720 |
| aacgcgagat ctcgatcttg cgccgtgttc gtcatcctaa catcgttcag ctattcgaag | 780 |
| tcatggcgac gaaatctaag atctatttcg taatggaata tgttaaagga ggtgaattgt | 840 |
| tcaacaaggt agctaaagga aggttaaaag aagaaatggc acgtaaatat tttcaacagt | 900 |
| tgatctcagc cgtatcgttt tgtcacttcc gtggtgttta tcatcgagat ttgaaaccgg | 960 |
| agaatcttct tttagacgaa aatggaaacc taaaagtctc tgattttggt cttagtgctg | 1020 |
| tttctgatca gattcgacaa gatgggttat ttcatacttt ttgtgggacc cctgcttacg | 1080 |
| tggcaccgga ggttcttgct cggaaaggct acgatggagc taaagtcgat atttggtctt | 1140 |
| gtggagtgat cttgtttgtg ttaatggcag ggtttcttcc ttttcatgat cggaatgtta | 1200 |
| tggctatgta taagaagatt tacagaggag attttaggtg tccgagatgg tttccggttg | 1260 |
| agattaaccg gttattgatt cgaatgttgg agactaaacc ggagagacgg tttacaatgc | 1320 |
| cggatattat ggagactagt tggttcaaga aaggttttaa gcatattaag tttatgttg | 1380 |
| aagatgatca tcagctttgt aacgttgctg atgatgatga gatcgaatcg attgaatcgg | 1440 |
| tttcggggag gtcttctacg gtttctgaac cggaagactt cgagtctttt gatgggagga | 1500 |
| gaagaggtgg ttcgatgcct agaccggcaa gtttgaatgc tttcgatctc atttcgtttt | 1560 |
| cgccaggttt tgatctttcg ggtttgtttg aggatgatgg tgaaggatct aggtttgtgt | 1620 |
| ctggtgctcc tgttggtcag atcatttcta agttggagga aatcgcgagg attgtgagtt | 1680 |
| ttactgtgcg aaagaaggat tgtaaagtga gtcttgaagg ttcaagagaa ggaagtatga | 1740 |
| aaggtccatt gtcaattgct gctgagatat ttgaactgac accagctttg gttgttgttg | 1800 |
| aagtgaagaa gaaaggaggt gataaaatgg agtatgatga gttttgtaat aaggagttga | 1860 |
| aacctaagtt gcagaatttg tcttccgaaa atggccaacg ggtttctggt tcgcgttctt | 1920 |
| tgccatcgtt tttactttct gatactgatt aggaagatga aaaatgaagt ttttgtttct | 1980 |
| gttttattag ttttgtgact catatgtggg gttaacgact tgtaatgttc ttgttctttg | 2040 |
| atggtgtgtg agagacatta gaatttagac ctaaagagag tggtgagata tgaatcattg | 2100 |
| atgtgtagaa aacacagatg gaataaacaa gtttctttat gagtttgctt cttttttttc | 2160 |
| tttcttttc cttcttttga attttaattc tgttagtttg aaatatgaca gaaattcact | 2220 |
| tagaacaaga ttgtgtaatt tctgttggaa attttgtcta ctaacgtcaa ttaatatgac | 2280 |
| ggtttatgat atataattga acatgtagag tttacaaaaa caaaatcttg agaagaaagt | 2340 |
| ttagcattat aatccaagcc acaccattag ctaatccaaa tttgtgttgt tcttttaaat | 2400 |
| atgttatatt ctagtcatgc acctttaacc ataaacaatt tattaatcc | 2449 |

<210> SEQ ID NO 43
<211> LENGTH: 483
<212> TYPE: PRT
<213> ORGANISM: Arabidopsis thaliana

<400> SEQUENCE: 43

-continued

```
Met Ala Asp Leu Leu Arg Lys Val Lys Ser Ile Lys Lys Lys Gln Asp
1               5                   10                  15

Gln Ser Asn His Gln Ala Leu Ile Leu Gly Lys Tyr Glu Met Gly Arg
            20                  25                  30

Leu Leu Gly His Gly Thr Phe Ala Lys Val Tyr Leu Ala Arg Asn Ala
        35                  40                  45

Gln Ser Gly Glu Ser Val Ala Ile Lys Val Ile Asp Lys Glu Lys Val
50                  55                  60

Leu Lys Ser Gly Leu Ile Ala His Ile Lys Arg Glu Ile Ser Ile Leu
65                  70                  75                  80

Arg Arg Val Arg His Pro Asn Ile Val Gln Leu Phe Glu Val Met Ala
                85                  90                  95

Thr Lys Ser Lys Ile Tyr Phe Val Met Glu Tyr Val Lys Gly Gly Glu
            100                 105                 110

Leu Phe Asn Lys Val Ala Lys Gly Arg Leu Lys Glu Glu Met Ala Arg
        115                 120                 125

Lys Tyr Phe Gln Gln Leu Ile Ser Ala Val Ser Phe Cys His Phe Arg
130                 135                 140

Gly Val Tyr His Arg Asp Leu Lys Pro Glu Asn Leu Leu Leu Asp Glu
145                 150                 155                 160

Asn Gly Asn Leu Lys Val Ser Asp Phe Gly Leu Ser Ala Val Ser Asp
                165                 170                 175

Gln Ile Arg Gln Asp Gly Leu Phe His Thr Phe Cys Gly Thr Pro Ala
            180                 185                 190

Tyr Val Ala Pro Glu Val Leu Ala Arg Lys Gly Tyr Asp Gly Ala Lys
        195                 200                 205

Val Asp Ile Trp Ser Cys Gly Val Ile Leu Phe Val Leu Met Ala Gly
210                 215                 220

Phe Leu Pro Phe His Asp Arg Asn Val Met Ala Met Tyr Lys Lys Ile
225                 230                 235                 240

Tyr Arg Gly Asp Phe Arg Cys Pro Arg Trp Phe Pro Val Glu Ile Asn
                245                 250                 255

Arg Leu Leu Ile Arg Met Leu Glu Thr Lys Pro Glu Arg Arg Phe Thr
            260                 265                 270

Met Pro Asp Ile Met Glu Thr Ser Trp Phe Lys Lys Gly Phe Lys His
        275                 280                 285

Ile Lys Phe Tyr Val Glu Asp Asp His Gln Leu Cys Asn Val Ala Asp
290                 295                 300

Asp Asp Glu Ile Glu Ser Ile Glu Ser Val Ser Gly Arg Ser Ser Thr
305                 310                 315                 320

Val Ser Glu Pro Glu Asp Phe Ser Phe Asp Gly Arg Arg Gly
                325                 330                 335

Gly Ser Met Pro Arg Pro Ala Ser Leu Asn Ala Phe Asp Leu Ile Ser
            340                 345                 350

Phe Ser Pro Gly Phe Asp Leu Ser Gly Leu Phe Glu Asp Asp Gly Glu
        355                 360                 365

Gly Ser Arg Phe Val Ser Gly Ala Pro Val Gly Gln Ile Ile Ser Lys
370                 375                 380

Leu Glu Glu Ile Ala Arg Ile Val Ser Phe Thr Val Arg Lys Lys Asp
385                 390                 395                 400

Cys Lys Val Ser Leu Glu Gly Ser Arg Glu Gly Ser Met Lys Gly Pro
                405                 410                 415

Leu Ser Ile Ala Ala Glu Ile Phe Glu Leu Thr Pro Ala Leu Val Val
```

|  |  | 420 |  |  |  | 425 |  |  |  | 430 |  |
|---|---|---|---|---|---|---|---|---|---|---|---|
| Val | Glu | Val | Lys | Lys | Lys | Gly | Gly | Asp | Lys | Met | Glu | Tyr | Asp | Glu | Phe |
|  |  |  | 435 |  |  |  |  | 440 |  |  |  | 445 |  |  |  |

Cys Asn Lys Glu Leu Lys Pro Lys Leu Gln Asn Leu Ser Ser Glu Asn
450 455 460

Gly Gln Arg Val Ser Gly Ser Arg Ser Leu Pro Ser Phe Leu Leu Ser
465 470 475 480

Asp Thr Asp

<210> SEQ ID NO 44
<211> LENGTH: 1788
<212> TYPE: DNA
<213> ORGANISM: Arabidopsis thaliana

<400> SEQUENCE: 44

```
accactttct tggacacgg atggctcaag ccttggctca accaccactg gtggtcacca      60
ccgtcgtccc agacccgccg ccgccgccac caccaccgca cccaaagccg tatgctctac    120
gatacatggc ggatcttctt ggccggattg gtataatgga tacagacaaa gatggtaaca    180
tcagcccaca gagtccgagg agtcctagga gcccaagaaa caacattctc atggggaagt    240
acgagcttgg gaagcttctc ggccacggaa ccttttgcaaa ggtttattta gctcaaaaca    300
tcaaatctgg agataaagtc gccattaaag tcatcgacaa ggagaagatt atgaagagtg    360
gtttggttgc tcacatcaaa cgggaaatct ctatcctccg ccgtgtccgt caccttaca     420
tcgttcatct attcgaggtt atggcgacga agtccaagat ttactttgtg atggagtacg    480
ttggaggcgg cgagttgttc aacacggttg ctaaaggtcg attgcccgag gaaactgctc    540
ggagatattt ccagcagctg atctcctctg tttcgttctg ccatggccgc ggtgtttacc    600
accgtgacct aaaccagag aatctgcttt tagacaacaa agggaacctt aaagtatctg     660
actttggtct cagcgcggtg gcagagcagc ttcgtcaaga cgggctctgc cacacgtttt    720
gcgggactcc agcgtatatt gcacccgagg ttttgactag aaaagggtac gatgcagcga    780
aagccgatgt ttggtcatgt ggagtgatct tattcgtgtt gatggctggt cacattccgt    840
tctacgacaa gaacataatg gttatgtaca agaagattta caaggggaa tttaggtgtc     900
ctcgttggtt ttcatcggat cttgttcggt tattgactcg gcttcttgat acgaatccgg    960
atactcggat tacaataccc gagatcatga agaacagatg gttcaagaaa ggattcaaac   1020
atgttaaatt ctcatcgaa gatgataaac tgtgtaggga gatgaagat gaggaggaag     1080
aggcatcatc atcaggccgc tcttcgacag tttcagagag cgatgcagag ttcgatgtaa   1140
aacggatggg aataggttca atgccaagac cctcgagctt aaacgcgttt gacattatat   1200
cttctctcttc agggtttgat ctgtctggtt tgtttgagga agaaggagga aagggacga   1260
ggtttgtgtc aggtgctcct gtttcaaaga tcatatcgaa gctggaagag attgcgaaaa   1320
tcgtgagctt tactgtgagg aagaaagaat ggagtttgag attagaaggt tgtagagaag   1380
gagcaaaagg accgttgaca attgcggctg agatatttga gctgactcca tctctagtgg   1440
tggtggaggt gaagaagaaa ggaggagaca gagaagagta tgaagagttt tgcaacaagg   1500
aactcagacc agagctggag aaactaatcc atgaagaagt tgtagtagaa gaagcattgt   1560
atttgccatc tgatactgaa tagtataaac caaggaaggc tgataccaag aatatccaag   1620
aaacaagatt gtgttacatt cttttgttac tattgattat ttattcgtta ttcttgttct   1680
atgttaatgt tgatgttggt gtaaaactga gagatttcgg agatcttcac gatttgttgt   1740
```
gatctccgaa atctcccagt gtgtgtttat gtatataagt ggtattgt 1788

<210> SEQ ID NO 45
<211> LENGTH: 520
<212> TYPE: PRT
<213> ORGANISM: Arabidopsis thaliana

<400> SEQUENCE: 45

```
Met Ala Gln Ala Leu Ala Gln Pro Pro Leu Val Thr Thr Val Val
1               5                   10                  15

Pro Asp Pro Pro Pro Pro Pro Pro His Pro Lys Pro Tyr Ala
            20                  25                  30

Leu Arg Tyr Met Ala Asp Leu Leu Gly Arg Ile Gly Ile Met Asp Thr
            35                  40                  45

Asp Lys Asp Gly Asn Ile Ser Pro Gln Ser Pro Arg Ser Pro Arg Ser
50                  55                  60

Pro Arg Asn Asn Ile Leu Met Gly Lys Tyr Glu Leu Gly Lys Leu Leu
65                  70                  75                  80

Gly His Gly Thr Phe Ala Lys Val Tyr Leu Ala Gln Asn Ile Lys Ser
                85                  90                  95

Gly Asp Lys Val Ala Ile Lys Val Ile Asp Lys Glu Lys Ile Met Lys
            100                 105                 110

Ser Gly Leu Val Ala His Ile Lys Arg Glu Ile Ser Ile Leu Arg Arg
        115                 120                 125

Val Arg His Pro Tyr Ile Val His Leu Phe Glu Val Met Ala Thr Lys
130                 135                 140

Ser Lys Ile Tyr Phe Val Met Glu Tyr Val Gly Gly Gly Glu Leu Phe
145                 150                 155                 160

Asn Thr Val Ala Lys Gly Arg Leu Pro Glu Glu Thr Ala Arg Arg Tyr
                165                 170                 175

Phe Gln Gln Leu Ile Ser Ser Val Ser Phe Cys His Gly Arg Gly Val
            180                 185                 190

Tyr His Arg Asp Leu Lys Pro Glu Asn Leu Leu Leu Asp Asn Lys Gly
        195                 200                 205

Asn Leu Lys Val Ser Asp Phe Gly Leu Ser Ala Val Ala Glu Gln Leu
210                 215                 220

Arg Gln Asp Gly Leu Cys His Thr Phe Cys Gly Thr Pro Ala Tyr Ile
225                 230                 235                 240

Ala Pro Glu Val Leu Thr Arg Lys Gly Tyr Asp Ala Ala Lys Ala Asp
                245                 250                 255

Val Trp Ser Cys Gly Val Ile Leu Phe Val Leu Met Ala Gly His Ile
            260                 265                 270

Pro Phe Tyr Asp Lys Asn Ile Met Val Met Tyr Lys Lys Ile Tyr Lys
        275                 280                 285

Gly Glu Phe Arg Cys Pro Arg Trp Phe Ser Ser Asp Leu Val Arg Leu
290                 295                 300

Leu Thr Arg Leu Leu Asp Thr Asn Pro Asp Thr Arg Ile Thr Ile Pro
305                 310                 315                 320

Glu Ile Met Lys Asn Arg Trp Phe Lys Lys Gly Phe Lys His Val Lys
                325                 330                 335

Phe Tyr Ile Glu Asp Asp Lys Leu Cys Arg Glu Asp Glu Asp Glu Glu
            340                 345                 350

Glu Glu Ala Ser Ser Ser Gly Arg Ser Ser Thr Val Ser Glu Ser Asp
        355                 360                 365
```

```
Ala Glu Phe Asp Val Lys Arg Met Gly Ile Gly Ser Met Pro Arg Pro
        370                 375                 380

Ser Ser Leu Asn Ala Phe Asp Ile Ile Ser Phe Ser Ser Gly Phe Asp
385                 390                 395                 400

Leu Ser Gly Leu Phe Glu Glu Gly Gly Gly Thr Arg Phe Val
                    405                 410                 415

Ser Gly Ala Pro Val Ser Lys Ile Ile Ser Lys Leu Glu Glu Ile Ala
                420                 425                 430

Lys Ile Val Ser Phe Thr Val Arg Lys Glu Trp Ser Leu Arg Leu
                435                 440                 445

Glu Gly Cys Arg Glu Gly Ala Lys Gly Pro Leu Thr Ile Ala Ala Glu
        450                 455                 460

Ile Phe Glu Leu Thr Pro Ser Leu Val Val Glu Val Lys Lys
465                 470                 475                 480

Gly Gly Asp Arg Glu Glu Tyr Glu Glu Phe Cys Asn Lys Glu Leu Arg
                485                 490                 495

Pro Glu Leu Glu Lys Leu Ile His Glu Glu Val Val Val Glu Glu Ala
                500                 505                 510

Leu Tyr Leu Pro Ser Asp Thr Glu
        515                 520

<210> SEQ ID NO 46
<211> LENGTH: 2506
<212> TYPE: DNA
<213> ORGANISM: Arabidopsis thaliana

<400> SEQUENCE: 46 tctatacccca attcaaaccc aattaactgt tggaagtttt ttcaagctaa ctgtttccat      60
tcaggtgaag gttaccagga ctacaaggca gcaaagtcta caggtaacat ttacacattt     120
cagtttatca tatagtctct ctgatgaagc ataaatatgt gttagcttag gatgaacaag     180
acagtgttat aggggaaggc cgagaaaaaa attccattaa gctcgtctct tgtagagat      240
acatgtacaa catattagca ataaacgaaa aactagccat ttaatcgcca gcaaaaaccg     300
tctaactgcc ttattaagat ctcactctta atttcttttt ttctctgatc ttcctaatca     360
ctctcattac aactctcact ttcatatata tacacaaaac aaattaagta tagtaacaaa     420
gaatgttaat attcgtttct atgataccttc ctcttgttat gtcttcttct ctcgaccttc    480
ctgttttctt aactttgtca ctgttcaatt tcaggtggca aacacattac ttcttcaact    540
tcatctgctt ggtaatgcat cagtttctcc agctgtggtc taagttcctt gttgcaaaac     600
tcttcatact cttctatatt tcctcctttc ttcttcactt caaccaccac aagagatggc     660
gtcagctcaa agatctcgac tctaattgtc aacggtcctt tagctccttc tctacaacct     720
tctagcctca cgctccaatc cttcttcctc accataaatt tcacctcttt ggcaatctct     780
tccaatttcg atatgatctt tgtcatagga gcagcagata caaaccttgc tccttgtcca     840
ccttcttcaa acaaacccga agatctgag aacgataaga tgtcaaatgc gtttagactc      900
gcgggtctcg gcattgaatc aacccttta atatcaaact ctgcatctcc ttctgaagca     960
gtcgatgatc ggcctgatga caatgatgat gaatcgtcat catcattgtc atcatcctcc    1020
ctacataact tatcgttttc aatatagaat ttgacatgtt tgaacccttt cttgaaccat    1080
ctatgcttca tgatctccgg tattgtgatt cgggtatctg gattcgtgtc tagcatccgg    1140
gtcacaagcc ttgcaagctc aggagaaaac catttaggac acttaaactg cccttttatat   1200
atctttgtat acataaccaa tatgttcttg tcatcaaatg gaagataacc agccatcaat    1260
```

```
acaaacaaga tcactccaca agaccaaata tcggcttttg caccttcata acctttcctt    1320
gtcaaaacct caggcgccaa ataagctggt gtcccgcaaa acgtttgaca gattccttct    1380
tgcttgagct gctccgagac aacgctgagc ccaaagtcag agactttcac gttcccttg     1440
tcgtccaaaa gcagattctc aagcttgaga tcgcggtggt aaacaccgcg gctgtggcag    1500
aaagcaacgg atgagatcaa ctgctggaaa tatctcctcg cggttccttc tcgaagccgt    1560
cctctagcca ccgtattata aagctctccg cctcgaacgt actccatcac aatgtaaatc    1620
tttgtcttcg tagccataac ctcgagtagg tgtacaatgt aagggtggcg gacacggcgg    1680
aggattgaaa tctcccgttt aatatgaccg gccaatccac tcttcactat cttctccttg    1740
tcaatgactt tgatggcaac atcctcgcca gaatgaatgt tccgtgctaa atagaccta    1800
gcgaagcttc cgtggccaag aagctttcct atttcgtact tgtccatgag aatagagcct    1860
tgtggagtcc gcggactcct cgggctctct ggagtactgg tctctttgtt cgtattttt     1920
gtaacgattc gagcaagaag acccgccatg aattgtattg gcgttgggcc ggggatggcc    1980
aacggtgtag atagtacttg agccatccgt aggctgagac ttttatttag ttctggttgc    2040
tctctaagtg taaatgtaac tgttgtttgt tgattccgac acggttttac cgggaaacga    2100
accaaaacaa gaaaatgaaa tgaagaaacg gacaaaaata agatatggtg gggttgttgt    2160
ttcggttgtg atgttgtctt aacttggcct ttttcgtgtt cgttttataa cagttttcga    2220
gttgacttta tcttatgttt cgagaagctg aaaagtcatt tgattttaaa atattgctat    2280
ttgatgttga agttttatcc taatccaaat attttgccaa cagaataaca cgttggacgg    2340
attttcaaat tataaaaggc aaacttatat gttctatcca tacgcaatgt caactttgga    2400
atacatttaa gctttcttaa aggacagata ataaggttga cttatcaatg aggctgatag    2460
ataagcagat catggttcgt taagatgtca tcacacatt tattta                   2506
```

<210> SEQ ID NO 47
<211> LENGTH: 502
<212> TYPE: PRT
<213> ORGANISM: Arabidopsis thaliana

<400> SEQUENCE: 47

```
Met Ala Gln Val Leu Ser Thr Pro Leu Ala Ile Pro Gly Pro Thr Pro
1               5                   10                  15

Ile Gln Phe Met Ala Gly Leu Leu Ala Arg Ile Val Thr Lys Asn Thr
            20                  25                  30

Asn Lys Glu Thr Ser Thr Pro Glu Ser Pro Arg Ser Pro Arg Thr Pro
        35                  40                  45

Gln Gly Ser Ile Leu Met Asp Lys Tyr Glu Ile Gly Lys Leu Leu Gly
    50                  55                  60

His Gly Ser Phe Ala Lys Val Tyr Leu Ala Arg Asn Ile His Ser Gly
65                  70                  75                  80

Glu Asp Val Ala Ile Lys Val Ile Asp Lys Glu Lys Ile Val Lys Ser
                85                  90                  95

Gly Leu Ala Gly His Ile Lys Arg Glu Ile Ser Ile Leu Arg Arg Val
            100                 105                 110

Arg His Pro Tyr Ile Val His Leu Leu Glu Val Met Ala Thr Lys Thr
        115                 120                 125

Lys Ile Tyr Ile Val Met Glu Tyr Val Arg Gly Gly Glu Leu Tyr Asn
    130                 135                 140

Thr Val Ala Arg Gly Arg Leu Arg Glu Gly Thr Ala Arg Arg Tyr Phe
```

```
                145                 150                 155                 160
Gln Gln Leu Ile Ser Ser Val Ala Phe Cys His Ser Arg Gly Val Tyr
                    165                 170                 175
His Arg Asp Leu Lys Leu Glu Asn Leu Leu Asp Asp Lys Gly Asn
                180                 185                 190
Val Lys Val Ser Asp Phe Gly Leu Ser Val Val Ser Glu Gln Leu Lys
            195                 200                 205
Gln Glu Gly Ile Cys Gln Thr Phe Cys Gly Thr Pro Ala Tyr Leu Ala
        210                 215                 220
Pro Glu Val Leu Thr Arg Lys Gly Tyr Glu Gly Ala Lys Ala Asp Ile
225                 230                 235                 240
Trp Ser Cys Gly Val Ile Leu Phe Val Leu Met Ala Gly Tyr Leu Pro
                245                 250                 255
Phe Asp Asp Lys Asn Ile Leu Val Met Tyr Thr Lys Ile Tyr Lys Gly
                260                 265                 270
Gln Phe Lys Cys Pro Lys Trp Phe Ser Pro Glu Leu Ala Arg Leu Val
            275                 280                 285
Thr Arg Met Leu Asp Thr Asn Pro Asp Thr Arg Ile Thr Ile Pro Glu
        290                 295                 300
Ile Met Lys His Arg Trp Phe Lys Lys Gly Phe Lys His Val Lys Phe
305                 310                 315                 320
Tyr Ile Glu Asn Asp Lys Leu Cys Arg Glu Asp Asp Asn Asp Asp
                325                 330                 335
Asp Asp Ser Ser Ser Leu Ser Ser Gly Arg Ser Ser Thr Ala Ser Glu
                340                 345                 350
Gly Asp Ala Glu Phe Asp Ile Lys Arg Val Asp Ser Met Pro Arg Pro
                355                 360                 365
Ala Ser Leu Asn Ala Phe Asp Ile Leu Ser Phe Ser Asp Leu Ser Gly
            370                 375                 380
Leu Phe Glu Glu Gly Gly Gln Gly Ala Arg Phe Val Ser Ala Ala Pro
385                 390                 395                 400
Met Thr Lys Ile Ile Ser Lys Leu Glu Glu Ile Ala Lys Glu Val Lys
                405                 410                 415
Phe Met Val Arg Lys Lys Asp Trp Ser Val Arg Leu Glu Gly Cys Arg
                420                 425                 430
Glu Gly Ala Lys Gly Pro Leu Thr Ile Arg Val Glu Ile Phe Glu Leu
            435                 440                 445
Thr Pro Ser Leu Val Val Val Glu Val Lys Lys Gly Gly Asn Ile
450                 455                 460
Glu Glu Tyr Glu Glu Phe Cys Asn Lys Glu Leu Arg Pro Gln Leu Glu
465                 470                 475                 480
Lys Leu Met His Tyr Gln Ala Asp Glu Val Glu Glu Val Met Cys Leu
                485                 490                 495
Pro Pro Glu Ile Glu Gln
            500

<210> SEQ ID NO 48
<211> LENGTH: 29
<212> TYPE: DNA
<213> ORGANISM: Artificial
<220> FEATURE:
<223> OTHER INFORMATION: 3' PCR Primer for Amplification of DNA Molecule
      embedding coding region as shown in SEQ ID NO1

<400> SEQUENCE: 48
```

```
gacccgggat gctgatggcg accgtctcg                                      29
```

<210> SEQ ID NO 49
<211> LENGTH: 29
<212> TYPE: DNA
<213> ORGANISM: Artificial
<220> FEATURE:
<223> OTHER INFORMATION: 3' PCR Primer for Amplification of DNA Molecule
      embedding coding region as shown in SEQ ID NO1

<400> SEQUENCE: 49

```
ctaagcttac ctttcaacct tctcactca                                      29
```

<210> SEQ ID NO 50
<211> LENGTH: 1766
<212> TYPE: DNA
<213> ORGANISM: Oryza sativa

<400> SEQUENCE: 50

```
tttcatttgg agaggacaca gaaaaatttg ctacattgtt tcacaaactt caaatattat     60
tcatttattt gtcagctttc aaactctttg tttcttgttt gttgattaga tcaattcgcc    120
cttgacccgg gatgctgatg gcgaccgtct cgccggcgcg gagggagccg acgccgcagg    180
cggtgcgggc gtccccgatg ccatcggcgg cggcggcgtt ggtgaggaga ggcggtggtg    240
gtagcggggg gacggtgctg gggaagtacg agctggggcg cgtcctggga cagggctcgt    300
tcgcgaaggt gtaccaggcg aggcacctgg agaccgacga gtgcgtggca atcaaggtgc    360
tcgacaagga gaaggccgtg aagggcggga tggtccacct cgtcaagcgc gagatcaacg    420
tgctccgccg ggtgcgccac ccgaacatcg tgcagctgtt cgaggtaatg gccagcaaga    480
ccaagatcta cttcgtcatg gagtatgtcc ccggcggcga gctcttctcc cgcgtctcca    540
agggacgcct cagggaggac accgcgcggc gctactccca gcagcttgtc tccgccgtcg    600
acttctgcca cgcccgcggc gtgttccacc gtgacctcaa gcccgagaac ctcctcgtgg    660
atgagaacgg ggacttgaag gtctcggact tcggcctcgc cgccggcccc gaccagttcg    720
accccgacgg tctgctccac acgttctgcg gcacgccggc ctacgtcgcc cccgaggtgc    780
tcaggcgccg cggatacgac ggcgccaagg cggacatatg gtcatgcggt gtcatcctct    840
ttgcgctcat ggccgggtac ctcccttttcc atgaccacaa catcatggtt ctgtaccgga    900
agatctacaa tggggagttc aggtgtccaa ggtggttctc caaggatttt actagattga    960
taacgcgcct tcttgacgca aaccccaaaa ctaggatcac cgtgccagag atcattgaga   1020
gcgattggtt caagaaagga tacaagccag tcaagtttta cattgaggat gacaagctct   1080
acaacctgtc tgatgacgtg ctgaacttgg agcctgctga tcctgttccc ccaccattgg   1140
gtttggcacc tcctgttcct ccacctccac aaggggatga tcctgatggt tcagggtctg   1200
agtcagattc atcagtcgta tcctgcccgg ccacattgtc aactggggag agccagagag   1260
tccgtgggtc actaccacgc ccagcaagcc ttaatgcatt tgatatcata tcattctcaa   1320
aaggattcaa cttgtctggg ctgtttgagg agaggggaa cgagatcagg tttgtatctg   1380
gtgagcccat gtctgacatt gtaaaaaagc tggaggagat tgcaaggtc aagagcttca    1440 cagtgcggag gaaggactgg cgggtgagca tagagggtac acgcgaagga gttaaggggc   1500
ctctaaccat aggcgcggag atatttgagc ttacactctc ccttgtagta gtggaagtaa   1560
aaagaaaggc agtgataat gaagagtatg aggattctg caacatggag ttgaagccag    1620
gaatgcagca ccttgtgcac cagatgctcc cagctccaaa tggaactcct gtgagtgaga   1680
```
aggttgaaag gtaagcttag aagggcgaat taattcctcg agcgattagg atgatgataa    1740
gtaagtcgac ctagttagtt aattca    1766

<210> SEQ ID NO 51
<211> LENGTH: 520
<212> TYPE: PRT
<213> ORGANISM: Oryza sativa

<400> SEQUENCE: 51

```
Met Leu Met Ala Thr Val Ser Pro Ala Arg Arg Glu Pro Thr Pro Gln
1               5                   10                  15

Ala Val Arg Ala Ser Pro Met Pro Ser Ala Ala Ala Leu Val Arg
            20                  25                  30

Arg Gly Gly Gly Ser Gly Gly Thr Val Leu Gly Lys Tyr Glu Leu
        35                  40                  45

Gly Arg Val Leu Gly Gln Gly Ser Phe Ala Lys Val Tyr Gln Ala Arg
    50                  55                  60

His Leu Glu Thr Asp Glu Cys Val Ala Ile Lys Val Leu Asp Lys Glu
65                  70                  75                  80

Lys Ala Val Lys Gly Gly Met Val His Leu Val Lys Arg Glu Ile Asn
                85                  90                  95

Val Leu Arg Arg Val Arg His Pro Asn Ile Val Gln Leu Phe Glu Val
            100                 105                 110

Met Ala Ser Lys Thr Lys Ile Tyr Phe Val Met Glu Tyr Val Pro Gly
        115                 120                 125

Gly Glu Leu Phe Ser Arg Val Ser Lys Gly Arg Leu Arg Glu Asp Thr
    130                 135                 140

Ala Arg Arg Tyr Ser Gln Gln Leu Val Ser Ala Val Asp Phe Cys His
145                 150                 155                 160

Ala Arg Gly Val Phe His Arg Asp Leu Lys Pro Glu Asn Leu Leu Val
                165                 170                 175

Asp Glu Asn Gly Asp Leu Lys Val Ser Asp Phe Gly Leu Ala Ala Gly
            180                 185                 190

Pro Asp Gln Phe Asp Pro Asp Gly Leu Leu His Thr Phe Cys Gly Thr
        195                 200                 205

Pro Ala Tyr Val Ala Pro Glu Val Leu Arg Arg Gly Tyr Asp Gly
    210                 215                 220

Ala Lys Ala Asp Ile Trp Ser Cys Gly Val Ile Leu Phe Ala Leu Met
225                 230                 235                 240

Ala Gly Tyr Leu Pro Phe His Asp His Asn Ile Met Val Leu Tyr Arg
                245                 250                 255

Lys Ile Tyr Asn Gly Glu Phe Arg Cys Pro Arg Trp Phe Ser Lys Asp
            260                 265                 270

Phe Thr Arg Leu Ile Thr Arg Leu Leu Asp Ala Asn Pro Lys Thr Arg
        275                 280                 285

Ile Thr Val Pro Glu Ile Ile Glu Ser Asp Trp Phe Lys Lys Gly Tyr
    290                 295                 300

Lys Pro Val Lys Phe Tyr Ile Glu Asp Asp Lys Leu Tyr Asn Leu Ser
305                 310                 315                 320

Asp Asp Val Leu Asn Leu Glu Pro Ala Asp Pro Val Pro Pro Leu
                325                 330                 335

Gly Leu Ala Pro Pro Val Pro Pro Pro Gln Gly Asp Asp Pro Asp
            340                 345                 350

Gly Ser Gly Ser Glu Ser Asp Ser Ser Val Val Ser Cys Pro Ala Thr
```

```
                              -continued
         355               360               365
Leu Ser Thr Gly Glu Ser Gln Arg Val Arg Gly Ser Leu Pro Arg Pro
        370               375               380

Ala Ser Leu Asn Ala Phe Asp Ile Ile Ser Phe Ser Lys Gly Phe Asn
385                 390               395               400

Leu Ser Gly Leu Phe Glu Glu Arg Gly Asn Glu Ile Arg Phe Val Ser
                405               410               415

Gly Glu Pro Met Ser Asp Ile Val Lys Lys Leu Glu Glu Ile Ala Lys
            420             425             430

Val Lys Ser Phe Thr Val Arg Arg Lys Asp Trp Arg Val Ser Ile Glu
        435             440             445

Gly Thr Arg Glu Gly Val Lys Gly Pro Leu Thr Ile Gly Ala Glu Ile
        450             455             460

Phe Glu Leu Thr Leu Ser Leu Val Val Val Glu Val Lys Arg Lys Ala
465             470             475                 480

Gly Asp Asn Glu Glu Tyr Glu Asp Phe Cys Asn Met Glu Leu Lys Pro
                485             490             495

Gly Met Gln His Leu Val His Gln Met Leu Pro Ala Pro Asn Gly Thr
            500             505             510

Pro Val Ser Glu Lys Val Glu Arg
        515             520
```